(12) United States Patent
Bacha et al.

(10) Patent No.: US 9,814,693 B2
(45) Date of Patent: Nov. 14, 2017

(54) VETERINARY USE OF DIANHYDROGALACTITOL, DIACETYLDIANHYDROGALACTITOL, AND DIBROMODULCITOL TO TREAT MALIGNANCIES

(71) Applicant: DELMAR PHARMACEUTICALS, INC., Vancouver (CA)

(72) Inventors: Jeffrey A. Bacha, Vancouver (CA); Dennis M. Brown, Menlo Park, CA (US); William J. Garner, San Francisco, CA (US)

(73) Assignee: DELMAR PHARMACEUTICALS, INC., Vancouver (CA)

( * ) Notice: Subject to any disclaimer, the term of this patent is extended or adjusted under 35 U.S.C. 154(b) by 67 days.

(21) Appl. No.: 14/400,271

(22) PCT Filed: May 3, 2013

(86) PCT No.: PCT/US2013/039549
§ 371 (c)(1),
(2) Date: Nov. 10, 2014

(87) PCT Pub. No.: WO2013/169600
PCT Pub. Date: Nov. 14, 2013

(65) Prior Publication Data
US 2015/0099803 A1    Apr. 9, 2015

Related U.S. Application Data

(60) Provisional application No. 61/644,951, filed on May 9, 2012.

(51) Int. Cl.
| | |
|---|---|
| *A61K 31/335* | (2006.01) |
| *A61K 31/336* | (2006.01) |
| *A61K 31/047* | (2006.01) |
| *A61K 45/06* | (2006.01) |
| *G01N 33/50* | (2006.01) |

(52) U.S. Cl.
CPC .......... *A61K 31/336* (2013.01); *A61K 31/047* (2013.01); *A61K 45/06* (2013.01); *G01N 33/5014* (2013.01)

(58) Field of Classification Search
CPC ... A61K 31/336; A61K 45/06; G01N 33/5014
USPC ............. 514/475; 435/4, 6.11, 18, 29; 506/9
See application file for complete search history.

(56) References Cited

U.S. PATENT DOCUMENTS

| | | |
|---|---|---|
| 6,011,069 A | 1/2000 | Inomata et al. |
| 6,443,898 B1 | 9/2002 | Unger et al. |
| 6,573,292 B1 | 6/2003 | Nardella |
| 6,921,772 B2 | 7/2005 | Nardella |
| 7,101,576 B2 | 9/2006 | Hovey et al. |
| 7,314,886 B2 | 1/2008 | Chao et al. |
| 7,318,931 B2 | 1/2008 | Okumu et al. |
| 7,446,122 B2 | 11/2008 | Chao et al. |
| 7,619,005 B2 | 11/2009 | Epstein et al. |
| 7,728,042 B2 | 6/2010 | Eros et al. |
| 7,879,896 B2 | 2/2011 | Allegretti et al. |
| 2002/0037328 A1 | 3/2002 | Brown |
| 2004/0023290 A1 | 2/2004 | Griffin et al. |
| 2006/0018842 A1 | 1/2006 | Blumenthal |
| 2007/0207952 A1 | 9/2007 | Silva et al. |
| 2008/0176923 A1 | 7/2008 | Salama |
| 2008/0275057 A1 | 11/2008 | Kawabe et al. |
| 2009/0318561 A1 | 12/2009 | Davis et al. |

FOREIGN PATENT DOCUMENTS

| | | |
|---|---|---|
| EP | 1332755 A1 | 8/2003 |
| WO | 03/070823 A1 | 8/2003 |

OTHER PUBLICATIONS

S. Kerpel-Fronius et al., "Relation Between Dose, Plasma Concentration and Toxicity in a Phase I Trial Using High Dose Intermittent Administration of an Alkylation Agent, Diacetyldianhydrogalactitol (DADAG)," Cancer Chemother. Pharmacol. 16: 264-268 (1986).
T.S.K. Mok et al., "A Double-Blind Placebo-Controlled Randomized Study of Chinese Herbal Medicine as Complementary Therapy for Reduction of Chemotherapy-Induced Toxicity," Ann. Oncol. 18: 768-774 (2007).
J. Khandare & T. Minko, "Polymer-Drug Conjugates: Progress in Polymeric Prodrugs," Prog. Polymer Sci. 31: 359-397 (2006).
R.T. Eagan et al., "Brief Communication: Phase I Study of a Five-Day Intermittent Schedule for 1,2:5,6-Dianhydrogalactitol (NSC-132313)," J. Natl. Cancer Inst. 56: 179-181.
F.B. Stehman et al., "Phase II Trial of Galactitol 1,2:5,6-Dianhydro (NSC 132313) in the Treatment of Advanced Gynecologic Malignancies: A Gynecologic Oncology Group Study," Gynecol. Oncol. 15: 381-390 (1983).
T. Kimura et al., "A Preliminary Pharmacokinetic Study of Dianhydrogalactitol (NSC-132313) Disposition in the Dog," J. Natl. Cancer Inst. 58: 1311-1314 (1977).
PCT Patent Application Publication No. 2012/024367 by Brown, published on Feb. 23, 2012.

*Primary Examiner* — Raymond Henley, III
(74) *Attorney, Agent, or Firm* — Ditthavong & Steiner, P.C.

(57) ABSTRACT

The present invention is directed to methods for treatment of malignancies in companion animals employing dianhydrogalactitol, diacetyldianhydrogalactitol, and dibromodulcitol, as well as analogs and derivatives thereof, in addition to a method to improve the efficacy and/or reduce the side effects of the administration of a therapeutic agent selected from the group consisting of dianhydrogalactitol, a derivative of dianhydrogalactitol, diacetyldianhydrogalactitol, a derivative of diacetyldianhydrogalactitol, dibromodulcitol, and a derivative of dibromodulcitol to a veterinary subject, the method comprising the steps of: (1 (identifying at least one factor or parameter associated with the efficacy and/or occurrence of side effects of the administration of the therapeutic agent to the veterinary subject; and (2) modifying the factor or parameter to improve the efficacy and/or reduce the side effects of the administration of the therapeutic agent to the veterinary subject.

5 Claims, 4 Drawing Sheets

VETERINARY USE OF DIANHYDROGALACTITOL, DIACETYLDIANHYDROGALACTITOL, AND DIBROMODULCITOL TO TREAT MALIGNANCIES

CROSS-REFERENCES

This application claims the benefit of U.S. Provisional Patent Application Ser. No. 61/644,951 by J. A. Bacha et al., filed on May 9, 2012 and entitled "Veterinary Use of Dianhydrogalactitol, Diacetyldianhydrogalactitol, and Dibromodulcitol to Treat Malignancies," the contents of which are hereby incorporated in their entirety by this reference.

FIELD OF THE INVENTION

The present invention is directed to the use of dianhydrogalactitol, diacetyldianhydrogalactitol, and dibromodulcitol in veterinary medicine, especially to treat malignancies in pets.

BACKGROUND OF THE INVENTION

According to the United States Humane Society, there are approximately 78 million dogs and 86 million cats in the United States. The American Pet Products Manufacturers' Association (APPMA) estimates that 62% of United States households provide a home for a pet, compared with 56% in 1998. The APPMA reported that Americans spent over $13 billion on veterinary care, with the average lifetime cost of care for either a medium-size dog or cat being approximately $10,500. Globally, the growth of the pharmaceutical market for companion animals is comparable to that of human healthcare.

About six million dogs are diagnosed with cancer each year in the United States. Incidence of all cancers was 99.3 per 100,000 dog-years in male dogs and 272.1 in female dogs, due to the high rate of mammary cancer observed in female dogs (bitches). The highest incidence rates were detected for mammary cancer (IR=191.8) and for non-Hodgkin's lymphoma (IR=22.9) in bitches and for non-Hodgkin's lymphoma (IR=19.9) and skin cancer (IR=19.1) in male dogs. Cancer incidence in dogs increases dramatically with age increasing for bitches from 23.7 to 763.2 and for male dogs from 16.5 to 237.6 in animals aged < or =3 years and >9-11 years, respectively.

Incidence rates of cancer in cats are reported as 155.8 per 100,000 animals. The highest incidence rates in cats were detected for lymphoid tumors (IR=48.1) and skin cancer (IR=34.7). With significant incidence also reported for breast (IR=25.4); connective tissue (IR=17.0); mouth and pharynx (IR=11.6); digestive tract (IR=11.2); respiratory (IR=5.0) and bone (IR=4.9).

Cancer, of course, can occur in other species. Several years ago, a top-class thoroughbred race horse was diagnosed with lymphoma; the horse was retired from racing but died during its four-year-old season, an extremely young age for a horse. Such fatalities represent significant economic loss to the owners of such animals.

Similar to humans, cancer is the leading cause of death among older cats and dogs, and accounts for about 50% of deaths each year. Pain is common in pets with cancer, with some tumors causing more pain than others. The issue of pain in cancer in animals is difficult to evaluate, because there is no definite way of evaluating the extent of pain and the resulting discomfort experienced by the animal. However, as in humans, pain is related to the size and location of the cancer and the involvement of nerves; cancer in or associated with organs that have a higher degree of innervation tends to produce a higher degree of pain. In addition to the actual malignancies, pets can experience pain associated with cancer treatments, such as surgery, radiation therapy, or chemotherapy. Untreated pain decreases the pet's quality of life and also can prolong recovery from the illness or treatment; it can also affect the owner emotionally.

Cancer cachexia (a term referring to progressive severe weight loss) is frequently observed in pets with cancer. Pets with cancer lose weight for a number of reasons: one of those reasons is lack of appetite, and another of those reasons is cancer-induced altered metabolism. Some of the causes for decreased appetite are related to the cancer itself (for example, tumors may physically interfere with food chewing, swallowing, and digestion processes, depending on their size and location) and some may be related to the side effects of cancer treatment (for example, some chemotherapy drugs cause nausea and vomiting, and radiation therapy can cause mouth inflammation).

Strategies for treatment of cancer in pets, such as cats and dogs, are generally similar to strategies employed for treatment of cancer in humans. In general, the basic strategies are one or more of surgery, radiation, and chemotherapy. Many of the chemotherapeutic approaches employed for treatment of cancer in humans have been employed or evaluated in pets, such as the use of monoclonal antibodies, targeted therapy, cancer vaccines, the simultaneous use of multiple therapeutic agents, and other approaches.

Therefore, there is a definite need for improved veterinary treatment of cancer. There is a particular need for agents that can be administered to treat a wide variety of malignancies and that are well tolerated without causing significant side effects.

SUMMARY OF THE INVENTION

The veterinary use of the anticancer agents dianhydrogalactitol (DAG), diacetyldianhydrogalactitol (DADAG), and dibromodulcitol (DBD) meets the need for an improved veterinary treatment of cancer.

Accordingly, one aspect of the present invention is a method for treating a malignancy in a companion animal comprising the step of administering a therapeutically effective quantity of a therapeutic agent selected from the group consisting of dianhydrogalactitol, a derivative of dianhydrogalactitol, diacetyldianhydrogalactitol, a derivative of diacetyldianhydrogalactitol, dibromodulcitol, and a derivative of dibromodulcitol, to a companion animal in need thereof. Typically, the therapeutic agent is selected from the group consisting of dianhydrogalactitol, diacetyldianhydrogalactitol, and dibromodulcitol.

Typically, the malignancy is selected from the group consisting of a hematologic malignancy, a malignancy of the brain, and an osteosarcoma.

Typically, the companion animal is selected from the group consisting of a dog, a cat, and a horse. Methods of the present invention are particularly useful in treating dogs and cats.

Typically, the therapeutic agent is administered by a route of administration selected from the group consisting of intravenous, parenteral, intraperitoneal, intravenous, transcutaneous, subcutaneous, intramuscular, intraurethral, and oral administration. Preferably, the therapeutic agent is administered by a route of administration selected from the group consisting of oral, intravenous, and intraperitoneal administration.

Typically, when the therapeutic agent is selected from the group consisting of dianhydrogalactitol, diacetyldianhydrogalactitol, and dibromodulcitol, the initial dosage of the therapeutic agent is about 5 to 40 mg/m$^2$, once or twice/week, every 4-6 weeks.

In one alternative, the therapeutic agent is administered in a pharmaceutical composition.

Yet another aspect of the present invention is a method to improve the efficacy and/or reduce the side effects of the administration of a therapeutic agent selected from the group consisting of dianhydrogalactitol, a derivative of dianhydrogalactitol, diacetyldianhydrogalactitol, a derivative of diacetyldianhydrogalactitol, dibromodulcitol, and a derivative of dibromodulcitol to a veterinary subject, the method comprising the steps of:

(1) identifying at least one factor or parameter associated with the efficacy and/or occurrence of side effects of the administration of the therapeutic agent to the veterinary subject; and (2) modifying the factor or parameter to improve the efficacy and/or reduce the side effects of the administration of the therapeutic agent to the veterinary subject.

Typically, in this method, the therapeutic agent is selected from the group consisting of dianhydrogalactitol, diacetyldianhydrogalactitol, and dibromodulcitol.

Typically, in this method, the factor or parameter is selected from the group consisting of:

(1) dose modification;
(2) route of administration;
(3) schedule of administration;
(4) veterinary subject selection;
(5) analysis of veterinary subject or disease phenotype;
(6) analysis of veterinary subject or disease genotype;
(7) pre/post treatment preparation;
(8) toxicity management;
(9) pharmacokinetic/pharmacodynamic monitoring;
(10) drug combination;
(11) chemosensitization;
(12) chemopotentiation;
(13) post-treatment management;
(14) the use of a herbal medication created either synthetically or through extraction;
(15) a bulk drug product improvement;
(16) use of a diluent;
(17) use of a solvent system;
(18) use of an excipient;
(19) use of a dosage form optimized for veterinary use;
(20) use of dosage kits and packaging;
(21) use of a drug delivery system.
(22) use of a drug conjugate form;
(23) use of a compound analog;
(24) use of a prodrug system;
(25) use of a multiple drug system;
(26) use of biotherapeutic enhancement;
(27) use of biotherapeutic resistance modulation;
(28) use of radiation therapy enhancement;
(29) use of novel mechanisms of action; and
(30) use of selective target cell population therapeutics.

Yet another aspect of the present invention is a composition to improve the efficacy and/or reduce the side effects of a veterinary application of drug therapy comprising an alternative selected from the group consisting of:

(a) a therapeutically effective quantity of a modified therapeutic agent or a derivative, analog, or prodrug of a therapeutic agent or modified therapeutic agent, wherein the modified therapeutic agent or the derivative, analog or prodrug of the therapeutic agent or modified therapeutic agent possesses increased therapeutic efficacy or reduced side effects as compared with an unmodified therapeutic agent;

(b) a composition comprising:
  (i) a therapeutically effective quantity of a therapeutic agent, a modified therapeutic agent or a derivative, analog, or prodrug of a therapeutic agent or modified therapeutic agent; and
  (ii) at least one additional therapeutic agent, therapeutic agent subject to chemosensitization, therapeutic agent subject to chemopotentiation, diluent, excipient, solvent system, or drug delivery system, wherein the composition possesses increased therapeutic efficacy or reduced side effects as compared with an unmodified therapeutic agent;

(c) a therapeutically effective quantity of a therapeutic agent, a modified therapeutic agent, or a derivative, analog, or prodrug of a therapeutic agent or modified therapeutic agent that is incorporated into a dosage form, wherein the therapeutic agent, the modified therapeutic agent, or the derivative, analog, or prodrug of a therapeutic agent or modified therapeutic agent incorporated into the dosage form possesses increased therapeutic efficacy or reduced side effects as compared with an unmodified therapeutic agent;

(d) a therapeutically effective quantity of a therapeutic agent, a modified therapeutic agent, or a derivative, analog, or prodrug of a therapeutic agent or modified therapeutic agent that is incorporated into a dosage kit and packaging, wherein the therapeutic agent, the modified therapeutic agent, or the derivative, analog, or prodrug of a therapeutic agent or modified therapeutic agent incorporated into the dosage kit and packaging possesses increased therapeutic efficacy or reduced side effects as compared with an unmodified therapeutic agent; and (e) a therapeutically effective quantity of a therapeutic agent, a modified therapeutic agent, or a derivative, analog, or prodrug of a therapeutic agent or modified therapeutic agent that is subjected to a bulk drug product improvement, wherein the therapeutic agent, the modified therapeutic agent, or the derivative, analog, or prodrug of a therapeutic agent or modified therapeutic agent subject to the bulk drug product improvement possesses increased therapeutic efficacy or reduced side effects as compared with an unmodified therapeutic agent;

wherein the therapeutic agent is selected from the group consisting of dianhydrogalactitol, diacetyldianhydrogalactitol, and dibromodulcitol;

wherein the modified therapeutic agent is a modified form of a therapeutic agent selected from the group consisting of dianhydrogalactitol, diacetyldianhydrogalactitol, and dibromodulcitol; and wherein the derivative, analog, or prodrug of a therapeutic agent or modified therapeutic agent is a derivative, analog, or prodrug of a therapeutic agent selected from the group consisting of dianhydrogalactitol, diacetyldianhydrogalactitol, and dibromodulcitol, and a modified form of dianhydrogalactitol, diacetyldianhydrogalactitol, or dibromodulcitol.

BRIEF DESCRIPTION OF THE DRAWINGS

The following invention will become better understood with reference to the specification, appended claims, and accompanying drawings, where:

DETAILED DESCRIPTION OF THE INVENTION

Figure 1C:
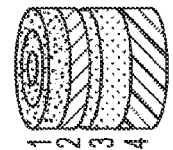
FIG. 1 is a schematic demonstration of examples of structural and numerical chromosome aberrations. Panel (A) shows single homologues of two example chromosomes; on the left the larger submetacentric chromosome has been divided in regions A and B on the p-arm and regions C—H on the q-arm; on the right the smaller metacentric chromosome has regions 1 and 2 comprising the p-arm and regions 3 and 4 comprising the q-arm. Panels (B) and (C) show balanced chromosome aberrations in which the organization of the segments has altered but their copy number has not changed; in B a reciprocal translocation between the two chromosomes has resulted in two new derivative chromosomes, in which the q arms have been exchanged; in C a paracentric inversion in the q arm of the larger chromosome has resulted in a change of segment order. These changes would go undetected in comparative hybridization analysis and would require cytogenetic evaluation to identify these changes. Panels D, E and F show structural changes that are associated with gain or loss of chromosomal segments of the larger chromosome; D shows deletion of region E, E shows a pericentric inversion with loss of region A, F shows a duplication of region E. All three of these aberrations change the DNA content of the cell and would be readily detected using CGH analysis. All three would also be visualized using molecular cytogenetic evaluation with suitable probes.
Figure 1C:
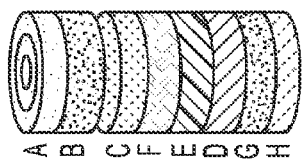
Figure 1F:
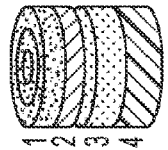
Figure 1F:
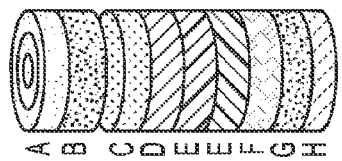
Figure 1B:
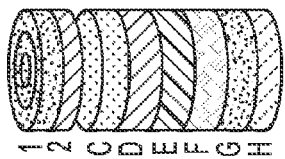
Figure 1B:
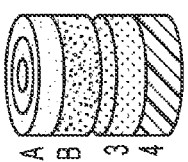
Figure 1E:
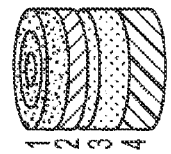
Figure 1E:
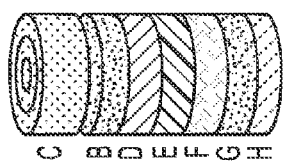
Figure 1A:
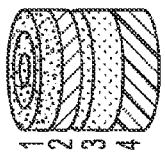
Figure 1A:
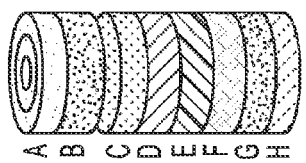
Figure 1D:
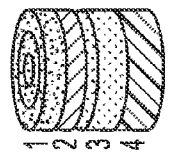
Figure 1D:
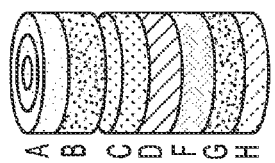

The veterinary use of the anticancer agents dianhydrogalactitol (DAG), diacetyldianhydrogalactitol (DADAG), and dibromodulcitol (DBD) meets the need for an improved veterinary treatment of cancer. These agents are well tolerated, can treat a wide variety of malignancies, and are substantially free from side effects.

The structure of dianhydrogalactitol is shown in Formula (I), below.

(I)

Also within the scope of the invention are derivatives of dianhydrogalactitol that, for example, have the hydrogen of the hydroxyl groups replaced with lower alkyl, have the hydrogen attached to the epoxide ring replaced with lower alkyl, or have the methyl groups attached to the same carbons that bear the hydroxyl groups replaced with lower alkyl or substituted with, for example, halo groups.

The structure of diacetyldianhydrogalactitol is shown in Formula (II), below.

(II)

Also within the scope of the invention are derivatives of diacetyldianhydrogalactitol that, for example, have the methyl groups that are part of the acetyl moieties replaced with lower alkyl, have the hydrogen attached to the epoxide ring replaced with lower alkyl, or have the methyl groups attached to the same carbons that bear the acetyl groups replaced with lower alkyl or substituted with, for example, halo groups.

The structure of dibromodulcitol is shown in Formula (III), below. Dibromodulcitol can be produced by the reaction of dulcitol with hydrobromic acid at elevated temperatures, followed by crystallization of the dibromodulcitol. Some of the properties of dibromodulcitol are described in N. E. Mischler et al., "Dibromoducitol," *Cancer Treat. Rev.* 6: 191-204 (1979), incorporated herein by this reference. In particular, dibromodulcitol, as an α, ω-dibrominated hexitol, dibromodulcitol shares many of the biochemical and biological properties of similar drugs such as dibromomannitol and mannitol myleran. Activation of dibromodulcitol to the diepoxide dianhydrogalactitol occurs in vivo, and dianhydrogalactitol may represent a major active form of the drug; this means that dibromogalactitol has many of the properties of a prodrug. Absorption of dibromodulcitol by the oral route is rapid and fairly complete. Dibromodulcitol has known activity in melanoma, breast lymphoma (both Hodgkins and non-Hodgkins), colorectal cancer, acute lymphoblastic leukemia and has been shown to lower the incidence of central nervous system leukemia, non-small cell lung cancer, cervical carcinoma, bladder carcinoma, and metastatic hemangiopericytoma.

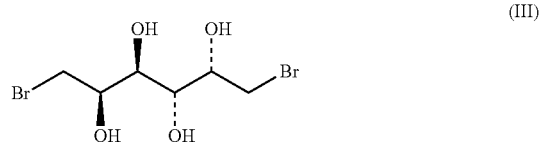 [SMILES: O[C@H]([C@H](O)[C@@H](O)CBr)[C@H](O)CBr]

(III)

Also within the scope of the invention are derivatives of dibromodulcitol that, for example, have one or more hydrogens of the hydroxyl groups replaced with lower alkyl, or have one or both of the bromo groups replaced with another halo group such as chloro or fluoro.

As with humans, our primary companion animals, dogs and cats, also now benefit from advances in health care and are tending to live longer lives, with a similar elevation in the number of pets that are diagnosed with malignancy.

While the actual cost of treating cancer occurring in companion animals is unknown, with the millions of animals being treated each year the cost is estimated to be several billion dollars per year in the United States alone, with comparable costs in other countries, such as those in Europe, where companion animal ownership is widespread.

Although we now know that many cancers in humans and companion animals are highly comparable diseases, the approach to treating those cancers historically has been far from parallel. In human medicine it is accepted that the driving aim of cancer treatment is to "cure" the patient. There are three general approaches to treating cancer in humans—surgery, radiation therapy, and chemotherapy. In treating human patients a combination of these three approaches is often used as part of a highly aggressively regime to keep patients alive as long as possible. In veterinary medicine there is a general acceptance that euthanasia is one possible outcome. As such, many animals are still not treated for their cancer and many of those that are treated may receive treatments that are less aggressive and more palliative than would be the case for human cancers in a comparable stage. However, with all three of the treatment approaches used in human oncology now available to veterinary oncology, the field is presented with new opportunities to embrace new options other than euthanasia. Though we may be a long way from curing cancers, there is optimism that we will be able to treat cancers in pets with improved therapies that not only extend life but also maintain a high quality of life.

Cancer refers to a myriad of diseases and for decades it has been through the eyes of the experienced cancer pathologist that the "type" of cancer has been determined. Subclassification of malignancies provides more opportunity to correlate the tumors of individual patients with their clinical and biologic behavior. Conventional histological approaches advanced the field for many years and the application of immunohistocytochemistry to determine the presence of specific cell surface markers is still used widely to subdivide tumors. This approach is applied both in human oncology and in veterinary oncology.

In veterinary medicine, the lack of advanced molecular genomic tools specific to non-human species has hampered our abilities to take full advantage of this exciting and promising new field. The vision of leaders in genomics recognized the power of using comparative analysis of other animals to benefit our understanding of the human genome. This led to a series of non-human genomes entering the pipeline for full sequencing. In July 2005, the release of a publicly accessible annotated genome assembly of the domestic dog (K. Lindblad-Toh et al., "Genome Sequence, Comparative Analysis and Haplotype Structure of the Domestic Dog," *Nature* 438: 803-819 (2005), incorporated herein by this reference) and subsequently a draft sequence of the domestic cat (J. U. Pontius et al., "Initial Sequence and Comparative Analysis of the Cat Genome," *Genome Res.* 17: 1675-1689 (2007), incorporated herein by this reference; S. J. O'Brien et al., "State of Cat Genomics," *Trends Genet.* 24: 268-279 (2008), incorporated herein by this reference) changed the landscape for canine and feline cancer research. With the release of the horse genome imminent, the future of companion animal veterinary oncology is now presented with a series of exciting new opportunities that were previously considered well beyond its reach.

Recent research has enabled the use of genomic technologies to veterinary oncology. One aspect of this is the use of molecular cytogenetics at both the pre-genome assembly and post-genome assembly stages. Just as the pathologist gains more detailed visual clues about the cells comprising a tissue section by rotating the objective turret of his/her microscope to a higher powered lens, so the molecular biologist seeks to use higher resolution molecular tools and approaches to hone in on the genome, from the chromosome to the DNA sequence of the gene. Prior to the availability of a genome sequence for any species, investigations of genome organization in cancers relied primarily on the use of molecular cytogenetics, while determination of specific mutations at the DNA level relied on targeted use of the polymerase chain reaction (PCR). With complete genome sequences now available for dog, cat and horse, we are presented with the tools needed to ask very specific questions about genomes and cancer.

It is widely accepted that malignant transformation requires the accumulation of genetic alterations or lesions. At the subcellular level, many of these changes are evident as alterations to chromosome number and/or structure. The development of molecular cytogenetics, using fluorescence in situ hybridization (FISH) technology, has played a significant role in our understanding of cancer biology by providing a means for "interrogating" tumor cells for such gross karyotypic changes. The field of molecular cytogenetics provides a highly visual approach to identify chromosome aberrations that are recurrent and thus associated with initiation/progression of malignancy, versus those that are random and thus a result of the chaotic genome organization associated with tumor cells. Many forms of human cancer are so closely associated with specific chromosome aberrations that the aberrations are regarded now as diagnostic for the cancer. Some chromosome aberrations result in the gain or loss of chromosomal material (numerical changes), whilst others result in a reorganization of chromosomal material (structural changes) with either a net change in DNA copy number (imbalanced rearrangements) or no net change in DNA copy number (balanced aberrations) (FIG. 1). While numerical changes alter the copy number of genes in the genome, structural changes frequently bring together genes that have been spatially separated in the genome for millions of years. The interaction between these new neighbors in the cancer genome often leads to the altered regulation of genes and/or the generation of new gene products that may act to drive the cell to form a cancer; this altered regulation and the generation of such new gene products is also associated with the dedifferentiation that is characteristic of many tumor cells. Knowledge of such gene products provides an opportunity to develop new therapies for treatment of cancers, using the hypothesis that if we are able to identify the biological drivers of a cancer we may be able to block their effects and so inhibit cancer progression. In addition, for many human cancers there is a correlation between the presence of certain genomic aberrations and the clinical outcome of the tumor and/or the tumor's response to therapy. For this reason many chromosome aberrations are of prognostic value and this information may be used by clinicians to determine the most appropriate therapy and likely survival times (J. J. Oudejans et al., "Identification of Genes Putatively Involved in the Pathogenesis of Diffuse Large B-Cell Lymphomas by Integrative Genomics," *Genes Chromosomes Cancer* 48: 250-260 (2009), incorporated herein by this reference). Specifically, FIG. 1 is a schematic demonstration of examples of structural and numerical chromosome aberrations. Panel (A) shows single homologues of two example chromosomes; on the left the larger submetacentric chromosome has been divided in regions A and B on the p-arm and regions C—H on the q-arm; on the right the smaller metacentric chromosome has regions 1 and 2 comprising the p-arm and regions 3 and 4 comprising the q-arm. Panels (B) and (C) show balanced chromosome aberrations in which the organization of the segments has altered but their copy number has not changed; in B a reciprocal translocation between the two chromosomes has resulted in two new derivative chromosomes, in which the q arms have been exchanged; in C a paracentric inversion in the q arm of the larger chromosome has resulted in a change of segment order. These changes would go undetected in comparative hybridization analysis and would require cytogenetic evaluation to identify these changes. Panels D, E and F show structural changes that are associated with gain or loss of chromosomal segments of the larger chromosome; D shows deletion of region E, E shows a pericentric inversion with loss of region A, F shows a duplication of region E. All three of these aberrations change the DNA content of the cell and would be readily detected using CGH analysis. All three would also be visualized using molecular cytogenetic evaluation with suitable probes.

Many examples are known of evolutionarily conserved genomic changes in cancers. Perhaps the most widely investigated chromosome aberration associated with cancers in people is the Philadelphia chromosome, first described almost half a century ago in patients with chronic myelogenous leukemia (CML) (P. C. Nowell & D. A. Hungerford, "A Minute Chromosome in Human Chronic Granulocytic Leukemia," *Science* 132: 1497 (1960), incorporated herein by this reference). This aberrant human chromosome (HSA) is the result of a translocation event that brings together the c-abl oncogene [located at HSA 9q34 (ABL locus)] and the breakpoint cluster region (BCR) [located at HSA 22q11] to form a derivative human chromosome 22, technically described as t(9; 22)(q34; q11) and referred to as the Philadelphia (Ph) chromosome (J. D. Rowley, "Letter: A New Consistent Chromosomal Abnormality in Chronic Myelogenous Leukemia Identified by Quinacrine Fluorescence and Giemsa Staining," *Nature* 243: 290-293 (1973), incorporated herein by this reference). The juxtaposition of BCR and ABL is considered a hallmark feature of CML, reported in over 95% of CML patients (R. Kurzrock et al., "Philadelphia Chromosome-Positive Leukemias: From Basic Mechanisms to Molecular Genetics," *Ann. Intern. Med.* 138: 819-830 (2003)). The biological consequence of the generation of this fusion is elevation of tyrosine kinase activity, with the consequential proliferation of white blood cells. The identification that a compound, STI571 (imatinib mesylate) could act as an antagonist to this fusion protein (bcr-abl tyrosine kinase) and prevent blast crisis (M. J. Mauro & B. J. Druker, "Chronic Myelogenous Leukemia," *Curr. Opin. Oncol.* 13: 3-7 (2003), incorporated herein by this reference; M. J. Mauro et al., "ST1571, a Tyrosine Kinase Inhibitor for the Treatment of Chronic Myelogenous Leukemia: Validating the Promise of Molecularly Targeted Therapy," *Cancer Chemother. Pharmacol.* 48 (Suppl. 1): S77-S78 (2001), incorporated herein by this reference led to clinical trials and the development of Gleevec® that (with some exceptions) is now generally considered standard of care for patients shown to present with the Philadelphia chromosome. In May 2001, the FDA approved Gleevec for first-line treatment of CML and over the following two years almost 90% of patients were free of disease worsening, with an estimated overall survival rate of 91% and a cytogenetic response in up to 60% of patients (H. M. Kantarjian & M. Talpaz, "Imatinib Mesylate: Clinical Results in Philadelphia Chromosome-Positive Leukemias," *Semin. Oncol.* 28 (5 Suppl. 17): 9-18 2001), incorporated herein by this reference; J. C. Hernandez-Boluda et al., "Imatinib Mesylate (Gleevec, Glivec): A New Therapy for Chronic Myeloid Leukemia and Other Malignancies," *Drugs Today* 38: 601-613 (2002), incorporated herein by this reference). Cytogenetic response remains an important surrogate marker of survival in human CML patients (M. W. Deininger, "Cytogenetic Studies in Patients on Imatinib," *Semin. Hematol.* 40 (2 Suppl. 2): 50-55 (2003), incorporated herein by this reference; G. Rosti et al., "The Cytogenetic Response as a Surrogate Marker of Survival," *Semin. Hematol.* 40 (2 Suppl. 2): 56-61 (2003), incorporated herein by this reference).

Figure 2A:
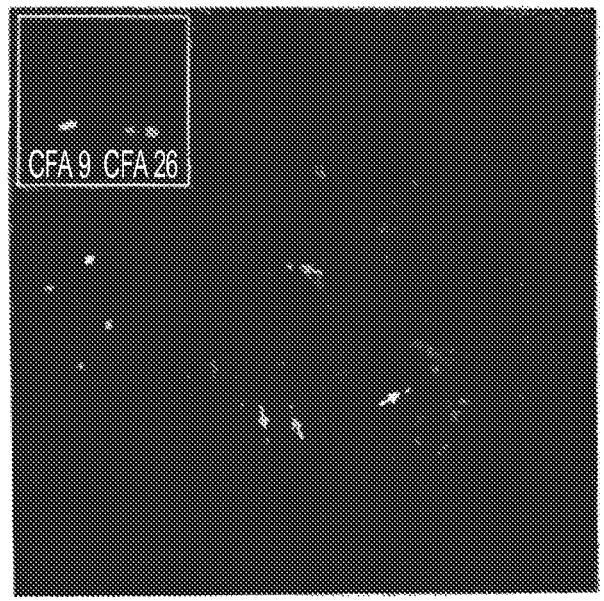
FIG. 2 shows identification of the "Raleigh" chromosomes in dogs diagnosed with chronic myelogenous leukemia. Panel (A) shows metaphase preparation and interphase nucleus from a clinically healthy dog to which canine bacterial artificial chromosome (BAC) clones representing the genes ABL (yellow signal) and BCR (green signal) showing the localization of these loci to CFA 9 and 26, respectively (see inset). Panel (B) shows hybridization of the same BCR and ABL BAC clones to a metaphase preparation and interphase nuclei derived from a CML patient. In the metaphase spread, while one copy each of CFA 9 and 26 appear normal (lower right) the presence of a derivative chromosome showing co-localization of yellow and green signal (inset) indicates the presence of the "Raleigh" chromosome. Similarly, juxtaposition of one green and one yellow signal in each of the two interphase nuclei conform this translocation event.
Figure 2B:
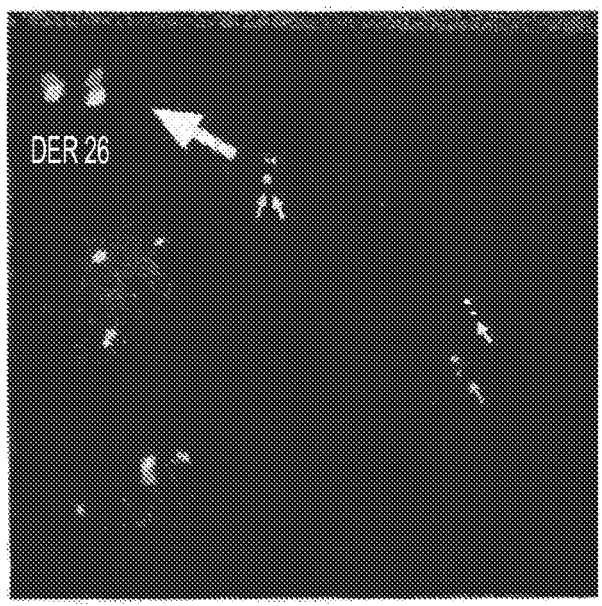

While very rare in veterinary species CML has been reported in dogs, all of which had a poor prognosis (J. M. Tarrant et al., "Diagnosis of Chronic Myelogenous Leukemia in a Dog Using Morphologic, Cytochemical, and Flow Cytometric Techniques," *Vet. Clin. Pathol.* 30: 19-24 (2001), incorporated herein by this reference; C. E. Leifer et al., "Chronic Myelogenous Leukemia in the Dog," *J. Am. Vet. Med. Assoc.* 183: 686-689 (1983), incorporated herein by this reference; L. Pollet et al., "Blastic Crisis in Chronic Myelogenous Leukemia in a Dog," *J. Small Anim. Pract.* 19: 469-475 (1978), incorporated herein by this reference; M. Breen & J. F. Modiano, "Evolutionarily Conserved Cytogenetic Changes in Hematological Malignancies of Dogs and Humans: Man and His Best Friend Share More Than Companionship," *Chromosome Res.* 16: 145-154 (2008), incorporated herein by this reference). A recent study of canine CML showed that dogs diagnosed with CML also presented with a functional active BCR-ABL translocation, known as the Raleigh chromosome, which is analogous to the Philadelphia chromosome in humans (FIG. 2). These data suggest that, cost aside, treatment with Gleevec (using careful monitoring for liver toxicity) could be an option for therapy of canine CML. This study resulted in the first molecular cytogenetic test for the presence of a clinically significant genomic alteration in a veterinary cancer and has since been used to identify the Raleigh chromosome in a further 10 dogs presenting with CML. In the same study, the presence of RB1 deletions in canine patients presenting with chronic lymphocytic leukemias and MYC-IgH translocations in canine patients diagnosed with Burkitt lymphoma were also reported. These findings reinforce the concept that as mammals, humans and dogs may be considered temporally separated, differential organizations of the same collection of ancestrally related genes. Since we have shown that genetic lesions associated with human cancers may similarly occur in cancers of veterinary species, therapies developed for malignancies with specific cytogenetic signatures in human cancers may become applicable to provide improved treatments for cancers in our pet dogs and cats. This of course assumes that we are able to define the evolutionarily conserved signatures in our pets and that the pharmacologic effects are considered efficacious. There is little doubt that with the new genomics resource now available to the veterinary biomedical researches, similar associations will be discovered for a variety of animal cancers and that cytogenetic screening of cancers in our pets could become common practice in veterinary oncology. Specifically, FIG. 2 shows shows identification of the "Raleigh" chromosomes in dogs diagnosed with chronic myelogenous leukemia. Panel (A) shows metaphase preparation and interphase nucleus from a clinically healthy dog to which canine bacterial artificial chromosome (BAC) clones representing the genes ABL (yellow signal) and BCR (green signal) showing the localization of these loci to CFA 9 and 26, respectively (see inset). Panel (B) shows hybridization of the same BCR and ABL BAC clones to a metaphase preparation and interphase nuclei derived from a CML patient. In the metaphase spread, while one copy each of CFA 9 and 26 appear normal (lower right) the presence of a derivative chromosome showing co-localization of yellow and green signal (inset) indicates the presence of the "Raleigh" chromosome. Similarly, juxtaposition of one green and one yellow signal in each of the two interphase nuclei conform this translocation event.

Another aspect of recent research that has become useful in veterinary oncology is the use of microarray technology. While conventional and molecular cytogenetics are able to reveal and characterize gross genomic alterations in cancers, the process is limited by the resolution of fluorescence microscopy. The determination of genome sequences for a variety of veterinary species has allowed for the development of new microarray based technologies, that facilitate whole genome, or gene targeted, profiling to be performed at a considerably higher resolution and throughput. The major microarray platforms available for veterinary oncology were initially genomic and cDNA microarrays generated by depositing DNA fragments onto a glass or silicon surface and then binding the sequences to the surface. These arrays generally comprise several hundred to several thousand spots, or features, according to their intended use. More recently high-density oligonucleotide arrays, where short DNA sequences are synthesized directly on the surface of the chip have allowed tens to hundreds of thousand of features to be represented on the array and thus increase resolution substantially. Depending on the design, either of these types of microarray may be used to establish DNA copy number variation and gene expression levels, while the latter may be designed specifically to define single base pair changes (single nucleotide polymorphisms, SNPs) at many thousand of points throughout the genome.

Figures 3A, 3B, 3C:
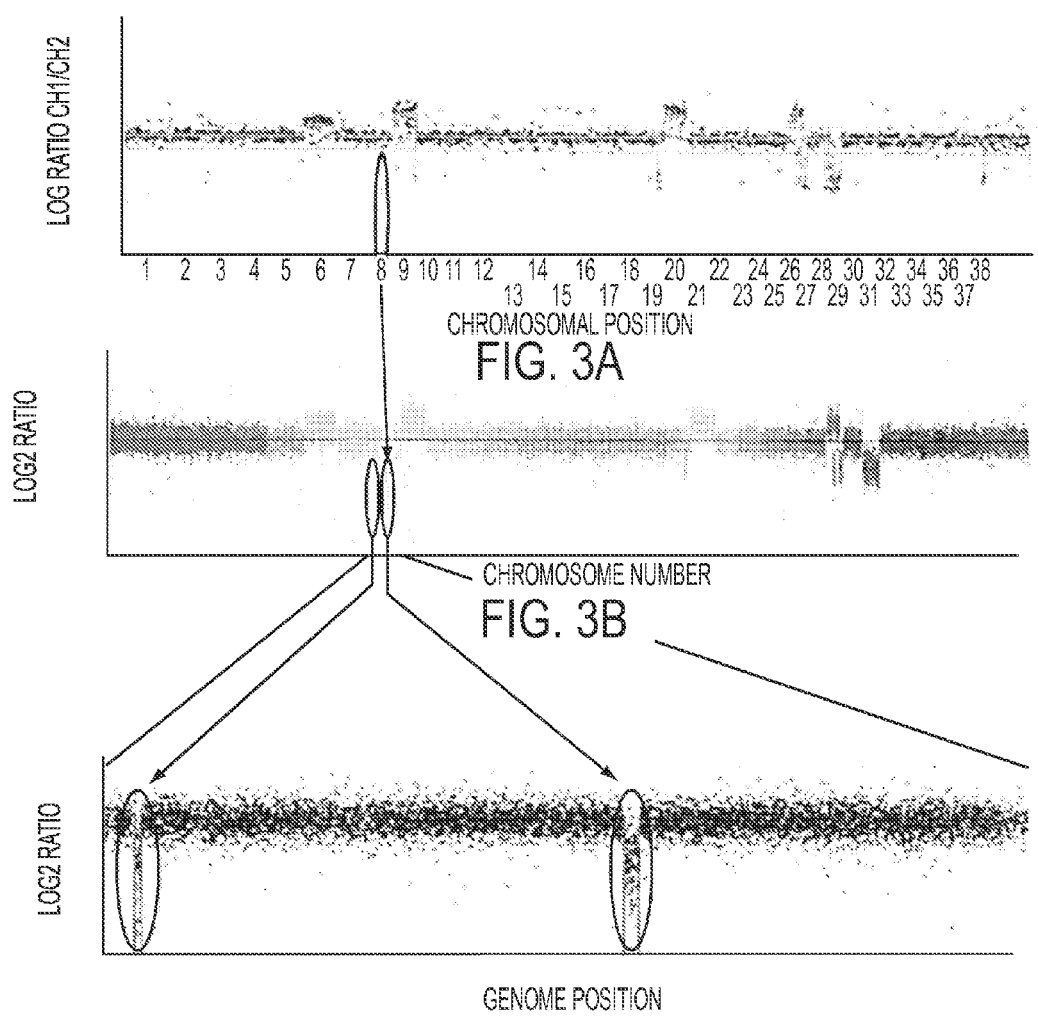
FIG. 3 shows advances in resolution of DNA copy number variation using array based comparative genomic hybridization (aCGH). Panel (A) shows aCGH data of a canine tumor sample using a 1 Mb BAC array [24] indicates genome wide DNA copy number variation of 2,200 canine BAC clones. There is indication of copy number increase for regions of dog chromosomes (CFA) 6, 9, 21 and 26 and evident of copy number decrease for segments of CFA 8, 19, 26 and 28. There is evidence of a homozygous deletion of a single BAC clone in the distal half of CFA 8 (circled). Panel (B) shows genome wide aCGH analysis of the same case on a high resolution oligonucleotide array, assessing copy number at 385,000 points in the canine genome and with an effective resolution of 50 Kb. It is evident that the overall copy number aberrations visible in panel (B) are grossly comparable to those in panel (A) although additional copy number changes are evident that lay between the loci assessed on the BAC array. Panel (C) shows aCGH data specifically from CFA 8 of panel (B); when the copy number data are evaluated at this resolution it is evident that the copy number aberration at the distal end of the chromosome may now be further refine to a region that spans fewer than 1.5 Mb between 45 Mb and 46.5 Mb (red lines). Interestingly, this higher resolution platform also identified a smaller deletion of less than 1 Mb at the proximal end of CFA8 within the region ~5.5 Mb-6.0 Mb. This deletion lay between BAC clones on the 1 Mb array and so was not detected in panel (A).

Yet another recently developed analytical method that can be applied to veterinary oncology is comparative genomic hybridization (CGH). This procedure allows for genome wide evaluation of DNA copy number aberrations at a much higher throughput and resolution than is possible with conventional approaches, thus allowing a more accurate and faster rate of data accumulation. The emergence of complete genome assemblies enables the generation of genome integrated molecular cytogenetic resources. For example, a recent study by Thomas et al. (R. Thomas et al., "A Genome Assembly-Integrated Dog 1 Mb BAC Microarray: A Cytogenetic Resource for Canine Studies and Comparative Genomic Analysis," *Cytogenet. Genome Res.* 122: 110-122 (2008), incorporated herein by this reference) reported on the generation of over 2,000 canine bacterial artificial chromosome (BAC) clones, each selected from the canine genome assembly at approx 1 Mb intervals and each cytogenetically verified by FISH analysis. Using this genome assembly integrated collection of clones, Thomas et al. generated a genomic microarray that was validated for use in array based comparative genomic hybridization analysis (aCGH) of canine tumor DNA samples. This approach has already been used to analyze several types of canine cancer (Thomas et al., supra; W. C. Kisseberth et al., "A Novel Canine Lymphoma Cell Line: A Translational and Comparative Model for Lymphoma Research," *Leuk. Res.* 31: 1709-1720 (2007), incorporated herein by this reference; R. Thomas et al., "Influence of Genetic Background on Tumor Karyotypes: Evidence for Breed-Associated Cytogenetic Aberrations in Canine Appendicular Osteosarcoma," *Chromosome Res.* 17: 365-377 (2009), incorporated herein by this reference; T. Y. Lin et al., "Generation and Characterization of Novel Canine Malignant Mast Cell Line CL1," *Vet. Immunol. Immunopathol.* 127: 114-124 (2009), incorporated herein by this reference). A CGH analysis of human cancers has been refined to determine DNA copy number changes at progressively higher resolutions and the veterinary field is following close behind. High density oligonucleotide arrays that allow scanning of DNA copy number variation in intervals of just a few kilobases of genome sequence are now being used (W. K. Chen et al., "Mapping DNA Structural Variation in Dogs," *Genome Res.* 19: 500-509 (2009), incorporated herein by this reference). An illustration of the rapid change in resolution of CGH in just the past five years is shown in FIG. 3. The use of this approach to define recurrent region of genomes that are subject to aberration is a powerful means to hone in on cancer-associated genes. Specifically, FIG. 3 shows advances in resolution of DNA copy number variation using array based comparative genomic hybridization (aCGH). Panel (A) shows aCGH data of a canine tumor sample using a 1 Mb BAC array [24] indicates genome wide DNA copy number variation of 2,200 canine BAC clones. There is indication of copy number increase for regions of dog chromosomes (CFA) 6, 9, 21 and 26 and evident of copy number decrease for segments of CFA 8, 19, 26 and 28. There is evidence of a homozygous deletion of a single BAC clone in the distal half of CFA 8 (circled). Panel (B) shows genome wide aCGH analysis of the same case on a high resolution oligonucleotide array, assessing copy number at 385,000 points in the canine genome and with an effective resolution of 50 Kb. It is evident that the overall copy number aberrations visible in panel (B) are grossly comparable to those in panel (A) although additional copy number changes are evident that lay between the loci assessed on the BAC array. Panel (C) shows aCGH data specifically from CFA 8 of panel (B); when the copy number data are evaluated at this resolution it is evident that the copy number aberration at the distal end of the chromosome may now be further refine to a region that spans fewer than 1.5 Mb between 45 Mb and 46.5 Mb (red lines). Interestingly, this higher resolution platform also identified a smaller deletion of less than 1 Mb at the proximal end of CFA8 within the region ~5.5 Mb-6.0 Mb. This deletion lay between BAC clones on the 1 Mb array and so was not detected in panel (A).

As in human oncology, developments in the study of gene expression in tumor cells have been applied to veterinary oncology. Another contribution to veterinary cancer research is from the analysis of levels of gene expression. The genetic machinery of the cell tightly regulates the expression of genes, with different cell types having characteristic patterns of gene expression. Using microarrays with highly specific probes, the level of expression of thousands of genes may be assessed simultaneously, a process referred to as gene expression profiling. While there is a variety of fabrication processes for such microarrays, the end result is to generate data that highlights the genes that have become deregulated in the tissue of interest. The study of gene expression profiles in large numbers of human cancers has revealed characteristic patterns of gene expression associated with key clinical features such as the specific subtype of a malignancy, the response to a particular therapy, the duration of remission, and anticipated survival. In the dog, gene expression profiling has been used to reveal genes associated with intracranial malignancies (S. A. Thomson et al., "Microarray Analysis of Differentially Expressed Genes of Primary Tumors in the Canine Central Nervous System," *Vet. Pathol.* 42: 550-558 (2005), incorporated herein by this reference) and to identify that high expression of the membrane-cytoskeleton linker ezrin in dog tumors was associated with early development of metastases (C. Khanna et al., "The Membrane-Cytoskeleton Linker Ezrin Is Necessary for Osteosarcoma Metastasis," *Nat. Med.* 10: 182-186 (2004), incorporated herein by this reference).

Figure 4A:
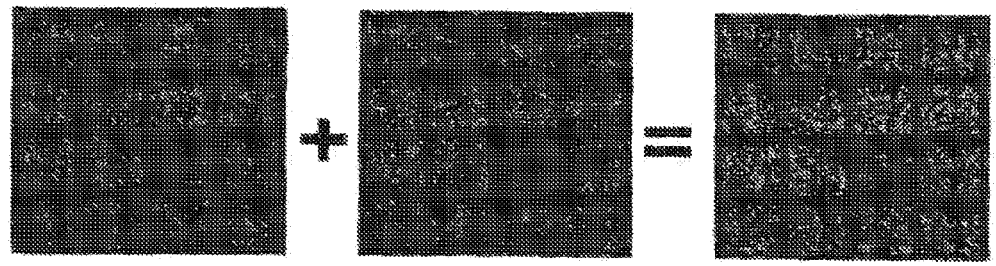
FIG. 4 shows gene expression analysis in canine cancers. Panel (A) shows scan data resulting from the use of a small 3,840 feature cDNA spotted microarray. RNA from two samples were differentially labeled (reference=red; tumor=green) and c-hybridized to the array. Following hybridization the microarray was scanned at 5 µM resolution, acquiring the two color planes. The strength of the hybridization signal on each spot relates the abundance of mRNA population of the corresponding gene. On the right a merged image is shown to visually compare gene expression levels of both samples. Panel (B) is hierarchical cluster analysis of 100 genes identified as showing differential regulation of 60 canine cancer specimens. Each column represents a different patient and each row represents a different gene. Blue represents increased expression and yellow represents reduced expression, relative to non-neoplastic cells. Despite being of the same tumor type, it is evident that these 60 cases of the same histological type have quite distinct gene expression profiles and associating these with response to therapy and survival will lead to more sophisticated cancer patient management.
Figure 4B:
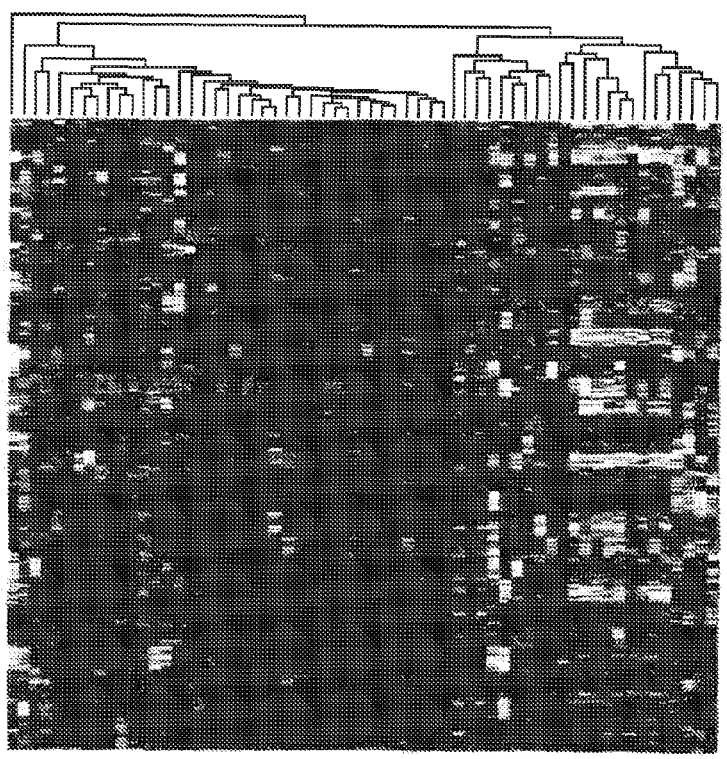

FIG. 4 illustrates how data generated from gene expression profiling are obtained and subsequently compiled to generate clusters of tumors that share commonality determined by the relative expression levels of numerous genes. These gene expression signatures are being investigated for their association with biological behavior of tumors. Specifically, FIG. 4 shows gene expression analysis in canine cancers. Panel (A) shows scan data resulting from the use of a small 3,840 feature cDNA spotted microarray. RNA from two samples were differentially labeled (reference=red; tumor=green) and c-hybridized to the array. Following hybridization the microarray was scanned at 5 μM resolution, acquiring the two color planes. The strength of the hybridization signal on each spot relates the abundance of mRNA population of the corresponding gene. On the right a merged image is shown to visually compare gene expression levels of both samples. Panel (B) is hierarchical cluster analysis of 100 genes identified as showing differential regulation of 60 canine cancer specimens. Each column represents a different patient and each row represents a different gene. Blue represents increased expression and yellow represents reduced expression, relative to non-neoplastic cells. Despite being of the same tumor type, it is evident that these 60 cases of the same histological type have quite distinct gene expression profiles and associating these with response to therapy and survival will lead to more sophisticated cancer patient management.

Yet another procedure now finding application in veterinary oncology is microRNA profiling. While expression profiling is able to determine the level of mRNA transcripts in cell populations, this does not necessarily correspond to the level of protein product that the cells will ultimately generate. MicroRNAs, or miRNAs, are a class of small noncoding RNA species that are known to have critical functions across various biological processes, serving as key regulatory molecules. From a cancer perspective some miRNAs are known to regulate cell proliferation and apoptosis while others have been shown play crucial roles in cancer cell growth. Disturbance of miRNA expression may thus play a role in the initiation and progression of cancers. For example, over expressed miRNAs in cancers, such as miR-17-92, may function as oncogenes and promote cancer development by negatively regulating tumor suppressor genes and/or genes that control cell differentiation or apoptosis (Y. Hayashita et al., "A Polycistronic MicroRNA Cluster, miR-17-92, Is Overexpressed in Human Lung Cancers and Enhances Cell Proliferation," *Cancer Res.* 65: 9628-9632 (2005), incorporated herein by this reference; B. D. Aguda et al., "MicroRNA Regulation of a Cancer Network: Consequences of the Feedback Loops Involving miR-17-92, E2F, and Myc," *Proc. Natl. Acad. Sci. USA* 105: 19678-19683 (2008), incorporated herein by this reference; J. T. Mendell, "MiRiad Roles for the miR-17-92 Cluster in Development and Disease," *Cell* 133: 217-222 (2008), incorporated herein by this reference; S. Takakura et al., "Oncogenic Role of miR-17-92 Cluster in Anaplastic Thyroid Cancer Cells," *Cancer Sci.* 99: 1147-1154 (2008), incorporated herein by this reference). This cluster of miRNAs has been reported also in canine tissues (R. M. Boggs et al., "Identification, Amplification, and Characterization of miR-17-92 from Canine Tissue," *Gene* 404: 25-30 (2007), incorporated herein by this reference). The development of miRNA chips (M. Castoldi et al., "miChip: An Array-Based Method for MicroRNA Expression Profiling Using Locked Nucleic Acid Capture Probes," *Nat. Protoc.* 3: 321-329 (2008), incorporated herein by this reference; A. M. Krichevsky et al., "A MicroRNA Array Reveals Extensive Regulation of MicroRNAs During Brain Development," *RNA* 9: 1274-1281 (2003), incorporated herein by this reference; X. Zhang et al., "An Array-Based Analysis of MicroRNA Expression Comparing Matched Frozen and Formalin-Fixed Paraffin-Embedded Human Tissue Samples," *J. Mol. Diagn.* 10: 513-519 (2008), incorporated herein by this reference) thus provides another means to evaluate simultaneously the role of these key regulators in determining prognosis in cancer patients (C. Jay et al., "miRNA Profiling for Diagnosis and Prognosis of Human Cancer," *DNA Cell Biol.* 26: 293-300 (2007), incorporated herein by this reference). In addition, miRNAs may have the potential for use as therapeutic agents that could be a powerful tool in cancer prevention and treatment.

Another tool that can find application in veterinary oncology is genome wide association studies (GWAS) to define predisposition to cancer. Early cancer detection is affected by the fact that animals do not communicate their ill health until such a time that their physiological stress provides key indicators; loss of weight, loss of appetite, lameness, lack of interest, coughing, or other symptoms detectable by the owners or caretakers of companion animals. While we strive to promote routine health screens and work towards developing means to detect cancers earlier, it is also important to highlight that cancer is a genetic disease and as with other genetic diseases it should be possible to predict which individuals have a genome indicating a cancer predisposition.

It is widely accepted that mapping disease genes in veterinary species is made possible through the development of genomic resources. Cancer is a complex disease process that is associated with numerous genes and so teasing out the major effectors in human populations that present with a high level of locus and phenotypic variation is a challenge. The demographic history of purebred dog breeds has resulted in a genetic structure within dog populations that allows association studies to be performed on considerably smaller cohorts and thus for disease genes to be identified more readily. There are now numerous reports of mapping canine disease genes, both simple and complex, via genome wide genotyping studies (N. B. Sutter & E. A. Ostrander, "Dog Star Rising: The Canine Genetic System," *Nat. Rev. Genet.* 5: 900-910 (2004), incorporated herein by this reference; N. B. Sutter et al., "A Single IGF1 Allele Is a Major Determinant of Small Size in Dogs," *Science* 316: 112-115 (2007), incorporated herein by this reference) illustrating the broader importance of the dog as a comparative model system.

One of the mapping tools for association studies is to consider the haplotypes shared between individuals presenting with the same disease phenotype. Such haplotypes may be scored by a variety of means, with the most informative method being one that assesses variation at the highest density. The densest form of polymorphism in the genome is that which relies on variation at the level of a single base pair. Such changes are called single nucleotide polymorphisms (SNPs). In the domestic dog, the average SNP frequency has been estimated to be 1 every 1,000 bp and researchers are currently identifying the frequency and distribution of SNPs as part of the development of high quality genome assemblies for other veterinary species, including cat and horse. Of great significance to veterinary biomedical research is that association studies is the fact that such a high SNP frequency in the domestic dog means that while association studies in human population may require assessment of 500,000 SNPs, similar studies in purebred dogs require as few as 10,000 SNPs. Genome wide association studies using populations of dogs will likely proceed much faster and at a greatly reduced cost than would be the case using human populations. For diseases with a shared pathogenetic basis in human and dog, gene discovery may thus originate from studies of the dog and then translate to human. Analysis of haplotype in different breeds suggests that a common set of SNPs would be informative for most breeds of dog, but that selection of breeds to be studied is of great importance. Several SNP genome wide association studies to define genes associated with specific phenotypes have already been reported (E. K. Karlsson et al., "Leader of the Pack: Gene Mapping in Dogs and Other Model Organisms," *Nat. Rev. Genet.* 9: 713-725 (2008), incorporated herein by this reference; C. Drogemuller et al., "A Mutation in Hairless Dogs Implicates FOXI3 in Ectodermal Development," *Science* 321: 1462 (2008), incorporated herein by this reference; P. Jones et al., "Single-Nucleotide-Polymorphism-Based Association Mapping of Dog Stereotypes," *Genetics* 179: 1033-1044 (2008), incorporated herein by this reference) and several studies are ongoing to identify genomic regions and ultimately genes associated with a variety of canine cancers. The SNP frequency in the emerging genomes of the cat and horse suggest that both species have a rate the same as the dog. With almost one million SNPs reported in the horse genome and SNP discovery underway for the cat, genome wide association mapping studies will play a key role in investigations of both feline and equine cancers.

Regardless of the approach used to identify cancer associated genes, once identified such genes will be evaluated specifically for their role in the initiation and/or progression of the associated cancers and for their association with response to current and emerging therapies. This work will encourage the development of new therapies for our animal cancer patients, ultimately prolonging the length and quality of life for our pets.

Accordingly, one aspect of the invention is a method of treating a malignancy in a companion animal comprising the step of administering a therapeutically effective quantity of an agent selected from the group consisting of dianhydrogalactitol, a derivative of dianhydrogalactitol, a derivative of dianhydrogalactitol, diacetyldianhydrogalactitol, a derivative of diacetyldianhydrogalactitol, dibromodulcitol, and a derivative of dibromodulcitol. Typically, the agent is selected from the group consisting of dianhydrogalactitol, diacetyldianhydrogalactitol, and dibromodulcitol.

The route of administration, the frequency of administration, and the duration of administration can be chosen by a skilled practitioner, such as a veterinarian with experience in oncology. Such a skilled practitioner will take into account factors such as the breed, age, sex, and weight of the companion animal afflicted with cancer, the metabolic rate of the companion animal, the type of cancer, both in terms of cell type and grade of the cancer, the extent of spread of the cancer, including the existence or non-existence of metastases and their location, if any, the general health of the companion animal, the existence of other diseases or conditions, the response to treatment, and pharmacokinetic factors such as liver and kidney function.

However, for dianhydrogalactitol, diacetyldianhydrogalactitol, or dibromodulcitol, typical initial dosing is about 5 to 40 mg/m$^2$, once or twice/week, every 4-6 weeks for dogs or cats. Dosages can be adjusted depending on the response of the veterinary subject as described below.

Typically, administration is by one or more routes as known in the art, including, but not limited to, intravenous, parenteral, intraperitoneal, intravenous, transcutaneous, subcutaneous, intramuscular, intraurethral, or oral administration. Particularly preferred routes of administration are oral, intravenous, and intraperitoneal administration.

The therapeutic agent as described above (dianhydrogalactitol, a derivative of dianhydrogalactitol, a derivative of dianhydrogalactitol, diacetyldianhydrogalactitol, a derivative of diacetyldianhydrogalactitol, dibromodulcitol, or a derivative of dibromodulcitol) is typically administered in a pharmaceutical composition.

As detailed below, the therapeutic agent as described above can be administered in the form of a prodrug. Techniques for the preparation of prodrugs are described further below.

Formulation of pharmaceutical compositions in tablets, capsules, and topical gels, topical creams or suppositories is well known in the art and is described, for example, in United States Patent Application Publication No. 2004/0023290 by Griffin et al., incorporated herein by this reference.

Formulation of pharmaceutical compositions as patches such as transdermal patches is well known in the art and is described, for example, in U.S. Pat. No. 7,728,042 to Eros et al., incorporated herein by this reference.

When a pharmaceutical composition according to the present invention includes a prodrug, prodrugs and active metabolites of a compound may be identified using routine techniques known in the art. See, e.g., Bertolini et al., J. Med. Chem., 40, 2011-2016 (1997); Shan et al., J. Pharm. Sci., 86 (7), 765-767; Bagshawe, Drug Dev. Res., 34, 220-230 (1995); Bodor, Advances in Drug Res., 13, 224-331 (1984); Bundgaard, Design of Prodrugs (Elsevier Press 1985); Larsen, Design and Application of Prodrugs, Drug Design and Development (Krogsgaard-Larsen et al., eds., Harwood Academic Publishers, 1991); Dear et al., J. Chromatogr. B, 748, 281-293 (2000); Spraul et al., J. Pharmaceutical & Biomedical Analysis, 10, 601-605 (1992); and Prox et al., Xenobiol., 3, 103-112 (1992).

When the pharmacologically active compound in a pharmaceutical composition according to the present invention possesses a sufficiently acidic, a sufficiently basic, or both a sufficiently acidic and a sufficiently basic functional group, these group or groups can accordingly react with any of a number of inorganic or organic bases, and inorganic and organic acids, to form a pharmaceutically acceptable salt. Pharmaceutically acceptable salts can be formed with the following positively-charged ions: sodium, potassium, aluminum, lithium, calcium, magnesium, zinc, ammonium, caffeine, arginine, diethylamine, N-ethylpiperidine, histidine, glucamine, isopropylamine, lysine, morpholine, N-ethylmorpholine, piperazine, piperidine, triethylamine, trimethylamine, ethanolamine, diethanolamine, N-methylglucamine, and tris(hydroxymethyl)aminomethane. Pharmaceutically acceptable salts can be formed with the following negatively-charged ions: chloride, bromide, iodide, carbonate, nitrate, sulfate, bisulfate, phosphate, monohydrogen phosphate, dihydrogen phosphate, metaphosphate, pyrophosphate, formate, acetate, adipate, butyrate, propionate, succinate, glycolate, gluconate, lactate, malate, tartrate, citrate, ascorbate, glucuronate, maleate, fumarate, pyruvate, aspartate, glutamate, benzoate, anthranilate, mesylate, 4'-hydroxybenzoate, phenylacetate, mandelate, embonate (pamoate), methanesulfonate, ethanesulfonate, ethanedisulfonate, benzenesulfonate, pantothenate, 2-hydroxyethanesulfonate, p-toluenesulfonate, sulfanilate, cyclohexylaminosulfonate, camphorate, camphorsulfonate, digluconate, cyclopentanepropionate, dodecylsulfonate, glucoheptanoate, glycerophosphonate, heptanoate, hexanoate, 2-hydroxyethanesulfonate, nicotinate, isonicotinate, 1-naphthalenesulfonate, 2-naphthalenesulfonate, oxalate, palmoate, pectinate, persulfurate, 2-phenylpropionate, picrate, pivalate, thiocyanate, mesylate, undecanoate, stearate, algenate, β-hydroxybutyrate, salicylate, galactarate, galacturonate, caprylate, isobutyrate, malonate, suberate, sebacate, chlorobenzoate, methylbenzoate, dinitrobenzoate, phthalate, phenylacetate, isethionate, lactobionate, p-aminobenzoate, sulfamate, diethylacetate, pimelate, aminosulfonate, acrylate, γ-hydroxybutyrate, and methoxybenzoate. If the pharmacologically active compound has one or more basic functional groups, the desired pharmaceutically acceptable salt may be prepared by any suitable method available in the art, for example, treatment of the free base with a suitable inorganic acid or a suitable organic acid. If the pharmacologically active compound has one or more acidic functional groups, the desired pharmaceutically acceptable salt may be prepared by any suitable method available in the art, for example, treatment of the free acid with an inorganic or organic base.

In the case of agents that are solids, it is understood by those skilled in the art that the inventive compounds and salts may exist in different crystal or polymorphic forms, all of which are intended to be within the scope of the present invention and specified formulas.

The amount of a given pharmacologically active agent that is included in a unit dose of a pharmaceutical composition for administration of a therapeutically active agent as described above will vary depending upon factors such as the particular compound, disease condition and its severity, the identity (e.g., weight) of the subject in need of treatment, but can nevertheless be routinely determined by one skilled in the art. Typically, such pharmaceutical compositions include a therapeutically effective quantity of the pharmacologically active agent and an inert pharmaceutically acceptable carrier or diluent. Typically, these compositions are prepared in unit dosage form appropriate for the chosen route of administration, such as oral administration or parenteral administration. A pharmacologically active agent as described above can be administered in conventional dosage form prepared by combining a therapeutically effective amount of such a pharmacologically active agent as an active ingredient with appropriate pharmaceutical carriers or diluents according to conventional procedures. These procedures may involve mixing, granulating and compressing or dissolving the ingredients as appropriate to the desired preparation. The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of a pharmacologically active agent as described above is dissolved in an aqueous solution of an organic or inorganic acid, such as 0.3 M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, glycerin and the like in concentrations ranging from 0-60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

It will be appreciated that the actual dosages of the agents used in the compositions of this invention will vary according to the particular complex being used, the particular composition formulated, the mode of administration and the particular site, host and disease and/or condition being treated, and the particular drug combination selected. Actual dosage levels of the active ingredients in the pharmaceutical compositions of the present invention can be varied so as to obtain an amount of the active ingredient which is effective to achieve the desired therapeutic response for a particular subject, composition, and mode of administration, without being toxic to the subject. The selected dosage level depends upon a variety of pharmacokinetic factors including the activity of the particular therapeutic agent, the route of administration, the time of administration, the rate of excretion of the particular compound being employed, the severity of the condition, other health considerations affecting the subject, and the status of liver and kidney function of the subject. It also depends on the duration of the treatment, other drugs, compounds and/or materials used in combination with the particular therapeutic agent employed, as well as the age, weight, condition, general health and prior medical history of the subject being treated, and like factors. Methods for determining optimal dosages are described in the art, e.g., Remington: *The Science and Practice of Pharmacy*, Mack Publishing Co., 20$^{th}$ ed., 2000. Optimal dosages for a given set of conditions can be ascertained by those skilled in the art using conventional dosage-determination tests in view of the experimental data for an agent.

The compositions of the invention may be manufactured using techniques generally known for preparing pharmaceutical compositions, e.g., by conventional techniques such as mixing, dissolving, granulating, dragee-making, levitating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations, which can be used pharmaceutically.

Proper formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, solutions, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

Pharmaceutical formulations for parenteral administration can include aqueous solutions or suspensions. Suitable lipophilic solvents or vehicles include fatty oils such as sesame oil or synthetic fatty acid esters, such as ethyl oleate or triglycerides. Aqueous injection suspensions may contain substances which increase the viscosity of the suspension, such as sodium carboxymethyl cellulose, sorbitol, or dextran. Optionally, the suspension may also contain suitable stabilizers or modulators which increase the solubility or dispersibility of the composition to allow for the preparation of highly concentrated solutions, or can contain suspending or dispersing agents. Pharmaceutical preparations for oral use can be obtained by combining the pharmacologically active agent with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating modulators may be added, such as the cross-linked polyvinyl pyrrolidone, agar, or alginic acid or a salt thereof such as sodium alginate.

Other ingredients such as stabilizers, for example, antioxidants such as sodium citrate, ascorbyl palmitate, propyl gallate, reducing agents, ascorbic acid, vitamin E, sodium bisulfite, butylated hydroxytoluene, BHA, acetylcysteine, monothioglycerol, phenyl-α-naphthylamine, or lecithin can be used. Also, chelators such as EDTA can be used. Other ingredients that are conventional in the area of pharmaceutical compositions and formulations, such as lubricants in tablets or pills, coloring agents, or flavoring agents, can be used. Also, conventional pharmaceutical excipients or carriers can be used. The pharmaceutical excipients can include, but are not necessarily limited to, calcium carbonate, calcium phosphate, various sugars or types of starch, cellulose derivatives, gelatin, vegetable oils, polyethylene glycols and physiologically compatible solvents. Other pharmaceutical excipients are well known in the art. Exemplary pharmaceutically acceptable carriers include, but are not limited to, any and/or all of solvents, including aqueous and non-aqueous solvents, dispersion media, coatings, antibacterial and/or antifungal agents, isotonic and/or absorption delaying agents, and/or the like. The use of such media and/or agents for pharmaceutically active substances is well known in the art. Except insofar as any conventional medium, carrier, or agent is incompatible with the active ingredient or ingredients, its use in a composition according to the present invention is contemplated. Supplementary active ingredients can also be incorporated into the compositions, particularly as described above. For administration of any of the compounds used in the present invention, preparations should meet sterility, pyrogenicity, general safety, and purity standards as required by the FDA Office of Biologics Standards or by other regulatory organizations regulating drugs.

For administration intranasally or by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents, which increase the solubility of the compounds to allow for the preparation of highly concentrated solutions.

Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

An exemplary pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

A pharmaceutical composition can be administered by a variety of methods known in the art. The routes and/or modes of administration vary depending upon the desired results. Depending on the route of administration, the pharmacologically active agent may be coated in a material to protect the targeting composition or other therapeutic agent from the action of acids and other compounds that may inactivate the agent. Conventional pharmaceutical practice can be employed to provide suitable formulations or compositions for the administration of such pharmaceutical compositions to subjects. Any appropriate route of administration can be employed, for example, but not limited to, intravenous, parenteral, intraperitoneal, intravenous, transcutaneous, subcutaneous, intramuscular, intraurethral, or oral administration. Depending on the severity of the malignancy or other disease, disorder, or condition to be treated, as well as other conditions affecting the subject to be treated, either systemic or localized delivery of the pharmaceutical composition can be used in the course of treatment. The pharmaceutical composition as described above can be administered together with additional therapeutic agents intended to treat a particular disease or condition, which may be the same disease or condition that the pharmaceutical composition is intended to treat, which may be a related disease or condition, or which even may be an unrelated disease or condition.

Pharmaceutical compositions according to the present invention can be prepared in accordance with methods well known and routinely practiced in the art. See, e.g., Remington: *The Science and Practice of Pharmacy*, Mack Publishing Co., 20$^{th}$ ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions. Formulations for parenteral administration may, for example, contain excipients, sterile water, or saline, polyalkylene glycols such as polyethylene glycol, oils of vegetable origin, or hydrogenated naphthalenes. Biocompatible, biodegradable lactide polymers, lactide/glycolide copolymers, or polyoxyethylene-polyoxypropylene copolymers may be used to control the release of the compounds. Other potentially useful parenteral delivery systems for molecules of the invention include ethylene-vinyl acetate copolymer particles, osmotic pumps, and implantable infusion systems. Formulations for inhalation may contain excipients, for example, lactose, or may be aqueous solutions containing, e.g., polyoxyethylene-9-lauryl ether, glycocholate and deoxycholate, or can be oily solutions for administration or gels.

Pharmaceutical compositions according to the present invention are usually administered to the subjects on multiple occasions. Intervals between single dosages can be weekly, monthly or yearly. Intervals can also be irregular as indicated by therapeutic response or other parameters well known in the art. Alternatively, the pharmaceutical composition can be administered as a sustained release formulation, in which case less frequent administration is required. Dosage and frequency vary depending on the half-life in the subject of the pharmacologically active agent included in a pharmaceutical composition. The dosage and frequency of administration can vary depending on whether the treatment is prophylactic or therapeutic. In prophylactic applications, a relatively low dosage is administered at relatively infrequent intervals over a long period of time. Some subjects may continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the subject can be administered a prophylactic regime.

For the purposes of the present application, treatment can be monitored by observing one or more of the improving symptoms associated with the disease, disorder, or condition being treated, or by observing one or more of the improving clinical parameters associated with the disease, disorder, or condition being treated, as described above.

Sustained-release formulations or controlled-release formulations are well-known in the art. For example, the sustained-release or controlled-release formulation can be (1) an oral matrix sustained-release or controlled-release formulation; (2) an oral multilayered sustained-release or controlled-release tablet formulation; (3) an oral multiparticulate sustained-release or controlled-release formulation; (4) an oral osmotic sustained-release or controlled-release formulation; (5) an oral chewable sustained-release or controlled-release formulation; or (6) a dermal sustained-release or controlled-release patch formulation.

The pharmacokinetic principles of controlled drug delivery are described, for example, in B. M. Silber et al., "Pharmacokinetic/Pharmacodynamic Basis of Controlled Drug Delivery" in *Controlled Drug Delivery: Fundamentals and Applications* (J. R. Robinson & V. H. L. Lee, eds, 2d ed., Marcel Dekker, New York, 1987), ch. 5, pp. 213-251, incorporated herein by this reference.

One of ordinary skill in the art can readily prepare formulations for controlled release or sustained release comprising a pharmacologically active agent according to the present invention by modifying the formulations described above, such as according to principles disclosed in V. H. K. Li et al, "Influence of Drug Properties and Routes of Drug Administration on the Design of Sustained and Controlled Release Systems" in *Controlled Drug Delivery: Fundamentals and Applications* (J. R. Robinson & V. H. L. Lee, eds, 2d ed., Marcel Dekker, New York, 1987), ch. 1, pp. 3-94, incorporated herein by this reference. This process of preparation typically takes into account physicochemical properties of the pharmacologically active agent, such as aqueous solubility, partition coefficient, molecular size, stability, and nonspecific binding to proteins and other biological macromolecules. This process of preparation also takes into account biological factors, such as absorption, distribution, metabolism, duration of action, the possible existence of side effects, and margin of safety, for the pharmacologically active agent. Accordingly, one of ordinary skill in the art could modify the formulations into a formulation having the desirable properties described above for a particular application.

U.S. Pat. No. 6,573,292 by Nardella, U.S. Pat. No. 6,921,722 by Nardella, U.S. Pat. No. 7,314,886 to Chao et al., and U.S. Pat. No. 7,446,122 by Chao et al., which disclose methods of use of various pharmacologically active agents and pharmaceutical compositions in treating a number of diseases and conditions, including cancer, and methods of determining the therapeutic effectiveness of such pharmacologically active agents and pharmaceutical compositions, are all incorporated herein by this reference.

Methods according to the present invention can further incorporate additional adaptations and improvements intended to provide further advantages. For veterinary applications, these adaptations or improvements can accomplish one or more of the following: reduce side effects, reduce pain, increase the therapeutic index of the therapeutically active compound administered, and improve the efficiency of the therapeutically active compound administered in suppressing the growth of tumor cells and/or inducing killing of tumor cells.

In general, such a method is a method to improve the efficacy and/or reduce the side effects of the administration of a therapeutic agent selected from the group consisting of dianhydrogalactitol, a derivative of dianhydrogalactitol, diacetyldianhydrogalactitol, a derivative of diacetyldianhydrogalactitol, dibromodulcitol, and a derivative of dibromodulcitol to a veterinary subject, the method comprising the steps of:

(1) identifying at least one factor or parameter associated with the efficacy and/or occurrence of side effects of the administration of the therapeutic agent to the veterinary subject; and (2) modifying the factor or parameter to improve the efficacy and/or reduce the side effects of the administration of the therapeutic agent to the veterinary subject.

The factor or parameter can be selected from the group consisting of:

(1) dose modification;
(2) route of administration;
(3) schedule of administration;
(4) veterinary subject selection;

(5) analysis of veterinary subject or disease phenotype;
(6) analysis of veterinary subject or disease genotype;
(7) pre/post treatment preparation;
(8) toxicity management;
(9) pharmacokinetic/pharmacodynamic monitoring;
(10) drug combination;
(11) chemosensitization;
(12) chemopotentiation;
(13) post-treatment management;
(14) the use of a herbal medication created either synthetically or through extraction;
(15) a bulk drug product improvement;
(16) use of a diluent;
(17) use of a solvent system;
(18) use of an excipient;
(19) use of a dosage form optimized for veterinary use;
(20) use of dosage kits and packaging;
(21) use of a drug delivery system.
(22) use of a drug conjugate form;
(23) use of a compound analog;
(24) use of a prodrug system;
(25) use of a multiple drug system;
(26) use of biotherapeutic enhancement;
(27) use of biotherapeutic resistance modulation;
(28) use of radiation therapy enhancement;
(29) use of novel mechanisms of action; and
(30) use of selective target cell population therapeutics.

In one alternative, the adaptation or improvement can be made by dose modification. Such dose modification can be made by alterations to the time that the therapeutic agent is administered, the use of dose-modifying agents that control the rate of metabolism of the therapeutic agent, normal tissue protective agents, and other alterations. The dose modification can be a dose modification selected from the group consisting of:
   (a) continuous i.v. infusion for hours to days;
   (b) biweekly administration;
   (c) doses greater than 5 mg/m²/day;
   (d) progressive escalation of dosing from 1 mg/m²/day based on patient tolerance;
   (e) use of caffeine to modulate metabolism;
   (f) use of isonazid to modulate metabolism;
   (g) selected and intermittent boosting of dosage administration;
   (h) administration of single and multiple doses escalating from 5 mg/m²/day via bolus;
   (i) oral dosages of below 30 mg/m²; and
   (j) oral dosages of above 130 mg/m².

In another alternative, the adaptation or improvement can be made by route of administration. For example, the route of administration can involve changing route from oral to intravenous administration and vice versa; or the use of specialized routes such as subcutaneous, intramuscular, intraarterial, intraperitoneal, intralesional, intralymphatic, intratumoral, intrathecal, intravesicular, or intracranial. The route of administration can be a route of administration selected from the group consisting of:
   (a) intravenous administration;
   (b) topical administration;
   (c) intravesicular administration for bladder cancer;
   (d) oral administration;
   (e) slow release oral delivery;
   (f) intrathecal administration;
   (g) intraarterial administration;
   (h) continuous infusion; and
   (i) intermittent infusion.

In another alternative, the adaptation or improvement is made by the schedule of administration. This can involve alterations to the time, frequency, or duration that the therapeutically active compound is administered. The schedule of administration can be a schedule of administration selected from the group consisting of:
   (a) daily administration;
   (b) weekly administration;
   (c) weekly administration for three weeks;
   (d) biweekly administration;
   (e) biweekly administration for three weeks with a 1-2 week rest period;
   (f) intermittent boost dose administration; and
   (g) daily administration for one week for multiple weeks.

In yet another alternative, the adaptation or improvement can be made by veterinary subject selection. This can involve alterations to the type of veterinary subject that would best tolerate or benefit from the therapeutically active compound. For example, such selection can involve the use of dosages intended for young animals for elderly animals, use of altered doses for obese animals, or exploitation of co-morbid disease conditions such as diabetes, cirrhosis, or other conditions that may uniquely exploit a feature of the compound. When the adaptation or improvement is made by veterinary subject selection, the veterinary subject selection can be carried out by a criterion selected from the group consisting of:
   (a) selecting veterinary subjects with a disease condition characterized by a high level of a metabolic enzyme selected from the group consisting of histone deacetylase and ornithine decarboxylase;
   (b) selecting veterinary subjects with a low or high susceptibility to a condition selected from the group consisting of thrombocytopenia and neutropenia;
   (c) selecting veterinary subjects intolerant of GI toxicities; and
   (d) selecting veterinary subjects characterized by over- or under-expression of a gene selected from the group consisting of c-Jun, a GPCR, a signal transduction protein, VEGF, a prostate-specific gene, and a protein kinase.

The cellular proto-oncogene c-Jun encodes a protein that, in combination with c-Fos, forms the AP-1 early response transcription factor. This proto-oncogene plays a key role in transcription and interacts with a large number of proteins affecting transcription and gene expression. It is also involved in proliferation and apoptosis of cells that form part of a number of tissues, including cells of the endometrium and glandular epithelial cells. G-protein coupled receptors (GPCRs) are important signal transducing receptors. The superfamily of G protein coupled receptors includes a large number of receptors. These receptors are integral membrane proteins characterized by amino acid sequences that contain seven hydrophobic domains, predicted to represent the transmembrane spanning regions of the proteins. They are found in a wide range of organisms and are involved in the transmission of signals to the interior of cells as a result of their interaction with heterotrimeric G proteins. They respond to a diverse range of agents including lipid analogues, amino acid derivatives, small molecules such as epinephrine and dopamine, and various sensory stimuli. The properties of many known GPCR are summarized in S. Watson & S. Arkinstall, "The G-Protein Linked Receptor Facts Book" (Academic Press, London, 1994), incorporated herein by this reference. GPCR receptors include, but are not limited to, acetylcholine receptors, β-adrenergic receptors, $β_3$-adrenergic receptors, serotonin (5-hydroxytryptamine)

receptors, dopamine receptors, adenosine receptors, angiotensin Type II receptors, bradykinin receptors, calcitonin receptors, calcitonin gene-related receptors, cannabinoid receptors, cholecystokinin receptors, chemokine receptors, cytokine receptors, gastrin receptors, endothelin receptors, γ-aminobutyric acid (GABA) receptors, galanin receptors, glucagon receptors, glutamate receptors, luteinizing hormone receptors, choriogonadotrophin receptors, follicle-stimulating hormone receptors, thyroid-stimulating hormone receptors, gonadotrophin-releasing hormone receptors, leukotriene receptors, Neuropeptide Y receptors, opioid receptors, parathyroid hormone receptors, platelet activating factor receptors, prostanoid (prostaglandin) receptors, somatostatin receptors, thyrotropin-releasing hormone receptors, vasopressin and oxytocin receptors.

In yet another alternative, the adaptation or improvement can be made by analysis of veterinary subject or disease phenotype. This can involve more precise identification of a veterinary subject's ability to tolerate, metabolize and exploit the use of the compound. This can include use of diagnostic tools and kits to better characterize a veterinary subject's ability to process/metabolize a chemotherapeutic agent or their susceptibility to toxicity caused by potential specialized cellular, metabolic, organ system phenotypes. The analysis of veterinary subject or disease phenotype can be carried out by a method selected from the group consisting of:
  (a) use of a diagnostic tool, a diagnostic technique, a diagnostic kit, or a diagnostic assay to confirm a veterinary subject's particular phenotype;
  (b) use of a method for measurement of a marker selected from the group consisting of histone deacetylase, ornithine decarboxylase, VEGF, a protein that is a gene product of a prostate specific gene, a protein that is a gene product of jun, and a protein kinase;
  (c) surrogate compound dosing; and
  (d) low dose pre-testing for enzymatic status.

In yet another alternative, the adaptation or improvement can be made by analysis of veterinary subject or disease genotype. This can be performed by testing and analyzing a veterinary subject's genotype for unique features that may be of value to predict efficacy, toxicity, metabolism, or other factors affecting the therapeutic efficacy of the drug. For example, this can involve biopsy samples of tumors or normal tissues (e.g., white blood cells) that may also be taken and analyzed to specifically tailor or monitor the use of a particular drug against a gene target; studies of unique tumor gene expression patterns; or analysis of SNP's (single nucleotide polymorphisms), to enhance efficacy or to avoid particular drug-sensitive normal tissue toxicities. The analysis of veterinary subject or disease genotype can be carried out by a method selected from the group consisting of:
  (a) use of a diagnostic tool, a diagnostic technique, a diagnostic kit, or a diagnostic assay to confirm a veterinary subject's particular genotype;
  (b) use of a gene chip;
  (c) use of gene expression analysis;
  (d) use of single nucleotide polymorphism (SNP) analysis;
  (e) measurement of the level of a metabolite or a metabolic enzyme;
  (f) analysis of chromosomal aberrations associated with malignancy or the risk of developing malignancy;
  (g) use of comparative genomic hybridization;
  (h) use of microRNA profiling;
  (i) use of genome wide association studies; and
  (j) use of haplotype analysis.

The use of gene chips is described in A. J. Lee & S. Ramaswamy, "DNA Microarrays in Biological Discovery and Patient Care" in *Essentials of Genomic and Personalized Medicine* (G. S. Ginsburg & H. F. Willard, eds., Academic Press, Amsterdam, 2010), ch. 7, pp. 73-88, incorporated herein by this reference.

When the method is the use of single nucleotide polymorphism (SNP) analysis, the SNP analysis can be carried out on a gene selected from the group consisting of histone deacetylase, ornithine decarboxylase, VEGF, a prostate specific gene, c-Jun, and a protein kinase. The use of SNP analysis is described in S. Levy and Y.-H. Rogers, "DNA Sequencing for the Detection of Human Genome Variation" in *Essentials of Genomic and Personalized Medicine* (G. S. Ginsburg & H. F. Willard, eds., Academic Press, Amsterdam, 2010), ch. 3, pp. 27-37, incorporated herein by this reference.

Still other genomic techniques such as copy number variation analysis and analysis of DNA methylation can be employed. Copy number variation analysis is described in C. Lee et al., "Copy Number Variation and Human Health" in *Essentials of Genomic and Personalized Medicine* (G. S. Ginsburg & H. F. Willard, eds., Academic Press, Amsterdam, 2010), ch. 5, pp. 46-59, incorporated herein by this reference. DNA methylation analysis is described in S. Cottrell et al., "DNA Methylation Analysis: Providing New Insight into Human Disease" in *Essentials of Genomic and Personalized Medicine* (G. S. Ginsburg & H. F. Willard, eds., Academic Press, Amsterdam, 2010), ch. 6, pp. 60-72, incorporated herein by this reference.

The use of comparative genomic hybridization is described in D. Pinkel & D. G. Albertson, *Annu. Rev. Genomics Human Genet.* 6: 331-354 (2005), incorporated herein by this reference.

The use of microRNA profiling is described in L. Zhang et al., "MicroRNAs Exhibit High Frequency Genomic Alterations in Human Cancer," *Proc. Natl. Acad. Sci. USA* 103: 9136-9141 (2006), incorporated herein by this reference.

The use of genome wide association studies is described in J. C. Barrett & L. R. Cardon, "Evaluating Coverage of Genome-Wide Association Studies," *Nat. Genet.* 38: 659-662 (2006).

The use of haplotype analysis is described in International HapMap Consortium, "A Haplotype Map of the Human Genome," *Nature* 437: 1299-1320 (2005).

In yet another alternative, the adaptation or improvement can be made by pre/post treatment preparation. This can involve specialized preparation of a veterinary subject prior to or after the use of a chemotherapeutic agent, such as through induction or inhibition of metabolizing enzymes or specific protection of sensitive normal tissues or organ systems. The pre/post treatment preparation can be selected from the group consisting of:
  (a) the use of colchicine or an analog thereof;
  (b) the use of a uricosuric;
  (c) the use of uricase;
  (d) the non-oral use of nicotinamide;
  (e) the use of a sustained-release form of nicotinamide;
  (f) the use of an inhibitor of poly-ADP ribose polymerase;
  (g) the use of caffeine;
  (h) the use of leucovorin rescue;
  (i) infection control; and
  (j) the use of an anti-hypertensive agent.

Uricosurics include, but are not limited to, probenecid, benzbromarone, and sulfinpyrazone. A particularly preferred uricosuric is probenecid. Uricosurics, including probenecid, may also have diuretic activity.

Poly-ADP ribose polymerase inhibitors are described in G. J. Southan & C. Szabó, "Poly(ADP-Ribose) Inhibitors," *Curr. Med. Chem.* 10: 321-240 (2003), incorporated herein by this reference, and include nicotinamide, 3-aminobenzamide, substituted 3,4-dihydroisoquinolin-1(2H)-ones and isoquinolin-1(2H)-ones, benzimidazoles, indoles, phthalazin-1(2H)-ones, quinazolinones, isoindolinones, phenanthridinones, and other compounds.

Leucovorin rescue comprises administration of folinic acid (leucovorin) to patients in which methotrexate has been administered. Leucovorin is a reduced form of folic acid that bypasses dihydrofolate reductase and restores hematopoietic function. Leucovorin can be administered either intravenously or orally.

In one alternative, wherein the pre/post treatment is the use of a uricosuric, the uricosuric is probenecid or an analog thereof.

In yet another alternative, the adaptation or improvement can be made by toxicity management. This comprises additional drugs or procedures to prevent or reduce potential side effects or toxicities. The toxicity management can be selected from the group consisting of:
(a) the use of colchicine or an analog thereof;
(b) the use of a uricosuric;
(c) the use of uricase;
(d) the non-oral use of nicotinamide;
(e) the use of a sustained-release form of nicotinamide;
(f) the use of an inhibitor of poly-ADP ribose polymerase;
(g) the use of caffeine;
(h) the use of leucovorin rescue;
(i) the use of sustained-release allopurinol;
(j) the non-oral use of allopurinol;
(k) the use of bone marrow transplants;
(l) the use of a blood cell stimulant;
(m) the use of blood or platelet infusions;
(n) the administration of an agent selected from the group consisting of filgrastim (Neupogen®), G-CSF, and GM-CSF;
(o) the application of a pain management technique;
(p) the administration of an anti-inflammatory agent;
(q) the administration of fluids;
(r) the administration of a corticosteroid;
(s) the administration of an insulin control medication;
(t) the administration of an antipyretic;
(u) the administration of an anti-nausea treatment;
(v) the administration of an anti-diarrheal treatment;
(w) the administration of N-acetylcysteine; and
(x) the administration of an antihistamine.

Filgrastim is a granulocytic colony-stimulating factor (G-CSF) analog produced by recombinant DNA technology that is used to stimulate the proliferation and differentiation of granulocytes and is used to treat neutropenia; G-CSF can be used in a similar manner. GM-CSF is granulocyte macrophage colony-stimulating factor and stimulates stem cells to produce granulocytes (eosinophils, neutrophils, and basophils) and monocytes; its administration is useful to prevent or treat infection.

Anti-inflammatory agents are well known in the art and include corticosteroids and non-steroidal anti-inflammatory agents (NSAIDs). Corticosteroids with anti-inflammatory activity include, but are not limited to, hydrocortisone, cortisone, beclomethasone dipropionate, betamethasone, dexamethasone, prednisone, methylprednisolone, triamcinolone, fluocinolone acetonide, and fludrocortisone. Non-steroidal anti-inflammatory agents include, but are not limited to, acetylsalicylic acid (aspirin), sodium salicylate, choline magnesium trisalicylate, salsalate, diflunisal, sulfasalazine, olsalazine, acetaminophen, indomethacin, sulindac, tolmetin, diclofenac, ketorolac, ibuprofen, naproxen, flurbiprofen, ketoprofen, fenoprofin, oxaprozin, mefenamic acid, meclofenamic acid, piroxicam, meloxicam, nabumetone, rofecoxib, celecoxib, etodolac, nimesulide, aceclofenac, alclofenac, alminoprofen, amfenac, ampiroxicam, apazone, araprofen, azapropazone, bendazac, benoxaprofen, benzydamine, bermoprofen, benzpiperylon, bromfenac, bucloxic acid, bumadizone, butibufen, carprofen, cimicoxib, cinmetacin, cinnoxicam, clidanac, clofezone, clonixin, clopirac, darbufelone, deracoxib, droxicam, eltenac, enfenamic acid, epirizole, esflurbiprofen, ethenzamide, etofenamate, etoricoxib, felbinac, fenbufen, fenclofenac, fenclozic acid, fenclozine, fendosal, fentiazac, feprazone, filenadol, flobufen, florifenine, flosulide, flubichin methanesulfonate, flufenamic acid, flufenisal, flunixin, flunoxaprofen, fluprofen, fluproquazone, furofenac, ibufenac, imrecoxib, indoprofen, isofezolac, isoxepac, isoxicam, licofelone, lobuprofen, lomoxicam, lonazolac, loxaprofen, lumaricoxib, mabuprofen, miroprofen, mofebutazone, mofezolac, morazone, nepafanac, niflumic acid, nitrofenac, nitroflurbiprofen, nitronaproxen, orpanoxin, oxaceprol, oxindanac, oxpinac, oxyphenbutazone, pamicogrel, parcetasal, parecoxib, parsalmide, pelubiprofen, pemedolac, phenylbutazone, pirazolac, pirprofen, pranoprofen, salicin, salicylamide, salicylsalicylic acid, satigrel, sudoxicam, suprofen, talmetacin, talniflumate, tazofelone, tebufelone, tenidap, tenoxicam, tepoxalin, tiaprofenic acid, tiaramide, tilmacoxib, tinoridine, tiopinac, tioxaprofen, tolfenamic acid, triflusal, tropesin, ursolic acid, valdecoxib, ximoprofen, zaltoprofen, zidometacin, and zomepirac, and the salts, solvates, analogues, congeners, bioisosteres, hydrolysis products, metabolites, precursors, and prodrugs thereof.

The clinical use of corticosteroids is described in B. P. Schimmer & K. L. Parker, "Adrenocorticotropic Hormone; Adrenocortical Steroids and Their Synthetic Analogs; Inhibitors of the Synthesis and Actions of Adrenocortical Hormones" in *Goodman & Gilman's The Pharmacological Basis of Therapeutics* (L. L. Brunton, ed., 11$^{th}$ ed., McGraw-Hill, New York, 2006), ch. 59, pp. 1587-1612, incorporated herein by this reference.

Anti-nausea treatments include, but are not limited to, ondansetron, metoclopramide, promethazine, cyclizine, hyoscine, dronabinol, dimenhydrinate, diphenhydramine, hydroxyzine, medizine, dolasetron, granisetron, palonosetron, ramosetron, domperidone, haloperidol, chlorpromazine, fluphenazine, perphenazine, prochlorperazine, betamethasone, dexamethasone, lorazepam, and thiethylperazine.

Anti-diarrheal treatments include, but are not limited to, diphenoxylate, difenoxin, loperamide, codeine, racecadotril, octreoside, and berberine.

N-acetylcysteine is an antioxidant and mucolytic that also provides biologically accessible sulfur.

In yet another alternative, the adaptation or improvement can be made by pharmacokinetic/pharmacodynamic monitoring. This comprises such procedures as monitoring drug levels after dosing in an effort to maximize a patient's drug plasma level, monitoring the generation of toxic metabolites, or monitoring of ancillary medicines that could be beneficial or harmful in terms of drug-drug interactions. The pharmacokinetic/pharmacodynamic monitoring can be performed by a method selected from the group consisting of:
(a) multiple determinations of blood plasma levels; and
(b) multiple determinations of at least one metabolite in blood or urine.

Typically, determination of blood plasma levels or determination of at least one metabolite in blood or urine is carried out by immunoassays. Methods for performing immunoassays are well known in the art, and include radioimmunoassay, ELISA (enzyme-linked immunosorbent assay), competitive immunoassay, immunoassay employing lateral flow test strips, and other assay methods.

In yet another alternative, the adaptation or improvement can be made by drug combination. These drug combinations can provide a more than additive or synergistic improvement in efficacy or side-effect management. The drug combination can be selected from the group consisting of:

(a) use with topoisomerase inhibitors;
(b) use with fraudulent nucleosides;
(c) use with fraudulent nucleotides;
(d) use with thymidylate synthetase inhibitors;
(e) use with signal transduction inhibitors;
(f) use with cisplatin or platinum analogs;
(g) use with alkylating agents;
(h) use with anti-tubulin agents;
(i) use with antimetabolites;
(j) use with berberine;
(k) use with apigenin;
(l) use with amonafide;
(m) use with vinca alkaloids;
(n) use with 5-fluorouracil;
(o) use with curcumin;
(p) use with NF-κB inhibitors;
(q) use with rosmarinic acid;
(r) use with mitoguazone; and
(s) use with tetrandrine.

Topoisomerase inhibitors include, but are not limited to, irinotecan, topotecan, camptothecin, lamellarin D, amsacrine, etoposide, etoposide phosphate, teniposide, doxorubicin, and ICRF-193.

Fraudulent nucleosides include, but are not limited to, cytosine arabinoside, gemcitabine, and fludarabine; other fraudulent nucleosides are known in the art.

Fraudulent nucleotides include, but are not limited to, tenofovir disoproxil fumarate and adefovir dipivoxil; other fraudulent nucleotides are known in the art.

Thymidylate synthetase inhibitors include, but are not limited to, raltitrexed, pemetrexed, nolatrexed, ZD9331, GS7094L, fluorouracil, and BGC 945.

Signal transduction inhibitors are described in A. V. Lee et al., "New Mechanisms of Signal Transduction Inhibitor Action: Receptor Tyrosine Kinase Down-Regulation and Blockade of Signal Transactivation," *Clin. Cancer Res.* 9: 516s (2003), incorporated herein in its entirety by this reference.

Alkylating agents include, but are not limited to, Shionogi 254-S, aldo-phosphamide analogues, altretamine, anaxirone, Boehringer Mannheim BBR-2207, bendamustine, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)$_2$, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, melphalan, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromustine, Tanabe Seiyaku TA-077, tauromustine, temozolomide, teroxirone, tetraplatin and trimelamol, as described in U.S. Pat. No. 7,446,122 by Chao et al., incorporated herein by this reference.

Anti-tubulin agents include, but are not limited to, vinca alkaloids, taxanes, podophyllotoxin, halichondrin B, and homohalichondrin B.

Antimetabolites include, but are not limited to: methotrexate, pemetrexed, 5-fluorouracil, capecitabine, cytarabine, gemcitabine, 6-mercaptopurine, and pentostatin, alanosine, AG2037 (Pfizer), 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrill-Dow DDFC, deazaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT and uricytin.

Berberine has antibiotic activity and prevents and suppresses the expression of pro-inflammatory cytokines and E-selectin, as well as increasing adiponectin expression.

Apigenin is a flavone that can reverse the adverse effects of cyclosporine and has chemoprotective activity, either alone or derivatized with a sugar.

Amonafide is a topoisomerase inhibitor and DNA intercalator that has anti-neoplastic activity.

Curcumin is believed to have anti-neoplastic, anti-inflammatory, antioxidant, anti-ischemic, anti-arthritic, and anti-amyloid properties and also has hepatoprotective activity.

NF-κB inhibitors include, but are not limited to, bortezomib.

Rosmarinic acid is a naturally-occurring phenolic antioxidant that also has anti-inflammatory activity.

Mitoguazone is an inhibitor of polyamine biosynthesis through competitive inhibition of S-adenosylmethionine decarboxylase.

Tetrandrine has the chemical structure 6,6',7,12-tetramethoxy-2,2'-dimethyl-1β-berbaman and is a calcium channel blocker that has anti-inflammatory, immunologic, and anti-allergenic effects, as well as an anti-arrhythmic effect similar to that of quinidine. It has been isolated from *Stephania tetranda* and other Asian herbs.

In one alternative, when the drug combination is use with an alkylating agent, the alkylating agent can be selected from the group consisting of BCNU, BCNU wafers (Gliadel), and CCNU.

United States Patent Application Publication No. 2010/0069458 by Atadja et al., incorporated herein by this reference discloses the use of the following additional therapeutic agents, which can be used together with dianhydrogalactitol, diacetyldianhydrogalactitol, dibromodulcitol, and their derivatives, as described above:

(1) ACE inhibitors, including, but not limited to, benazepril, enazepril, captopril, enalapril, fosinopril, lisinopril, moexipril, quinapril, ramipril, perindopril and trandolapril;

(2) adenosine kinase inhibitors, including, but not limited to, 5-iodotubericidin;

(3) adrenal cortex antagonists, including, but not limited to, mitotane;

(4) AKT pathway inhibitors (protein kinase B inhibitors) including, but not limited to, deguelin and 1,5-dihydro-5-methyl-1-β-D-ribofuranosyl-1,4,5,6,8-pentaazaacenaphthylen-3-amine;

(5) angiogenesis inhibitors, including, but not limited to, fumagillin, Shikonin, Tranilast, ursolic acid; suramin; thalidomide, lenalidomide; phthalazines, including, but not limited to, 1-(4-chloroanilino)-4-(4-pyridylmethyl)phthalazine, 1-(4-methylanilino)-4-(4-pyridylmethyl)phthalazine, 1-(3-chloroanilino)-4-(4-pyridylmethyl)phthalazine, 1-anilino-4-(4-pyridylmethyl)phthalazine, 1-benzylamino-4-(4-pyridylmethyl)phthalazine, 1-(4-methoxyanilino)-4-(4-pyridylmethyl)phthalazine, 1-(3-benzyloxyanilino)-4-(4-pyridylmethyl)phthalazine, 1-(3-methoxyanilino)-4-(4-pyridylmethyl)phthalazine, 1-(2-Methoxyanilino}-4-(4-pyridylmethyl)phthalazine, 1-(4-trifluoromethylanilino)-4-(4-pyridylmethyl)phthalazine, 1-(4-fluoroanilino)-4-(4-pyridylmethyl)phthalazine, 1-(3-hydroxyanilino)-4-(4-pyridylmethyl)phthalazine, 1-(4-hydroxyanilino)-4-(4-pyridylmethyl)phthalazine, 1-(3-aminoanilino)-4-(4-pyridylmethyl)phthalazine, 1-(3,4-dichloroanilino)-4-(4-pyridylmethyl)phthalazine, 1-(4-bromoanilino)-4-(4-pyridylmethyl)phthalazine, 1-(3-chloro-4-methoxyanilino)-4-(4-pyridylmethyl)phthalazine, 1-(4-cyanoanilino)-4-(4-pyridylmethyl)phthalazine, 1-(3-chloro-4-fluoroanilino)-4-(4-pyridylmethyl)phthalazine, 1-(3-methylanilino)-4-(4-pyridylmethyl)phthalazine, and other phthalazines disclosed in PCT Patent Application Publication No. WO 98/035958 by Bold et al., incorporated herein in its entirety by this reference, isoquinolines disclosed in PCT Patent Application Publication No. WO 00/09495 by Altmann et al., incorporated herein in its entirety by this reference, including 1-(3,5-dimethylanilino)-4-(pyridin-4-ylmethyl)-isoquinoline; phthalazines disclosed in PCT Patent Application Publication No. WO 00/59509 by Bold et al., incorporated herein in its entirety by this reference, including E-1-(3-methylanilino)-4-[(2-(pyridin-3-yl)vinyl]phthalazine, Z-1-(3-methylanilino)-4-[(2-(pyridin-3-yl)vinyl]phthalazine, 1-(3-methylanilino)-4-[(2-(pyridin-3-yl)ethyl]phthalazine, 1-(3-methylanilino)-4-[{2-(pyridin-4-yl)vinyl]phthalazine, 1-(4-chloro-3-trifluoromethylanilino)-4-[(2-(pyridin-3-yl)ethyl]phthalazine, 1-(4-chloroanilino)-4-[(2-(pyridin-3-yl)ethyl]phthalazine, 1-(3-chlorobenzylamino)-4-[(2-(pyridin-3-yl)ethyl]phthalazine, 1-(4-chloro-3-trifluoromethylanilino)-4-[3-(pyridin-3-yl)propyl]phthalazine, 1-(4-chloroanilino)-4-[3-(pyridin-3-yl)propyl]phthalazine, 1-(3-chloro-5-trifluoromethylanilino)-4-[3-(pyridin-3-yl)propyl]phthalazine, and 1-(4-tert-butylanilino)-4-[3-(pyridin-3-yl)propyl]phthalazine; and monoclonal antibodies;

(6) angiostatic steroids, including, but not limited to, anecortave, triamcinolone, hydrocortisone, 11α-epihydrocotisol, cortexolone, 17α-hydroxyprogesterone, corticosterone, desoxycorticosterone, testosterone, estrone, and dexamethasone;

(7) anti-androgens, including, but not limited to, nilutamide and bicalutamide;

(8) anti-estrogens, including, but not limited to, toremifene, letrozole, testolactone, anastrozole, bicalutamide, flutamide, exemestane, tamoxifen, fulvestrant, and raloxifene;

(9) anti-hypercalcemia agents, including, but not limited to, gallium (III) nitrate hydrate and pamidronate disodium;

(10) apoptosis inducers, including, but not limited to, 2-[[3-(2,3-dichlorophenoxy)propyl]amino]-ethanol, gambogic acid, embellin, and arsenic trioxide;

(11) ATI receptor antagonists, including, but not limited to, valsartan;

(12) aurora kinase inhibitors, including, but not limited to, binucleine 2;

(13) aromatase inhibitors, including, but not limited to: (a) steroids, including, but not limited to, atamestane, exemestane, and formestane; and (b) non-steroids, including, but not limited to, aminoglutethimide, roglethimide, pyridoglutethimide, trilostane, testolactone, ketokonazole, vorozole, fadrozole, anastrozole, and letrozole;

(14) bisphosphonates, including, but not limited to, etidronic acid, clodronic acid, tiludronic acid, alendronic acid, ibandronic acid, risedronic acid, and zoledronic acid;

(15) Bruton's tyrosine kinase inhibitors, including, but not limited to, terreic acid;

(16) calcineurin inhibitors, including, but not limited to, cypermethrin, deltamethrin, fenvalerate, and tyrphostin 8;

(17) CaM kinase II inhibitors, including, but not limited to, the 5-isoquinolinesulfonic acid 4-[(2S)-2-[(5-isoquinolinylsulfonyl)methylamino]-3-oxo-3-(4-phenyl-1-piperazinyl)propyl]phenyl ester, and N-[2-[[[3-(4-chlorophenyl)-2-propenyl]methyl]amino]methyl]phenyl]-N-(2-hydroxyethyl)-4-methoxy-benzenesulfonamide;

(18) CD45 tyrosine phosphatase inhibitors, including, but not limited to, [[2-(4-bromophenoxy)-5-nitrophenyl]hydroxymethyl]-phosphonic acid;

(19) CDC25 phosphatase inhibitors, including, but not limited to, 2,3-bis[(2-hydroyethyl)thio]-1,4-naphthalenedione;

(20) CHK kinase inhibitors, including, but not limited to, debromohymenialdisine;

(21) compounds targeting/decreasing a protein or lipid kinase activity; or a protein or lipid phosphatase activity; or further anti-angiogenic compounds, including, but not limited to, protein tyrosine kinase and/or serine and/or threonine kinase inhibitors or lipid kinase inhibitors, including, but not limited to:

(a) compounds targeting, decreasing or inhibiting the activity of the vascular endothelial growth factor receptors (VEGFR) or of vascular endothelial growth factor (VEGF), including, but not limited to, 7H-pyrrolo[2,3-d]pyrimidine derivatives, including: [6-[4-(4-ethyl-piperazine-1-ylmethyl)-phenyl]-7H-pyrrolo[2,3-d]pyrimidinpyrimidin-4-yl]-(R)-1-phenyl-ethylyamine (known as AEE788), BAY 43-9006; and isoquinoline compounds disclosed in PCT Patent Application Publication No. WO 00/09495, such as (4-tert-butyl-phenyl)-94-pyridin-4-ylmethyl-isoquinolin-1-yl)-amine;

(b) compounds targeting, decreasing or inhibiting the activity of the platelet-derived growth factor-receptor (PDGFR), including, but not limited to: N-phenyl-2-pyrimidine-amine derivatives, e.g., imatinib, SU101, SU6668 and GFB-111;

(c) compounds targeting, decreasing or inhibiting the activity of the fibroblast growth factor-receptor (FGFR);

(d) compounds targeting, decreasing or inhibiting the activity of the insulin-like growth factor receptor 1 (IGF-1R), including, but not limited to: the compounds disclosed in WO 02/092599 and derivatives thereof of 4-amino-5-phenyl-7-cyclobutyl-pyrrolo[2,3-d]pyrimidine derivatives;

(e) compounds targeting, decreasing or inhibiting the activity of the Trk receptor tyrosine kinase family;

(f) compounds targeting, decreasing or inhibiting the activity of the Axl receptor tyrosine kinase family;

(g) compounds targeting, decreasing or inhibiting the activity of the c-Met receptor;

(h) compounds targeting, decreasing or inhibiting the activity of the Ret receptor tyrosine kinase;

(i) compounds targeting, decreasing or inhibiting the activity of the Kit/SCFR receptor tyrosine kinase;

(j) compounds targeting, decreasing or inhibiting the activity of the C-kit receptor tyrosine kinases, including, but not limited to, imatinib;

(k) compounds targeting, decreasing or inhibiting the activity of members of the c-Abl family and their gene-fusion products, e.g., BCR-Abl kinase, such as N-phenyl-2-pyrimidine-amine derivatives, including, but not limited to: imatinib, 6-(2,6-dichlorophenyl)-2-[(4-fluoro-3-methylphenyl)amino]-8-methyl-pyrido[2,3-d]pyrimidin-7(8H)-one (PD180970), methyl-4-[N-(2',5'-dihydroxybenzyl)amino]benzoate (Tyrphostin AG957), 4-[[(2,5-dihydroxyphenyl)methyl]amino]benzoic acid tricyclo[3.3.1.13,7]dec-1-yl ester (adaphostin or NSC 680410), 6-(2,6-dichlorophenyl)-8-methyl-2-(3-methylsulfanylanilino)pyrido[2,3-d]pyrimidin-7-one (PD173955), and desatinib;

(l) compounds targeting, decreasing or inhibiting the activity of members of the protein kinase C (PKC) and Raf family of serine/threonine kinases, members of the MEK, SRC, JAK, FAK, PDK and Ras/MAPK family members, or PI(3) kinase family, or of the PI(3)-kinase-related kinase family, and/or members of the cyclin-dependent kinase family (CDK) and are especially those staurosporine derivatives disclosed in U.S. Pat. No. 5,093,330, such as, but not limited to, midostaurin; examples of further compounds include, e.g., UCN-01; safingol, sorafenib, Bryostatin 1; Perifosine; Ilmofosine; 3-[3-[2,5-Dihydro-4-(1-methyl-1H-indol-3-yl)-2,5-dioxo-1H-pyrrol-3-yl]-1H-indol-1-yl]propyl carbamimidothioic acid ester (RO 318220), 3-[(8S)-8-[(dimethylamino)methyl]-6,7,8,9-tetrahydropyrido[1,2-a]indol-10-yl]-4-(1-methyl-1H-indol-3-yl)-1H-pyrrole-2,5-dione (RO 320432), 12-(2-cyanoethyl)-6,7,12,13-tetrahydro-13-methyl-5-oxo-5H-indolo[2,3-a]pyrrolo[3,4-c]carbazole (GO 6976); Isis 3521; (S)-13-[(dimethylamino)methyl]-10,11,14,15-tetrahydro-4,9:16, 21-dimetheno-1H, 13H-dibenzo[e,k]pyrrolo[3,4-h][1,4,13]oxadiazacy clohexadecene-1,3(2H)-dione (LY333531), LY379196; isoquinoline compounds, such as those disclosed in PCT Patent Application Publication No. WO 00/09495; farnesyltransferase inhibitors, including, but not limited to, tipifarnib and lonafarnib; 2-(2-chloro-4-iodo-phenylamino)-N-cyclopropylmethoxy-3,4-difluoro-benzamide (PD184352); and QAN697, a PI3K inhibitor;

(m) compounds targeting, decreasing or inhibiting the activity of protein-tyrosine kinase, such as, but not limited to, imatinib mesylate, a tyrphostin, pyrymidylaminobenzamide and derivatives thereof; a tyrphostin is preferably a low molecular weight ($M_r$<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810, Tyrphostin AG 99, Tyrphostin AG 213, Tyrphostin AG 1748, Tyrphostin AG 490, Tyrphostin B44, Tyrphostin B44 (+) enantiomer, Tyrphostin AG 555, AG 494, Tyrphostin AG 556; Tyrphostin AG957, and adaphostin (4-{[(2,5-dihydroxyphenyl)methyl]amino}-benzoic acid adamantyl ester or NSC 680410);

(n) compounds targeting, decreasing or inhibiting the activity of the epidermal growth factor family of receptor tyrosine kinases (EGFR, ErbB2, ErbB3, ErbB4 as homodimers or heterodimers), such as, but not limited to, those compounds, proteins or monoclonal antibodies generically and specifically disclosed in PCT Patent Application Publication No. WO 97/02266 by Traxler et al. such as (R)-6-(4-hydroxyphenyl)-4-[(1-phenylethyl)-amino]-7H-pyrrolo-[2,3-d]pyrimidine, or in European Patent Application Publication No. EP 0564409 by Zimmermann, PCT Patent Application Publication No. WO 99/03854 by Zimmermann et al., European Patent Application Publication No. EP 0520722 by Barker et al., European Patent Application Publication No. EP 0566226 by Barker et al., European Patent Application Publication EP 0787722 by Wissner et al., European Patent Application Publication EP 0837063 by Arnold et al., U.S. Pat. No. 5,747,498 by Schnur et al., PCT Patent Application Publication WO 98/10767 by McMahon et al., PCT Patent Application Publication WO 97/30034 by Barker, PCT Patent Application Publication WO 97/49688 by Schnur, PCT Patent Application Publication WO 97/38983 by Bridges et al., PCT Patent Application Publication WO 96/30347 by Schnur et al., including, but not limited to, N-(3-ethylnylphenyl)-6,7-bis(2-methoxyethoxy)-4-quinazolinamine (CP 358774 or erlotinib), PCT Patent Application Publication WO 96/33980 by Gibson et al., including, but not limited to, N-(3-chloro-4-fluorophenyl)-7-methoxy-6-(3-morpholin-4-ylpropoxy)quinazolin-4-amine (gefitinib); and PCT Patent Application Publication WO 95/03283 by Barker et al., including, but not limited to, compound 6-amino-4-(3-methylphenyl-amino)-quinazoline (ZM105180); monoclonal antibodies, including, but not limited to trastuzumab and cetuximab; and other small molecule inhibitors, including, but not limited to: canertinib, pelitinib, lapatinib, and 7H-pyrrolo-[2,3-d]pyrimidine derivatives which are disclosed in PCT Patent Application Publication WO 03/013541 by Bold et al.;

(22) compounds which target, decrease or inhibit the activity of a protein or lipid phosphatase, including, but not limited to, inhibitors of phosphatase 1, phosphatase 2A, PTEN or CDC25, such as, but not limited to okadaic acid or a derivative thereof;

(23) compounds which induce cell differentiation processes, including, but not limited to, retinoic acid, α-tocopherol, γ-tocopherol, δ-tocopherol, α-tocotrienol, γ-tocotrienol, and δ-tocotrienol;

(24) cRAF kinase inhibitors, including, but not limited to, 3-(3,5-dibromo-4-hydroxybenzylidene)-5-iodo-1,3-dihydroindol-2-one and 3-(dimethylamino)-N-[3-[(4-hydroxybenzoyl)amino]-4-methylphenyl]-benzamide;

(25) cyclin dependent kinase inhibitors, including, but not limited to, N9-isopropyl-olomoucine; olomoucine; purvalanol B, roascovitine, kenpaullone, and purvalanol A;

(26) cysteine protease inhibitors, including, but not limited to, N-[(1S)-3-fluoro-2-oxo-1-(2-phenyl]ethyl)propyl]amino]-2-oxo-1-(phenylmethyl)ethyl]-4-morpholinecarboxamide;

(27) DNA intercalators, including, but not limited to, plicamycin and dactinomycin;

(28) DNA strand breakers, including, but not limited to, bleomycin;

(29) E3 ligase inhibitors, including, but not limited to, N-((3,3,3-trifluoro-2-trifluoromethyl)propionyl)sulfanilamide;

(30) EDG binders, including, but not limited to, FTY720;

(31) endocrine hormones, including, but not limited to, leuprolide and megestrol acetate;

(32) farnesyltransferase inhibitors, including, but not limited to, α-hydroxyfarnesylphosphonic acid, 2-[[(2S)-2-[[(2S,3S)-2-[[(2R)-2-amino-3-mercaptopropyl]amino]-3-methylpentyl]oxy]-1-oxo-3-phenylpropyl]amino]-4-(methylsulfonyl)-, 1-methylethyl butanoic acid ester (2S), and manumycin A;

(33) Flk-1 kinase inhibitors, including, but not limited to, 2-cyano-3-[4-hydroxy-3,5-bis(1-methylethyl)phenyl]-N-(3-phenylpropyl)-,(2-E)-2-propenamide;

(34) Flt-3 inhibitors, including, but not limited to, N-benzoyl-staurosporine, midostaurin, and N-(2-diethylaminoethyl)-5-[(Z)-(5-fluoro-2-oxo-1H-indol-3-ylidene)methyl]-2,4-dimethyl-1H-pyrrole-3-carboxamide (sunitinib);

(35) gonadorelin agonists, including, but not limited to, abarelix, goserelin, and goserelin acetate;

(36) heparanase inhibitors, including, but not limited to, phosphomannopentaose sulfate (PI-88);

(37) histone deacetylase (HDAC) inhibitors, including, but not limited to, compounds disclosed in PCT Patent Application Publication No. WO 02/22577 by Bair et al., including, but not limited to, N-hydroxy-3-[4-[[(2-hydroxyethyl)[2-(1H-indol-3-yl)ethyl]-amino]methyl]phenyl]-2E-2-propenamide, suberoylanilide hydroxamic acid, 4-(2-aminophenylcarbamoyl)-benzyl]-carbamic acid pyridine-3-ylmethyl ester and derivatives thereof, butyric acid, pyroxamide, trichostatin A, oxamflatin, apicidin, depsipeptide, depudecin, trapoxin, HC toxin, and sodium phenylbutyrate;

(38) HSP90 inhibitors, including, but not limited to: 17-allylamino,17-demethoxygeldanamycin (17AAG); a geldanamycin derivative; other geldanamycin-related compounds; radicicol; and 5-(2,4-dihydroxy-5-isopropyl-phenyl)-4-(4-morpholin-4-ylmethyl-phenyl)-isoxazole-3-carboxylic acid ethylamide;

(39) IκBα inhibitors (IKKs), including, but not limited to, 3-[(4-methylphenyl)sulfonyl]-(2E)-2-propenenitrile;

(40) insulin receptor tyrosine kinase inhibitors, including, but not limited to, hydroxy-2-naphthalenylmethylphosphonic acid;

(41) c-Jun N-terminal kinase inhibitors, including, but not limited to, pyrazoleanthrone and epigallocatechin gallate;

(42) microtubule binding agents, including, but not limited to: vinblastine sulfate; vincristine sulfate; vindesine; vinorelbine; docetaxel; paclitaxel; discodermolides; colchicines; and epothilones and derivatives thereof, such as epothilone B or a derivative thereof;

(43) mitogen-activated protein (MAP) kinase inhibitors, including, but not limited to, N-[2-[[[3-(4-chlorophenyl)-2-propenyl]methyl]amino]methyl]phenyl]-N-(2-hydroxyethyl)-4-methoxy-benzenesulfonamide;

(44) MDM2 inhibitors, including, but not limited to, trans-4-iodo,4'-boranyl-chalcone;

(45) MEK inhibitors, including, but not limited to, bis[amino[2-aminophenyl)thio]methylene]-butanedinitrile;

(46) methionine aminopeptidase inhibitors, including, but not limited to, bengamide and derivatives thereof;

(47) MMP inhibitors, including, but not limited to: actinonin; epigallocatechin gallate; collagen peptidomimetic and non-peptidomimetic inhibitors; tetracycline derivatives such as hydroxamate, batimastat, marimastat, primomastat, TAA211, N-hydroxy-2(R)-[[(4-methoxyphenyl)sulfonyl](3-picolyl)amino]-3-methylbutanamide hydrochloride (MMI270B), and AAJ996;

(48) NGFR tyrosine kinase inhibitors, including, but not limited to, Tyrphostin AG 879;

(49) p38 MAP kinase inhibitors, including, but not limited to, 3-(dimethylamino)-N-[3-[(4-hydroxybenzoyl)amino]-4-methylphenyl]-benzamide;

(50) p56 tyrosine kinase inhibitors, including, but not limited to, 9,10-dihydro-3-hydroxy-1-methoxy-9,10-dioxo-2-anthracenecarboxaldehyde and Tyrphostin 46;

(51) PDGFR tyrosine kinase inhibitors, including, but not limited to, Tyrphostin AG 1296; Tyrphostin 9, 2-amino-4-(1H-indol-5-yl)-1,3-butadiene-1,1,3-tricarbonitrile, and imatinib;

(52) phosphatidylinositol 3-kinase inhibitors, including, but not limited to, wortmannin and quercetin dihydrate;

(53) phosphatase inhibitors, including, but not limited to, cantharidic acid, cantharidin, and (E)-N-[4-(2-carboxyethenyl)benzoyl]glycyl-L-α-glutamyl-L-leucinamide;

(54) platinum agents, including, but not limited to, carboplatin, cisplatin, oxaliplatin, satraplatin, and ZD0473;

(55) protein phosphatase inhibitors, including, but not limited to:
(a) PP1 and PP2A inhibitors, including, but not limited to, cantharidic acid and cantharidin;
(b) tyrosine phosphatase inhibitors, including, but not limited to, L-P-bromotetramisole oxalate, benzylphosphonic acid, and (5R)-4-hydroxy-5-(hydroxymethyl)-3-(1-oxohexadecyl)-2(5H)-furanone;

(56) PKC inhibitors, including, but not limited to, -[1-[3-(dimethylamino)propyl]-1H-indol-3-yl]-4-(1H-indol-3-yl)-1H-pyrrolo-2,5-dione, sphingosine, staurosporine, Tyrphostin 51, and hypericin;

(57) PKC delta kinase inhibitors, including, but not limited to, rottlerin;

(58) polyamine synthesis inhibitors, including, but not limited to, (RS)-2,5-diamino-2-(difluoromethyl)pentanoic acid (DMFO);

(59) proteasome inhibitors, including, but not limited to, aclacinomycin A, gliotoxin, and bortezomib;

(60) PTP1B inhibitors, including, but not limited to, (E)-N-[4-(2-carboxyethenyl)benzoyl]glycyl-L-α-glutamyl-L-leucinamide;

(61) protein tyrosine kinase inhibitors, including, but not limited to: Tyrphostin AG 126; Tyrphostin AG 1288; Tyrphostin AG 1295; geldanamycin; and genistein;

(62) SRC family tyrosine kinase inhibitors, including, but not limited to, 1-(1,1-dimethylethyl)-3-(1-naphthalenyl)-1H-pyrazolo[3,4-d]pyrimidin-4-amine, and 3-(4-chlorophenyl)-1-(1,1-dimethylethyl)-1H-pyrazolo[3,4-d]pyrimidin-4-amine;

(63) Syk tyrosine kinase inhibitors including, but not limited to, piceatannol;

(64) Janus (JAK-2 and/or JAK-3) tyrosine kinase inhibitors, including, but not limited to, Tyrphostin AG 490, and 2-naphthyl vinyl ketone;

(65) inhibitors of Ras oncogenic isoforms, including, but not limited to, (2S)-2-[[(2S)-2-[(2S,3S)-2-[(2R)-2-amino-3-mercaptopropyl]amino]-3-methylpentyl]oxy]-1-oxo-3-phenylpropyl]amino]-4-(methylsulfonyl)-butanoic acid 1-methylethyl ester (L-744832), DK8G557, and tipifarnib;

(66) retinoids, including, but not limited to, isotretinoin and tretinoin;

(67) ribonucleotide reductase inhibitors, including, but not limited to, hydroxyurea and 2-hydroxy-1H-isoindole-1,3-dione;

(68) RNA polymerase II elongation inhibitors, including, but not limited to, 5,6-dichloro-1-beta-D-ribofuranosylbenzimidazole;

(69) S-adenosylmethionine decarboxylase inhibitors, including, but not limited to, 5-amidino-1-tetralone-2'-amidinohydrazone and other compounds disclosed in U.S. Pat. No. 5,461,076 to Stanek et al., incorporated herein by this reference;

(70) serine/threonine kinase inhibitors, including, but not limited to, sorafenib and 2-aminopurine;

(71) compounds which target, decrease, or inhibit the activity or function of serine/threonine mTOR kinase, including, but not limited to, everolimus, temsirolimus, zotarolimus, rapamycin, derivatives and analogs of rapamycin, deforolimus, AP23841, sirolimus, and everolimus;

(72) somatostatin receptor antagonists, including, but not limited to, octreotide and pasireotide (SOM230);

(73) sterol biosynthesis inhibitors, including, but not limited to, terbinadine;

(74) telomerase inhibitors, including, but not limited to, telomestatin; and

(75) topoisomerase inhibitors, including, but not limited to:
- (a) topoisomerase I inhibitors, including, but not limited to, topotecan, gimatecan, irinotecan, camptothecin and its analogues, 9-nitrocamptothecin and the macromolecular camptothecin conjugate PNU-16614, macromolecular camptothecin conjugates described in PCT Patent Application Publication No. WO 99/17804 by Angelucci et al., 10-hydroxycamptothecin acetate salt, etoposide idarubicin hydrochloride, teniposide, doxorubicin; epirubicin hydrochloride, mitoxantrone hydrochloride, and daunorubicin hydrochloride; and
- (b) topoisomerase II inhibitors, including, but not limited to, anthracyclines, such as doxorubicin, including liposomal formulations thereof, daunorubicin, including liposomal formulations thereof, epirubicin, idarubicin, nemorubicin, mitoxantrone, losoxantrone, etoposide, and eniposide;

(76) VEGFR tyrosine kinase inhibitors, including, but not limited to, 3-(4-dimethylaminobenzylidenyl)-2-indolinone; and

(77) RANKL inhibitors, including, but not limited to, denosumab.

In yet another alternative, the adaptation or improvement can be made by chemosensitization. When such a drug acts as a chemosensitizer, no measurable activity is observed when used alone but in combination with other therapeutics a more than additive or synergistic improvement in efficacy is observed. The chemosensitization can comprise the use of the therapeutic agent as a chemosensitizer in combination with an agent selected from the group consisting of:
- (a) topoisomerase inhibitors;
- (b) fraudulent nucleosides;
- (c) fraudulent nucleotides;
- (d) thymidylate synthetase inhibitors;
- (e) signal transduction inhibitors;
- (f) cisplatin or platinum analogs;
- (g) alkylating agents;
- (h) anti-tubulin agents;
- (i) antimetabolites;
- (j) berberine;
- (k) apigenin;
- (l) amonafide;
- (m) vinca alkaloids;
- (n) 5-fluorouracil;
- (o) curcumin;
- (p) NF-κB inhibitors;
- (q) rosmarinic acid;
- (r) mitoguazone; and
- (s) tetrandrine.

In yet another alternative, the adaptation or improvement can be made by chemopotentiation. When such a drug acts as a chemopotentiator, minimal therapeutic activity is observed alone but in combination with other therapeutics unique drug a more than additive or synergistic improvement in efficacy is observed. The chemopotentiation can comprise the use of the therapeutic agent as a chemopotentiator in combination with an agent selected from the group consisting of:
- (a) topoisomerase inhibitors;
- (b) fraudulent nucleosides;
- (c) fraudulent nucleotides;
- (d) thymidylate synthetase inhibitors;
- (e) signal transduction inhibitors;
- (f) cisplatin or platinum analogs;
- (g) alkylating agents;
- (h) anti-tubulin agents;
- (i) antimetabolites;
- (j) berberine;
- (k) apigenin;
- (l) amonafide;
- (m) vinca alkaloids;
- (n) 5-fluorouracil;
- (o) curcumin;
- (p) NF-κB inhibitors;
- (q) rosmarinic acid;
- (r) mitoguazone; and
- (s) tetrandrine.

In yet another alternative, the adaptation or improvement can be made by post-treatment management. This allows for the maximum benefit to veterinary subjects treated with a therapeutically active compound. The post-treatment management can be selected from the group consisting of:
- (a) a therapy associated with pain management;
- (b) administration of an anti-emetic;
- (c) an anti-nausea therapy;
- (d) administration of an anti-inflammatory agent;
- (e) administration of an anti-pyretic agent; and
- (f) administration of an immune stimulant.

In yet another alternative, the adaptation or improvement can be made by the use of a herbal medication created either synthetically or through extraction. These herbal medications can include, but are not limited to, NF-κB inhibitors (such as parthenolide, curcumin, rosmarinic acid); natural anti-inflammatories (including rhein, parthenolide); immunostimulants (such as those found in Echinacea); antimicrobials (such as berberine); and flavonoids, isoflavones, and flavones (such as apigenenin, genistein, genistin, 6"-O-malonylgenistin, 6"-O-acetylgenistin, daidzein, daidzin, 6"-O-malonyldaidzin, 6"-O-acetylgenistin, glycitein, glycitin, 6"-O-malonylglycitin, and 6-O-acetylglycitin).

When the herbal medication created either synthetically or through extraction is a NF-κB inhibitor, the NF-κB inhibitor can be selected from the group consisting of parthenolide, curcumin, and rosmarinic acid. When the herbal medication created either synthetically or through extraction is a natural anti-inflammatory, the natural anti-inflammatory can be selected from the group consisting of rhein and parthenolide. When the herbal medication created either synthetically or through extraction is an immunostimulant, the immunostimulant can be a product found in or isolated from Echinacea. When the herbal medication created either synthetically or through extraction is an antimicrobial, the anti-microbial can be berberine. When the herbal medication created either synthetically or through extraction is a flavonoid or flavone, the flavonoid, isoflavone, or flavone can be selected from the group consisting of apigenin, genistein, apigenenin, genistein, genistin, 6"-O-malonylgenistin, 6"-O-acetylgenistin, daidzein, daidzin, 6"-O-malonyldaidzin, 6"-O-acetylgenistin, glycitein, glycitin, 6"-O-malonylglycitin, and 6-O-acetylglycitin.

In yet another alternative, the adaptation or improvement can be made by a bulk drug product improvement. Such a bulk drug product improvement constitutes an alteration in the pharmaceutical bulk substance. The bulk drug product improvement can be selected from the group consisting of:
  (a) salt formation;
  (b) preparation as a homogeneous crystal structure;
  (c) preparation as a pure isomer;
  (d) increased purity;
  (e) preparation with lower residual solvent content; and
  (f) preparation with lower residual heavy metal content.

In yet another alternative, the adaptation or improvement can be made by use of a diluent used to solubilize and deliver/present the compound for administration. The use of a diluent can be selected from the group consisting of:
  (a) an emulsion;
  (b) dimethylsulfoxide (DMSO);
  (c) N-methylformamide (NMF)
  (d) DMF;
  (e) ethanol;
  (f) benzyl alcohol;
  (g) dextrose-containing water for injection;
  (h) Cremophor;
  (i) cyclodextrin; and
  (j) PEG.

In yet another alternative, the adaptation or improvement can be made by use of a solvent system used or required to solubilize a compound for administration or for further dilution. The solvent system can be selected from the group consisting of:
  (a) an emulsion;
  (b) dimethylsulfoxide (DMSO);
  (c) N-methylformamide (NMF)
  (d) DMF;
  (e) ethanol;
  (f) benzyl alcohol;
  (g) dextrose-containing water for injection;
  (h) Cremophor;
  (i) cyclodextrin; and
  (j) PEG.

In yet another alternative, the adaptation or improvement can be made by use of an excipient. These are materials, buffering agents, or preservatives required to stabilize and present a chemical compound for proper administration. The excipient can be selected from the group consisting of:
  (a) mannitol;
  (b) albumin;
  (c) EDTA;
  (d) sodium bisulfite;
  (e) benzyl alcohol;
  (f) a carbonate buffer; and
  (g) a phosphate buffer.

In yet another alternative, the adaptation or improvement can be made by use of a dosage form optimized for veterinary use. Alterations in the potential dosage forms of the compound can be dependent on the route of administration, duration of effect, plasma levels required, exposure to side-effect normal tissues and metabolizing enzymes. The dosage form optimized for veterinary use can be selected from the group consisting of:
  (a) tablets;
  (b) capsules;
  (c) topical gels;
  (d) topical creams;
  (e) patches;
  (f) suppositories; and
  (g) lyophilized dosage fills.

Formulation of pharmaceutical compositions in tablets, capsules, and topical gels, topical creams or suppositories is well known in the art and is described, for example, in United States Patent Application Publication No. 2004/0023290 by Griffin et al., incorporated herein by this reference.

Formulation of pharmaceutical compositions as patches such as transdermal patches is well known in the art and is described, for example, in U.S. Pat. No. 7,728,042 to Eros et al., incorporated herein by this reference.

Lyophilized dosage fills are also well known in the art. One general method for the preparation of such lyophilized dosage fills, applicable to dianhydrogalactitol and derivatives thereof and to diacetyldianhydrogalactitol and derivatives thereof, comprises the following steps:

(1) Dissolve the drug in water for injection precooled to below 10° C. Dilute to final volume with cold water for injection to yield a 40 mg/mL solution.

(2) Filter the bulk solution through an 0.2-µm filter into a receiving container under aseptic conditions. The formulation and filtration should be completed in 1 hour.

(3) Fill nominal 1.0 mL filtered solution into sterilized glass vials in a controlled target range under aseptic conditions.

(4) After the filling, all vials are placed with rubber stoppers inserted in the "lyophilization position" and loaded in the prechilled lyophilizer. For the lyophilizer, shelf temperature is set at +5° C. and held for 1 hour; shelf temperature is then adjusted to −5° C. and held for one hour, and the condenser, set to −60° C., turned on.

(5) The vials are then frozen to 30° C. or below and held for no less than 3 hours, typically 4 hours.

(6) Vacuum is then turned on, the shelf temperature is adjusted to −5° C., and primary drying is performed for 8 hours; the shelf temperature is again adjusted to −5° C. and drying is carried out for at least 5 hours.

(7) Secondary drying is started after the condenser (set at −60° C.) and vacuum are turned on. In secondary drying, the shelf temperature is controlled at +5° C. for 1 to 3 hours, typically 1.5 hours, then at 25° C. for 1 to 3 hours, typically 1.5 hours, and finally at 35-40° C. for at least 5 hours, typically for 9 hours, or until the product is completely dried.

(8) Break the vacuum with filtered inert gas (e.g., nitrogen). Stopper the vials in the lyophilizer.

(9) Vials are removed from the lyophilizer chamber and sealed with aluminum flip-off seals. All vials are visually inspected and labeled with approved labels.

In yet another alternative, the adaptation or improvement can be made by use of dosage kits and packaging. These can include alterations in the dosage forms, container/closure systems, or systems or methods to improve the accuracy of mixing and dosage preparation and presentation. The dosage kits and packaging can be selected from the group consisting of the use of amber vials to protect from light and the use of stoppers with specialized coatings to improve shelf-life stability.

In yet another alternative, the adaptation or improvement can be made by use of a drug delivery system. The drug delivery system can improve the potential attributes of a pharmaceutical product such as convenience, duration of effect, or reduction of toxicities. The drug delivery system can be selected from the group consisting of:

(a) nanocrystals;
(b) bioerodible polymers;
(c) liposomes;
(d) slow release injectable gels;
(e) microspheres;
(f) vascular disrupting agents; and
(g) polymer-coated stents.

Nanocrystals are described in U.S. Pat. No. 7,101,576 to Hovey et al., incorporated herein by this reference.

Bioerodible polymers are described in U.S. Pat. No. 7,318,931 to Okumu et al., incorporated herein by this reference. A bioerodible polymer decomposes when placed inside an organism, as measured by a decline in the molecular weight of the polymer over time. Polymer molecular weights can be determined by a variety of methods including size exclusion chromatography (SEC), and are generally expressed as weight averages or number averages. A polymer is bioerodible if, when in phosphate buffered saline (PBS) of pH 7.4 and a temperature of 37° C., its weight-average molecular weight is reduced by at least 25% over a period of 6 months as measured by SEC. Useful bioerodible polymers include polyesters, such as poly(caprolactone), poly(glycolic acid), poly(lactic acid), and poly(hydroxybutyrate); polyanhydrides, such as poly(adipic anhydride) and poly(maleic anhydride); polydioxanone; polyamines; polyamides; polyurethanes; polyesteramides; polyorthoesters; polyacetals; polyketals; polycarbonates; polyorthocarbonates; polyphosphazenes; poly(malic acid); poly(amino acids); polyvinylpyrrolidone; poly(methyl vinyl ether); poly(alkylene oxalate); poly(alkylene succinate); polyhydroxycellulose; chitin; chitosan; and copolymers and mixtures thereof.

Liposomes are well known as drug delivery vehicles. Liposome preparation is described in European Patent Application Publication No. EP 1332755 by Weng et al., incorporated herein by this reference.

Slow release injectable gels are known in the art and are described, for example, in B. Jeong et al., "Drug Release from Biodegradable Injectable Thermosensitive Hydrogel of PEG-PLGA-PEG Triblock Copolymers," *J. Controlled Release* 63: 155-163 (2000).

The use of microspheres for drug delivery is known in the art and is described, for example, in H. Okada & H. Taguchi, "Biodegradable Microspheres in Drug Delivery," *Crit. Rev. Ther. Drug Carrier Sys.* 12: 1-99 (1995), incorporated herein by this reference.

The use of vascular disrupting agents for delivery is disclosed in United States Patent Application Publication No. 2010/0272717 by Evans et al., incorporated herein by this reference. Such vascular disrupting agents include, but are not limited to, 5,6-dimethylxanthenone-4-acetic acid.

The use of polymer-coated stents for drug delivery is disclosed in U.S. Pat. No. 7,906,134 by Hauenstein, incorporated by this reference.

In yet another alternative, the adaptation or improvement can be made by use of a drug conjugate form. The drug conjugate form can involve alterations to the parent molecule with covalent, ionic, or hydrogen bonded moieties to alter the efficacy, toxicity, pharmacokinetics, metabolism, or route of administration. The drug conjugate form can be selected from the group consisting of:

(a) a polymer system;
(b) polylactides;
(c) polyglycolides;
(d) amino acids;
(e) peptides; and
(f) multivalent linkers.

Polylactide conjugates are well known in the art and are described, for example, in R. Tong & C. Cheng, "Controlled Synthesis of Camptothecin-Polylactide Conjugates and Nanoconjugates," *Bioconjugate Chem.* 21: 111-121 (2010), incorporated by this reference.

Polyglycolide conjugates are also well known in the art and are described, for example, in PCT Patent Application Publication No. WO 2003/070823 by Elmaleh et al., incorporated herein by this reference.

Multivalent linkers are known in the art and are described, for example, in United States Patent Application Publication No. 2007/0207952 by Silva et al., incorporated herein by this reference. For example, multivalent linkers can contain a thiophilic group for reaction with a reactive cysteine, and multiple nucleophilic groups (such as NH or OH) or electrophilic groups (such as activated esters) that permit attachment of a plurality of biologically active moieties to the linker.

Suitable reagents for cross-linking many combinations of functional groups are known in the art. For example, electrophilic groups can react with many functional groups, including those present in proteins or polypeptides. Various combinations of reactive amino acids and electrophiles are known in the art and can be used. For example, N-terminal cysteines, containing thiol groups, can be reacted with halogens or maleimides. Thiol groups are known to have reactivity with a large number of coupling agents, such as alkyl halides, haloacetyl derivatives, maleimides, aziridines, acryloyl derivatives, arylating agents such as aryl halides, and others. These are described in G. T. Hermanson, "Bioconjugate Techniques" (Academic Press, San Diego, 1996), pp. 146-150, incorporated herein by this reference. The reactivity of the cysteine residues can be optimized by appropriate selection of the neighboring amino acid residues. For example, a histidine residue adjacent to the cysteine residue will increase the reactivity of the cysteine residue. Other combinations of reactive amino acids and electrophilic reagents are known in the art. For example, maleimides can react with amino groups, such as the $\epsilon$-amino group of the side chain of lysine, particularly at higher pH ranges. Aryl halides can also react with such amino groups. Haloacetyl derivatives can react with the imidazolyl side chain nitrogens of histidine, the thioether group of the side chain of methionine, and the .epsilon.-amino group of the side chain of lysine. Many other electrophilic reagents are known that will react with the 8-amino group of the side chain of lysine, including, but not limited to, isothiocyanates, isocyanates, acyl azides, N-hydroxysuccinimide esters, sulfonyl chlorides, epoxides, oxiranes, carbonates, imidoesters, carbodiimides, and anhydrides. These are described in G. T. Hermanson, "Bioconjugate Techniques" (Academic Press, San Diego, 1996), pp. 137-146, incorporated herein by this reference. Additionally, electrophilic reagents are known that will react with carboxylate side chains such as those of aspartate and glutamate, such as diazoalkanes and diazoacetyl compounds, carbonyldimidazole, and carbodiimides. These are described in G. T. Hermanson, "Bioconjugate Techniques" (Academic Press, San Diego, 1996), pp. 152-154, incorporated herein by this reference. Furthermore, electrophilic reagents are known that will react with hydroxyl groups such as those in the side chains of serine and threonine, including reactive haloalkane derivatives. These are described in G. T. Hermanson, "Bioconjugate Techniques," (Academic Press, San Diego, 1996), pp. 154-158, incorporated herein by this reference. In another alternative embodiment, the relative positions of electrophile and nucleophile (i.e., a molecule reactive with an electrophile) are reversed so that the protein has an amino acid residue with an electrophilic group that is reactive with a nucleophile and the targeting molecule includes therein a nucleophilic group. This includes the reaction of aldehydes (the electrophile) with hydroxylamine (the nucleophile), described above, but is more general than that reaction; other groups can be used as electrophile and nucleophile. Suitable groups are well known in organic chemistry and need not be described further in detail.

Additional combinations of reactive groups for cross-linking are known in the art. For example, amino groups can be reacted with isothiocyanates, isocyanates, acyl azides, N-hydroxysuccinimide (NHS) esters, sulfonyl chlorides, aldehydes, glyoxals, epoxides, oxiranes, carbonates, alkylating agents, imidoesters, carbodiimides, and anhydrides. Thiol groups can be reacted with haloacetyl or alkyl halide derivatives, maleimides, aziridines, acryloyl derivatives, acylating agents, or other thiol groups by way of oxidation and the formation of mixed disulfides. Carboxy groups can be reacted with diazoalkanes, diazoacetyl compounds, carbonyldiimidazole, carbodiimides. Hydroxyl groups can be reacted with epoxides, oxiranes, carbonyldiimidazole, N,N'-disuccinimidyl carbonate, N-hydroxysuccinimidyl chloroformate, periodate (for oxidation), alkyl halogens, or isocyanates. Aldehyde and ketone groups can react with hydrazines, reagents forming Schiff bases, and other groups in reductive amination reactions or Mannich condensation reactions. Still other reactions suitable for cross-linking reactions are known in the art. Such cross-linking reagents and reactions are described in G. T. Hermanson, "Bioconjugate Techniques" (Academic Press, San Diego, 1996), incorporated herein by this reference.

In yet another alternative, the adaptation or improvement can be made by use of a compound analog. This can involve alterations to the parent structure of a molecule with additional chemical functionalities that may alter efficacy, or reduce toxicity, pharmacological performance, route of administration, or another relevant factor for therapeutic efficacy. The compound analog can be selected from the group consisting of:
  (a) alteration of side chains to increase or decrease lipophilicity;
  (b) addition of an additional chemical functionality to alter a property selected from the group consisting of reactivity, electron affinity, and binding capacity; and
  (c) alteration of salt form.

In yet another alternative, the adaptation or improvement can be made by use of a prodrug system. The use of a prodrug involves alterations to the molecule such that improved pharmaceutical performance is gained with a variant of the active molecule in that after introduction into the body a portion of the molecule is cleaved to reveal the preferred active molecule. The prodrug system can be selected from the group consisting of:
  (a) the use of enzyme sensitive esters;
  (b) the use of dimers;
  (c) the use of Schiff bases;
  (d) the use of pyridoxal complexes;
  (e) the use of caffeine complexes;
  (f) the use of products of reaction with an acylating or carbamylating agent;
  (g) the use of hexanoate conjugates;
  (h) the use of polymer-agent conjugates; and
  (i) the use of prodrugs that are subject to redox activation.

The use of prodrug systems is described in T. Järvinen et al., "Design and Pharmaceutical Applications of Prodrugs" in *Drug Discovery Handbook* (S. C. Gad, ed., Wiley-Interscience, Hoboken, N.J., 2005), ch. 17, pp. 733-796, incorporated herein by this reference. This publication describes the use of enzyme sensitive esters as prodrugs. The use of dimers as prodrugs is described in U.S. Pat. No. 7,879,896 to Allegretti et al., incorporated herein by this reference. The use of peptides in prodrugs is described in S. Prasad et al., "Delivering Multiple Anticancer Peptides as a Single Prodrug Using Lysyl-Lysine as a Facile Linker," *J. Peptide Sci.* 13: 458-467 (2007), incorporated herein by this reference. The use of Schiff bases as prodrugs is described in U.S. Pat. No. 7,619,005 to Epstein et al., incorporated herein by this reference. The use of caffeine complexes as prodrugs is described in U.S. Pat. No. 6,443,898 to Unger et al., incorporated herein by this reference.

Yet other prodrug systems applicable to dianhydrogalactitol, diacetyldianhydrogalactitol, dibromodulcitol, or their derivatives include prodrugs that are prepared by reacting a compound with an acylating or carbamylating agent, such as 1,1-acyloxyalkylcarbonochloridate, p-nitrophenyl carbonate, or a similar acylating or carbamylating agent, as described in U.S. Pat. No. 8,076,375 to Sefton et al.

Still other other prodrug systems applicable to dianhydrogalactitol, diacetyldianhydrogalactitol, dibromodulcitol, or their derivatives include hexanoate conjugates and polymer-agent conjugates as described in United States Patent Application Publication No. 2011/0268658 by Crawford et al., incorporated herein by this reference.

Still other prodrug systems applicable to dianhydrogalactitol, diacetyldianhydrogalactitol, dibromodulcitol, or their derivatives include the use of prodrugs that are subject to redox activation. This utilizes the large quantities of reductase enzyme present in a hypoxic cell to bioactivate the drug into its cytotoxic form, essentially activating it.

In general, prodrugs can be classified into two major types, based on their cellular sites of bioactivation into the final active drug form, with Type I being those that are bioactivated intracellularly (e.g., anti-viral nucleoside analogs, lipid-lowering statins), and Type II being those that are bioactivated extracellularly, especially in digestive fluids or the systemic circulation (e.g., etoposide phosphate, valganciclovir, fosamprenavir, antibody-gene- or virus-directed enzyme prodrugs [ADEP/GDEP/VDEP] for chemotherapy or immunotherapy). Both types can be further categorized into subtypes, i.e. Type IA, IB and Type IIA, IIB, and IIC based on whether or not the intracellular bioactivating location is also the site of therapeutic action, or the bioactivation occurs in the gastrointestinal (GI) fluids or systemic circulation. Type IA prodrugs include many antimicrobial and chemotherapy agents (e.g., 5-fluorouracil). Type IB agents rely on metabolic enzymes, especially in hepatic cells, to bioactivate the prodrugs intracellularly to active drugs. Type II prodrugs are bioactivated extracelluary, either in the milieu of GI fluids (Type IIA), within the systemic circulation and/or other extracellular fluid compartments (Type IIB), or near therapeutic target tissues/cells (Type IIC), relying on common enzymes such as esterases and phosphatases or target directed enzymes. Importantly, prodrugs can belong to multiple subtypes (i.e., mixed-type). A mixed-type prodrug is one that is bioactivated at multiple sites, either in parallel or sequential steps. Many ADEPs, VDEPs, GDEPs and nanoparticle- or nanocarrier-linked drug moieties can be sequential mixed-type prodrugs. Bioactivation of prodrugs can occur by many reactions, including bioactivation by esterases, hydrolysis, bioactivation by decarboxylases, bioactivation by phosphatases, bioactivation by deacetylases, bioactivation by N-dealkylases, and many other reactions.

In yet another alternative, the adaptation or improvement can be made by use of a multiple drug system. The use of a multiple drug system involves the use of additional compounds, biological agents that when administered in the proper fashion, a unique and beneficial effect can be realized. The multiple drug system can employ a mechanism selected from the group consisting of:

(a) use of multi-drug resistance inhibitors;
(b) use of specific drug resistance inhibitors;
(c) use of specific inhibitors of selective enzymes;
(d) use of signal transduction inhibitors;
(e) use of repair inhibition; and
(f) use of topoisomerase inhibitors with non-overlapping side effects.

Multi-drug resistance inhibitors are described in U.S. Pat. No. 6,011,069 to Inomata et al., incorporated herein by this reference.

Specific drug resistance inhibitors are described in T. Hideshima et al., "The Proteasome Inhibitor PS-341 Inhibits Growth, Induces Apoptosis, and Overcomes Drug Resistance in Human Multiple Myeloma Cells," *Cancer Res.* 61: 3071-3076 (2001), incorporated herein by this reference.

Repair inhibition is described in N. M. Martin, "DNA Repair Inhibition and Cancer Therapy," *J. Photochem. Photobiol. B* 63: 162-170 (2001), incorporated herein by this reference.

In yet another alternative, the adaptation or improvement can be made by use of biotherapeutic enhancement. This involves the use of therapeutically active compounds in combination as sensitizers/potentiators with biological response modifiers. The biotherapeutic enhancement can be performed by use in combination as sensitizers/potentiators with a therapeutic agent or technique selected from the group consisting of:

(a) cytokines;
(b) lymphokines;
(c) therapeutic antibodies;
(d) antisense therapies;
(e) gene therapies;
(f) ribozymes; and
(g) RNA interference.

Antisense therapies are described, for example, in B. Weiss et al., "Antisense RNA Gene Therapy for Studying and Modulating Biological Processes," *Cell. Mol. Life Sci.* 55: 334-358 (1999), incorporated herein by this reference.

Ribozymes are described, for example, in S. Pascolo, "RNA-Based Therapies" in *Drug Discovery Handbook* (S. C. Gad, ed., Wiley-Interscience, Hoboken, N.J., 2005), ch. 27, pp. 1273-1278, incorporated herein by this reference.

RNA interference is described, for example, in S. Pascolo, "RNA-Based Therapies" in *Drug Discovery Handbook* (S. C. Gad, ed., Wiley-Interscience, Hoboken, N.J., 2005), ch. 27, pp. 1278-1283, incorporated herein by this reference.

When the biotherapeutic enhancement is use in combination as sensitizers/potentiators with a therapeutic antibody, the therapeutic antibody can be, but is not limited to, a therapeutic antibody selected from the group consisting of bevacizumab (Avastin), rituximab (Rituxan), trastuzumab (Herceptin), and cetuximab (Erbitux).

In yet another alternative, the adaptation or improvement can be made by use of biotherapeutic resistance modulation. This involves exploiting their selective use to overcome developing or complete resistance to the efficient use of biotherapeutics. The biotherapeutic resistance modulation can comprise use against tumors resistant to a therapeutic agent or technique selected from the group consisting of:

(a) biological response modifiers;
(b) cytokines;
(c) lymphokines;
(d) therapeutic antibodies;
(e) antisense therapies;
(f) gene therapies;
(g) ribozymes; and
(h) RNA interference.

When the biotherapeutic resistance modulation is use against tumors resistant to therapeutic antibodies, the therapeutic antibody can be, but is not limited to, a therapeutic antibody selected from the group consisting of bevacizumab (Avastin), rituximab (Rituxan), trastuzumab (Herceptin), and cetuximab (Erbitux).

In yet another alternative, the adaptation or improvement can be made by use of radiation therapy enhancement. This involves their use in combination with ionizing radiation, phototherapies, heat therapies, or radio-frequency generated therapies. The radiation therapy enhancement can be performed by use of an agent or technique selected from the group consisting of:

(a) hypoxic cell sensitizers;
(b) radiation sensitizers/protectors;
(c) photosensitizers;
(d) radiation repair inhibitors;
(e) thiol depleters;
(f) vaso-targeted agents;
(g) DNA repair inhibitors;
(h) radioactive seeds;
(i) radionuclides;
(j) radiolabeled antibodies; and
(k) brachytherapy.

Hypoxic cell sensitizers are described in C. C. Ling et al., "The Effect of Hypoxic Cell Sensitizers at Different Irradiation Dose Rates," *Radiation Res.* 109: 396-406 (1987), incorporated herein by this reference. Radiation sensitizers are described in T. S. Lawrence, "Radiation Sensitizers and Targeted Therapies," *Oncology* 17 (Suppl. 13) 23-28 (2003), incorporated herein by this reference. Radiation protectors are described in S. B. Vuyyuri et al., "Evaluation of D-Methionine as a Novel Oral Radiation Protector for Prevention of Mucositis," *Clin. Cancer Res.* 14: 2161-2170 (2008), incorporated herein by this reference. Photosensitizers are described in R. R. Allison & C. H. Sibata, "Oncologic Photodynamic Therapy Photosensitizers: A Clinical Review," *Photodiagnosis Photodynamic Ther.* 7: 61-75 (2010), incorporated herein by this reference. Radiation repair inhibitors and DNA repair inhibitors are described in M. Hingorani et al., "Evaluation of Repair of Radiation-Induced DNA Damage Enhances Expression from Replication-Defective Adenoviral Vectors," *Cancer Res.* 68: 9771-9778 (2008), incorporated herein by this reference. Thiol depleters are described in K. D. Held et al., "Postirradiation Sensitization of Mammalian Cells by the Thiol-Depleting Agent Dimethyl Fumarate," *Radiation Res.* 127: 75-80 (1991), incorporated herein by this reference. Vaso-targeted agents are described in A. L. Seynhaeve et al., "Tumor Necrosis Factor α Mediates Homogeneous Distribution of Liposomes in Murine Melanoma that Contributes to a Better Tumor Response," *Cancer Res.* 67: 9455-9462 (2007).

In yet another alternative, the adaptation or improvement can be made by use of novel mechanisms of action. This involves optimizing their utility by determining the various mechanisms of action, biological targets of a compound for greater understanding and precision to better exploit the utility of the molecule. The novel mechanism of action can be a therapeutic interaction with a target or mechanism selected from the group consisting of:

(a) inhibitors of poly-ADP ribose polymerase;
(b) agents that affect vasculature or vasodilation;
(c) oncogenic targeted agents;
(d) signal transduction inhibitors;
(e) EGFR inhibition;
(f) protein kinase C inhibition;
(g) phospholipase C downregulation;
(h) Jun downregulation;
(i) histone genes;
(j) VEGF;
(k) ornithine decarboxylase;
(l) ubiquitin C;
(m) jun D;
(n) v-jun;
(o) GPCRs;
(p) protein kinase A;
(q) protein kinases other than protein kinase A;
(r) prostate specific genes;
(s) telomerase; and
(t) histone deacetylase.

EGFR inhibition is described in G. Giaccone & J. A. Rodriguez, "EGFR Inhibitors: What Have We Learned from the Treatment of Lung Cancer," *Nat. Clin. Pract. Oncol.* 11: 554-561 (2005), incorporated herein by this reference. Protein kinase C inhibition is described in N. C. Swannie & S. B. Kaye, "Protein Kinase C Inhibitors," *Curr. Oncol. Rep.* 4: 37-46 (2002), incorporated herein by this reference. Phospholipase C downregulation is described in A. M. Martelli et al., "Phosphoinositide Signaling in Nuclei of Friend Cells: Phospholipase C β Downregulation Is Related to Cell Differentiation," *Cancer Res.* 54: 2536-2540 (1994), incorporated herein by this reference. Downregulation of Jun (specifically, c-Jun) is described in A. A. P. Zada et al., "Downregulation of c-Jun Expression and Cell Cycle Regulatory Molecules in Acute Myeloid Leukemia Cells Upon CD44 Ligation," *Oncogene* 22: 2296-2308 (2003), incorporated herein by this reference. The role of histone genes as a target for therapeutic intervention is described in B. Calabretta et al., "Altered Expression of G1-Specific Genes in Human Malignant Myeloid Cells," *Proc. Natl. Acad. Sci. USA* 83: 1495-1498 (1986). The role of VEGF as a target for therapeutic intervention is described in A. Zielke et al., "VEGF-Mediated Angiogenesis of Human Pheochromocytomas Is Associated to Malignancy and Inhibited by anti-VEGF Antibodies in Experimental Tumors," *Surgery* 132: 1056-1063 (2002), incorporated herein by this reference. The role of ornithine decarboxylase as a target for therapeutic intervention is described in J. A. Nilsson et al., "Targeting Ornithine Decarboxylase in Myc-Induced Lymphomagenesis Prevents Tumor Formation," *Cancer Cell* 7: 433-444 (2005), incorporated herein by this reference. The role of ubiquitin C as a target for therapeutic intervention is described in C. Aghajanian et al., "A Phase I Trial of the Novel Proteasome Inhibitor PS341 in Advanced Solid Tumor Malignancies," *Clin. Cancer Res.* 8: 2505-2511 (2002), incorporated herein by this reference. The role of Jun D as a target for therapeutic intervention is described in M. M. Caffarel et al., "JunD Is Involved in the Antiproliferative Effect of $\Delta^9$-Tetrahydrocannibinol on Human Breast Cancer Cells," *Oncogene* 27: 5033-5044 (2008), incorporated herein by this reference. The role of v-Jun as a target for therapeutic intervention is described in M. Gao et al., "Differential and Antagonistic Effects of v-Jun and c-Jun," *Cancer Res.* 56: 4229-4235 (1996), incorporated herein by this reference. The role of protein kinase A as a target for therapeutic intervention is described in P. C. Gordge et al., "Elevation of Protein Kinase A and Protein Kinase C in Malignant as Compared With Normal Breast Tissue," *Eur. J. Cancer* 12: 2120-2126 (1996), incorporated herein by this reference. The role of telomerase as a target for therapeutic intervention is described in E. K. Parkinson et al., "Telomerase as a Novel and Potentially Selective Target for Cancer Chemotherapy," *Ann. Med.* 35: 466-475 (2003), incorporated herein by this reference. The role of histone deacetylase as a target for therapeutic intervention is described in A. Melnick & J. D. Licht, "Histone Deacetylases as Therapeutic Targets in Hematologic Malignancies," *Curr. Opin. Hematol.* 9: 322-332 (2002), incorporated herein by this reference.

In yet another alternative, the adaptation or improvement can be made by use of selective target cell population therapeutics. This can involve more precise identification and exposure of the compound to those select cell populations where the compound's effect can be maximally exploited. The use of selective target cell population therapeutics can be a use selected from the group consisting of:

(a) use against radiation sensitive cells;
(b) use against radiation resistant cells;
(c) use against energy depleted cells; and
(d) use against endothelial cells.

Another aspect of the present invention is a composition to improve the efficacy and/or reduce the side effects of a veterinary application of drug therapy comprising an alternative selected from the group consisting of:

(i) a therapeutically effective quantity of a modified therapeutic agent or a derivative, analog, or prodrug of a therapeutic agent or modified therapeutic agent, wherein the modified therapeutic agent or the derivative, analog or prodrug of the therapeutic agent or modified therapeutic agent possesses increased therapeutic efficacy or reduced side effects as compared with an unmodified therapeutic agent;

(ii) a composition comprising:
  (a) a therapeutically effective quantity of a therapeutic agent, a modified therapeutic agent or a derivative, analog, or prodrug of a therapeutic agent or modified therapeutic agent; and
  (b) at least one additional therapeutic agent, therapeutic agent subject to chemosensitization, therapeutic agent subject to chemopotentiation, diluent, excipient, solvent system, or drug delivery system, wherein the composition possesses increased therapeutic efficacy or reduced side effects as compared with an unmodified therapeutic agent;

(iii) a therapeutically effective quantity of a therapeutic agent, a modified therapeutic agent, or a derivative, analog, or prodrug of a therapeutic agent or modified therapeutic agent that is incorporated into a dosage form, wherein the therapeutic agent, the modified therapeutic agent, or the derivative, analog, or prodrug of a therapeutic agent or modified therapeutic agent incorporated into the dosage form possesses increased therapeutic efficacy or reduced side effects as compared with an unmodified therapeutic agent;

(iv) a therapeutically effective quantity of a therapeutic agent, a modified therapeutic agent, or a derivative, analog, or prodrug of a therapeutic agent or modified therapeutic agent that is incorporated into a dosage kit and packaging, wherein the therapeutic agent, the modified therapeutic agent, or the derivative, analog, or prodrug of a therapeutic agent or modified therapeutic agent incorporated into the dosage kit and packaging possesses increased therapeutic efficacy or reduced side effects as compared with an unmodified therapeutic agent; and (v) a therapeutically effective quantity of a therapeutic agent, a modified therapeutic agent, or a derivative, analog, or prodrug of a therapeutic agent or modified therapeutic agent that is subjected to a bulk drug product improvement, wherein the therapeutic agent, the modified therapeutic agent, or the derivative, analog, or prodrug of a therapeutic agent or modified therapeutic agent subject to the bulk drug product improvement possesses increased therapeutic efficacy or reduced side effects as compared with an unmodified therapeutic agent;

wherein the therapeutic agent is selected from the group consisting of dianhydrogalactitol, diacetyldianhydrogalactitol, and dibromodulcitol;

wherein the modified therapeutic agent is a modified form of a therapeutic agent selected from the group consisting of dianhydrogalactitol, diacetyldianhydrogalactitol, and dibromodulcitol; and wherein the derivative, analog, or prodrug of a therapeutic agent or modified therapeutic agent is a derivative, analog, or prodrug of a therapeutic agent selected from the group consisting of dianhydrogalactitol, diacetyldianhydrogalactitol, and dibromodulcitol, and a modified form of dianhydrogalactitol, diacetyldianhydrogalactitol, or dibromodulcitol.

In one alternative of a composition according to the present invention, the composition can comprise a drug combination comprising:

(i) a therapeutic agent selected from the group consisting of dianhydrogalactitol, diacetyldianhydrogalactitol, and dibromodulcitol; and (ii) an additional therapeutic agent selected from the group consisting of:
  (a) topoisomerase inhibitors;
  (b) fraudulent nucleosides;
  (c) fraudulent nucleotides;
  (d) thymidylate synthetase inhibitors;
  (e) signal transduction inhibitors;
  (f) cisplatin or platinum analogs;
  (g) alkylating agents;
  (h) anti-tubulin agents;
  (i) antimetabolites;
  (j) berberine;
  (k) apigenin;
  (l) amonafide;
  (m) vinca alkaloids;
  (n) 5-fluorouracil;
  (o) curcumin;
  (p) NF-κB inhibitors;
  (q) rosmarinic acid;
  (r) mitoguazone; and
  (s) tetrandrine.

In another alternative, the composition can comprise:
(i) a therapeutic agent selected from the group consisting of dianhydrogalactitol, diacetyldianhydrogalactitol, and dibromodulcitol; and (ii) a therapeutic agent subject to chemosensitization selected from the group consisting of:
  (a) topoisomerase inhibitors;
  (b) fraudulent nucleosides;
  (c) fraudulent nucleotides;
  (d) thymidylate synthetase inhibitors;
  (e) signal transduction inhibitors;
  (f) cisplatin or platinum analogs;
  (g) alkylating agents;
  (h) anti-tubulin agents;
  (i) antimetabolites;
  (j) berberine;
  (k) apigenin;
  (l) amonafide;
  (m) vinca alkaloids;
  (n) 5-fluorouracil;
  (o) curcumin;
  (p) NF-κB inhibitors;
  (q) rosmarinic acid;
  (r) mitoguazone; and
  (s) tetrandrine;

wherein the therapeutic agent selected from the group consisting of dianhydrogalactitol, diacetyldianhydrogalactitol, and dibromodulcitol acts as a chemosensitizer.

In yet another alternative, the composition comprises:
(i) a therapeutic agent selected from the group consisting of dianhydrogalactitol, diacetyldianhydrogalactitol, and dibromodulcitol; and (ii) a therapeutic agent subject to chemopotentiation selected from the group consisting of:
  (a) topoisomerase inhibitors;
  (b) fraudulent nucleosides;
  (c) fraudulent nucleotides;
  (d) thymidylate synthetase inhibitors;
  (e) signal transduction inhibitors;
  (f) cisplatin or platinum analogs;
  (g) alkylating agents;
  (h) anti-tubulin agents;
  (i) antimetabolites;
  (j) berberine;
  (k) apigenin;
  (l) amonafide;
  (m) vinca alkaloids;
  (n) 5-fluorouracil;
  (o) curcumin;
  (p) NF-κB inhibitors;
  (q) rosmarinic acid;
  (r) mitoguazone;
  (s) tetrandrine; and
  (t) biotherapeutics;

wherein the therapeutic agent selected from the group consisting of dianhydrogalactitol, diacetyldianhydrogalactitol, and dibromodulcitol; acts as a chemopotentiator.

In yet another alternative of a composition according to the present invention, the therapeutic agent is dianhydrogalactitol, diacetyldianhydrogalactitol, or dibromodulcitol, and the dianhydrogalactitol, diacetyldianhydrogalactitol, or dibromodulcitol is subjected to a bulk drug product improvement, wherein the bulk drug product improvement is selected from the group consisting of:
  (a) salt formation;
  (b) preparation as a homogeneous crystal structure;
  (c) preparation as a pure isomer;
  (d) increased purity;
  (e) preparation with lower residual solvent content; and
  (f) preparation with lower residual heavy metal content.

In still another alternative of a composition according to the present invention, the therapeutic agent is dianhydrogalactitol, diacetyldianhydrogalactitol, or dibromodulcitol and the composition comprises a diluent, wherein the diluent is selected from the group consisting of:
(a) an emulsion;
(b) dimethylsulfoxide (DMSO);
(c) N-methylformamide (NMF)
(d) DMF;
(e) ethanol;
(f) benzyl alcohol;
(g) dextrose-containing water for injection;
(h) Cremophor;
(i) cyclodextrin; and
(j) PEG.

In still another alternative of a composition according to the present invention, the therapeutic agent is dianhydrogalactitol, diacetyldianhydrogalactitol, or dibromodulcitol and the composition comprises a solvent system, wherein the solvent system is selected from the group consisting of:
(a) an emulsion;
(b) dimethylsulfoxide (DMSO);
(c) N-methylformamide (NMF);
(d) DMF;
(e) ethanol;
(f) benzyl alcohol;
(g) dextrose-containing water for injection;
(h) Cremophor;
(i) cyclodextrin; and
(j) PEG.

In still another alternative of a composition according to the present invention, the therapeutic agent is dianhydrogalactitol, diacetyldianhydrogalactitol, or dibromodulcitol and the composition comprises an excipient, wherein the excipient is selected from the group consisting of:
(a) mannitol;
(b) albumin;
(c) EDTA;
(d) sodium bisulfite;
(e) benzyl alcohol;
(f) a carbonate buffer; and
(g) a phosphate buffer.

In still another alternative of a composition according to the present invention, the therapeutic agent is dianhydrogalactitol, diacetyldianhydrogalactitol, or dibromodulcitol, and the dianhydrogalactitol, diacetyldianhydrogalactitol, or dibromodulcitol is incorporated into a dosage form suitable for veterinary use selected from the group consisting of:
(a) tablets;
(b) capsules;
(c) topical gels;
(d) topical creams;
(e) patches;
(f) suppositories; and
(g) lyophilized dosage fills.

In still another alternative of a composition according to the present invention, the therapeutic agent is dianhydrogalactitol, diacetyldianhydrogalactitol, or dibromodulcitol and the dianhydrogalactitol, diacetyldianhydrogalactitol, or dibromodulcitol is incorporated into a dosage kit and packaging selected from the group consisting of amber vials to protect from light and stoppers with specialized coatings to improve shelf-life stability.

In still another alternative of a composition according to the present invention, the therapeutic agent is dianhydrogalactitol, diacetyldianhydrogalactitol, or dibromodulcitol, and the composition comprises a drug delivery system selected from the group consisting of:
(a) nanocrystals;
(b) bioerodible polymers;
(c) liposomes;
(d) slow release injectable gels; and
(e) microspheres.

In still another alternative of a composition according to the present invention, the therapeutic agent is dianhydrogalactitol, diacetyldianhydrogalactitol, or dibromodulcitol, and the dianhydrogalactitol, diacetyldianhydrogalactitol, or dibromodulcitol is present in the composition in a drug conjugate form selected from the group consisting of:
(a) a polymer system;
(b) polylactides;
(c) polyglycolides;
(d) amino acids;
(e) peptides; and
(f) multivalent linkers.

In yet another alternative of a composition according to the present invention, the therapeutic agent is a modified dianhydrogalactitol, a modified diacetyldianhydrogalactitol, or a modified dibromodulcitol, and the modification is selected from the group consisting of:
(a) alteration of side chains to increase or decrease lipophilicity;
(b) addition of an additional chemical functionality to alter a property selected from the group consisting of reactivity, electron affinity, and binding capacity; and
(c) alteration of salt form.

In yet another alternative of a composition according to the present invention, the therapeutic agent is dianhydrogalactitol, diacetyldianhydrogalactitol, or dibromodulcitol, and the dianhydrogalactitol, diacetyldianhydrogalactitol, or dibromodulcitol is in the form of a prodrug system, wherein the prodrug system is selected from the group consisting of:
(a) the use of enzyme sensitive esters;
(b) the use of dimers;
(c) the use of Schiff bases;
(d) the use of pyridoxal complexes;
(e) the use of caffeine complexes;
(f) the use of products of reaction with an acylating or carbamylating agent;
(g) the use of hexanoate conjugates;
(h) the use of polymer-agent conjugates; and
(i) the use of prodrugs that are subject to redox activation.

In still another alternative of a composition according to the present invention, the therapeutic agent is dianhydrogalactitol, diacetyldianhydrogalactitol, or dibromodulcitol, and the composition further comprises at least one additional therapeutic agent to form a multiple drug system, wherein the at least one additional therapeutic agent is selected from the group consisting of:
(a) an inhibitor of multi-drug resistance;
(b) a specific drug resistance inhibitor;
(c) a specific inhibitor of a selective enzyme;
(d) a signal transduction inhibitor;
(e) an inhibitor of a repair enzyme; and
(f) a topoisomerase inhibitor with non-overlapping side effects.

When a pharmaceutical composition according to the present invention includes a prodrug, prodrugs and active metabolites of a compound may be identified using routine techniques known in the art. See, e.g., Bertolini et al., J. Med. Chem., 40, 2011-2016 (1997); Shan et al., J. Pharm. Sci., 86 (7), 765-767; Bagshawe, Drug Dev. Res., 34, 220-230 (1995); Bodor, Advances in Drug Res., 13, 224-331 (1984); Bundgaard, Design of Prodrugs (Elsevier Press 1985); Larsen, Design and Application of Prodrugs, Drug Design and Development (Krogsgaard-Larsen et al., eds., Harwood Academic Publishers, 1991); Dear et al., J. Chromatogr. B, 748, 281-293 (2000); Spraul et al., J. Pharmaceutical & Biomedical Analysis, 10, 601-605 (1992); and Prox et al., Xenobiol., 3, 103-112 (1992).

When the pharmacologically active compound in a pharmaceutical composition according to the present invention possesses a sufficiently acidic, a sufficiently basic, or both a sufficiently acidic and a sufficiently basic functional group, these group or groups can accordingly react with any of a number of inorganic or organic bases, and inorganic and organic acids, to form a pharmaceutically acceptable salt. Exemplary pharmaceutically acceptable salts include those salts prepared by reaction of the pharmacologically active compound with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenylbutyrates, citrates, lactates, β-hydroxybutyrates, glycolates, tartrates, methane-sulfonates, propanesulfonates, naphthalene-1-sulfonates, naphthalene-2-sulfonates, and mandelates. If the pharmacologically active compound has one or more basic functional groups, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the pharmacologically active compound has one or more acidic functional groups, the desired pharmaceutically acceptable salt may be prepared by any suitable method available in the art, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

The invention is illustrated by the following Examples. These examples are for illustrative purposes only and are not intended to limit the invention.

Example 1

Pharmacologic and Antitumor Effects of Dianhydrogalactitol

This example is based on the procedures and results described in L. Németh et al., "Pharmacologic and Antitumor Effects of 1,2:5,6-Dianhydrogalactitol (NSC-132313)," *Cancer Chemother. Rep. Part* 1 56: 593-602 (1972), incorporated herein by this reference.

The diepoxy derivatives formed in alkaline medium from dibromohexitols, compounds with known cytostatic activity, are the possible cause of the antitumor activity of these terminally substituted hexitols (L. Institóris et al., "Investigation Into the Correlation of Cytostatic Activity With the in Vitro Diepoxide Formation on Some Terminally Substituted Hexitols," *Neoplasma* 17: 15-24 (1970); L. A. Elson et al., "Toxicity, Haematological Effects and Antitumour Activity of Epoxides Derived From Disubstituted Hexitols," *Eur. J. Cancer* 4: 617-625 (1968)). 1,2:5,6-Dianhydrogalactitol ("dianhydrogalactitol") is the most chemically stable of all the diepoxyhexitols, and it exerts the most pronounced biologic effects (B. Kellner et al., "Antitumoral Effect of Dulcitoldiepoxide (1,2-5,6-Dianhydrogalacitol, NSC 132313," Int. Congr. Chemother. 7$^{th}$ Congr, Prague 1971).

Materials and Methods

Dianhydrogalactitol was synthesized according to the method described in Elson et al., supra. It was dissolved in isotonic saline and was administered intravenously (i.v.) or intraperitoneally (i.p.). In distilled water the solution had a slight, locally irritating effect. Dibromodulcitol is hardly soluble in water; therefore, an 0.5% carboxymethylcellulose-containing homogenate was prepared and injected either i.v. or i.p.

Animals

For L1210 mouse leukemia studies, first generation hybrids of BDF$_1$ mice weighing 20-22 g were used; for the other mouse tumor studies, outbred Swiss mice weighing 25-30 g were used. Rat tumors were maintained in Wistar/Cbi outbred and WOP inbred rats weighing 150-200 g.

Acute Toxicity Experiments

After a single dose of either dianhydrogalactitol (12-20 mg/kg) or dibromodulcitol (70-1000 mg/kg) had been given to mice the survivors were observed for 21 days. The LD50s were determined by the method of Litchfield and Wilcoxon (J. T. Litchfield, Jr. & F. Wilcoxon, "A Simplified Method of Evaluating Dose-Effect Experiments," *J. Pharmacol. Exp. Ther.* 96: 99-113 (1949)). The toxic accumulations of the drug were calculated from the formula:

$$100(d_3-d_2)-d_4/d_1-d_4=\% \text{ residue}$$

where: $d_1$=number of deaths after a dose of 18 mg/kg (LD80); $d_2$=number of deaths after a dose of 9 mg/kg (one-half the LD80); $d_3$=number of deaths after two doses, each 9 mg/kg (one-half the LD80); and $d_4$=number of deaths among control animals.

Chronic Toxicity Experiments

In the chronic toxicity experiments, rabbits were treated with dianhydrogalactitol given i.v. at two different dose levels every second day for 30 or 70 days. The dose levels were 2.5 and 0.25 mg/kg. The animals were killed after the 15$^{th}$ treatment (for animals treated for 30 days) or after the 35$^{th}$ treatment (for articles treated for 70 days). Every two weeks, blood cell counts were done, and at the end of treatments histologic evaluations of all organs were performed.

Tissue Culture Studies

The cytomorphologic effects of dianhydrogalactitol were studied on HeLa cell cultures. For dose-survival experiments, Barle's L cells were treated with different doses of the drug. Chromosome-damaging effects were examined in Chinese hamster cell cultures. The mitotic index was determined by counting the number of mitoses in 1000 cells.

Histologic Studies

The sequential pattern of morphologic changes was studied in rats that had received subcutaneous (sc) tumor implantation with Guerin carcinoma cells when they were 14 days old. The studies were carried out from 1 hour to 21 days after the rats had received either a single 10 mg/kg dose (LD50), a single 5 mg/kg dose (one-half LD50), or a single 2.5 mg/kg dose (one-quarter LD50) of dianhydrogalactitol. After the treatment the animals were killed and histopathologic and cytologic alterations were investigated in the tumor, liver, spleen, kidneys, adrenal glands, duodenum, lymph nodes, and bone marrow. The alterations observed in these rats were compared to those observed in the rabbits used in the chronic toxicity tests.

Electron Microscopic Studies

A single dose of 3.7 mg/kg (one-quarter LD50) or 7.5 mg/kg (one-half LD50) of dianhydrogalactitol was administered intraperitoneally to mice bearing the Ehrlich ascites tumor 6 days after tumor transplantation. The animals were killed successively 1-144 hours after the treatment. The ascitic fluid was fixed in 2.5% glutaraldehyde and 1% osmium tetroxide according to the method of Sabatini et al. (P. D. Sabatini et al., "Aldehyde Fixation for Morphological and Enzyme Histochemical Studies with the Electronmicroscope," *J. Histochem. Cytochem.* 12: 57-62 (1964)). The material was embedded in Durcupan (ACM Fluka). The ultrathin sections were contrasted with lead citrate.

Hematologic Studies

The hematologic effects of dianhydrogalactitol were studied in one group of rabbits after single 14.0-mg/kg doses (LD50) and in additional groups of rabbits after 17×2.5- and 17×0.25-mg/kg doses (four rabbits per dose level). All doses were administered intravenously. The blood cell counts and smears were studied for 4 weeks.

Antitumor and Survival Time Studies

Five strains of mouse tumors and five strains of rat tumors were used for the evaluation of tumor response and increase in lifespan. For studies with L1210 leukemia, $10^6$ ascitic or spleen cells were transplanted intraperitoneally or subcutaneously, respectively. Treatment was started 24 hours (early) or, in a few experiments, 4 days (advanced) after tumor transplantation. The NK/Ly and Ehrlich ascites tumors were transplanted intraperitoneally using $5×10^6$ cells. The rat tumors were transplanted intravenously using $0.5$–$3.0×10^6$ cells. In studies of tumor growth inhibition, the animals were killed 8-15 days after tumor transplantation and the tumors were measured. In studies of increases in lifespan, observation was stopped when the treated animals had survived four times as long as the control animals.

Results

Toxicity Studies

In the animals treated with the LD50 of dianhydrogalactitol (15 mg/kg), the gastrointestinal symptoms (including weight loss) were dominant. These symptoms are characteristic of alkylating agents. Atrophy of the spleen and lymph nodes was more marked after treatment with dianhydrogalactitol than after treatment with dibromodulcitol.

The animals treated with dianhydrogalactitol died earlier than those treated with dibromodulcitol.

The toxic accumulations of dianhydrogalactitol were small. 48 hours after the start of treatment 45% of the drug had accumulated, and 96 hours after the start of the treatment no drug was detectable.

These and previous studies had shown that after the start of treatment the drug accumulation of five cytostatic hexitol derivatives was 0% for dianyhdrogalactitol, 62% for dibromodulcitol, 20% for dibromomannitol, 25% for mannitol mustard, and 45% for mannitol myleran.

In chronic toxicity experiments in rabbits the most marked alterations were cell population reductions (especially of the myeloid elements) in the bone marrow. Decreased blast cells and some cells with pyknotic nuclei were observed. No severe toxic changes of the organs were noted.

Tissue Culture Studies

The mitotic index of untreated control HeLa cultures was 2.9%. A 10-μg dose of dibromodulcitol decreased the mitotic index to 0, and a 100-μg dose of dianhydrogalactitol caused complete cellular disintegration. The cloning efficiency of untreated cells varied between 60% and 80%. The cloning efficiency of treated cells is expressed in terms of the percentage of the 100% control values. The curve of dianhydrogalactitol-treated cultures is rather steep between 1 and 10 μg/ml. In the case of dibromodulcitol, only the first part of the curve is steep; it then becomes less steep and linear. 50 percent survival was obtained when 4 μg/ml of dianhydrogalactitol or 75 μg/ml of dibromodulcitol was given.

The cytomorphologic effects of dianhydrogalactitol were characterized by various mitotic abnormalities, such as irregular arrangement of chromosomes, frequently resembling multipolar mitosis. In heavily damaged cells, chromosomes were clumped into a dense mass and extra-chromosomal parts contained granules. 48 hours after treatment cells were considerably enlarged, and 24 hours later multinucleate cells were found.

Low doses of dianhydrogalactitol induced characteristic chromosome aberrations in a number of Chinese hamster cells in vitro, e.g., chromatid and isochromatid breaks and gaps, acentric and dicentric chromosomes, and a wide range of symmetric and asymmetric exchanges. Chromosome fragmentation showed heavy cell damage. Chromosomal translocations were frequently noted.

Histologic Studies

Mitotic alterations appeared soon after the start of treatment with dianhydrogalactitol and were long lasting. This was demonstrated in all organs, but especially in the tumor, where, due to small doses, there was an increase in malformed mitoses and a large number of pyknomitoses.

Severe alterations were observed in an increasing number of mitoses 24-48 hours after the start of treatment. The most marked effect appeared after 72-96 hours when every second cell was dividing. During the early mitotic alterations no polyploid cells were present; however, later there were giant cells with a large number of chromosomes. There was an increase in the number of giant cells after treatment with dianhydrogalactitol, but the increase was not as large as in the case of treatment with mannitol mustard or dibromodulcitol. Along with the increase in the number of giant cells the necrotic areas increased but never to an extreme degree. Expressed desmoplastic activity was not observed.

Soon after the start of treatment pyknotic cell decay dominated the duodenum followed by reticulohistiocytic phagocytosis of the debris. First the goblet cells and the mitoses increased in the crypts and tubules; later, the mitotic figures suddenly disappeared. The marked lymphoid infiltration altered the structure of the duodenum, and the villi were flattened and deformed.

There was a reduction in the number of myeloid cells in the bone marrow. There was an increase in the number of reticular cells, and dilated sinusoids were filled with blood. Pyknotic changes appeared on the nuclei of the megakaryocytes. Diffuse repopulation occurred and later (72-96 hours) it became focal.

The early drug response in the spleen resulted in a decay of the lymphoid cells in the malpighian follicles. The phagocytosis of the debris by reticulum cells occurred first at the follicles and later in the pulp. Soon after treatment (6-12 hours) the lining cells of the sinusoids were destroyed, and the pulp became poorly populated and hyperemic; a few plasma cells, myeloid cells, and swollen, pigment-containing reticulum cells appeared. After larger doses or longer times from the start of treatment (24-48 hours), the pulp became empty and the reticular cells were prominent. Soon after this, repopulation started.

In the lymph nodes, the alterations were similar to those of the spleen. Three hours after treatment, cell decay appeared in the follicles and phagocytosis of the debris by reticulum cells occurred. The process was short-lived and after 48 hours there were only traces of it.

No changes in the parenchymal organs could be observed.

Electron Microscopic Studies: Effect on the Ultrastructure of Ehrlich Ascites Tumor Cells The effects at the ultrastructural level of single 3.7- and 7.5 mg/kg doses and dianhydrogalactitol were studied in animals bearing the Ehrlich ascites tumor. Treatment with larger doses proved to be more effective.

The nucleus and cytoplasm were damaged by treatment with the larger dose of the drug. The earliest effects could be detected 3 hours after administration. The matrix of the mitochondria disappeared and the cristae and mitochondrial membranes were fragmented. A more marked effect could be seen 48-72 hours after the administration of the drug. The ribosomes were detruded from the surface of the endoplasmic reticulum, and aggregates were formed by the free ribosomes. The small vesiculi of the smooth endoplasmic reticulum increased.

After 3 hours, various nuclear alterations occurred; the chromatin substance was loosened and decreased, the compact nucleoli disappeared, and a marked electron-dense spottedness was observed (K. Lapis & L. Benedeczky, "Antimetabolite-Induced Changes in the Fine Structure of Tumour Cells," *Acta Biol. Acad. Sci. Hung.* 17: 199-215 (1966)). Eight to ten electron-dense granules (0.1 μm-0.3 μm in diameter) could be seen arranged in groups in the nucleoplasm, some of which exceeded the size of the perichromatinic granules. These granules were located near the interchromatinic granules and were presumably formed by the clotting of those granules. The formation of such granules was not observed after other chemotherapeutic agents had been given. Multinucleated cells were detected more frequently after dianhydrogalactitol treatment than after treatment with other alkylating agents such as mannitol mustard or dibromodulcitol.

The effect of smaller doses could only be detected 72-96 hours after treatment. At that time, marked mitochondrial alterations were seen.

The effect of dianhydrogalactitol on the ultrastructure of tumor cells is reminiscent of that of other alkylating agents.

Hematologic Effects

After a single large dose (14.0 mg/kg) of dianhydrogalactitol in rabbits, marked reactive leukocytosis occurred, followed by a 50% decrease in the granulocyte count which disappeared in 30 days. The number of lymphocytes was similarly reduced, although regeneration occurred earlier (Day 13) when temporary lymphocytosis occurred. After this large dose had been given persistent thromobocytopenia occurred.

The animals receiving repeated injections of smaller doses showed moderate lymphoid responses and more severe myeloid responses, although no changes in platelet counts were noted.

Antitumor and Survival Time Studies

The effect on survival time with dianhydrogalactitol administration for mice with L1210 leukemia compared to the effects of other alkylating agents was studied. Various doses of dianhydrogalactitol prolonged the lifespan of animals with the early form of L1210 leukemia by 50%-200%, while dibromodulcitol showed 40% efficacy in this system. Dianhydrogalactitol surpassed the effects of other known related compounds; however, dibromodulcitol also showed a substantial lifespan increase.

The treatment of NK/Ly tumor-bearing mice with dianhydrogalactitol resulted in a 200% increase in lifespan. Dibromodulcitol produced a 90% prolongation in lifespan in this system.

Fifty percent of the animals with Ehrlich and S180 ascites tumors recovered after treatment with dianhydrogalactitol. Small doses of the drug (0.75 mg/kg; one-sixtieth of the LD50) caused a 68% tumor weight inhibition in the animals with Ehrlich ascites tumor; equitoxic doses of dibromodulcitol caused no effects on the same tumor. In Harding-Passey melanoma, dibromodulcitol was more effective than dianhydrogalactitol.

Both drugs had a marked effect on the ascitic form of the DMBA-induced myelocytic leukemia in rats and on rat leukemia injected with spleen and liver cells from leukemia-bearing animals.

Discussion

Dibromomannitol and dibromodulcitol are cytostatic drugs which have characteristic activity on blood cells. In addition, they inhibit the growth of several transplantable animal tumors. Dibromodulcitol has been used with success in busulfan-refractory chronic myelogenous leukemia and also in the treatment of polycythemia and several solid tumors.

Dibromodulcitol has been shown to undergo several biotransformational reactions in the organism, in the course of which epoxides are formed which are partly responsible for the antitumor activity (Institóris et al., supra). Dianhydrogalactitol has proven to be of more interest because of its stability, water solubility, and significant biological activity.

Example 2

Pharmacokinetics of Dianhydrogalactitol Disposition in the Dog

This example is based on the procedures and results described in T. Kimura et al., "A Preliminary Pharmacokinetic Study of Dianhydrogalactitol (NSC-132313) Disposition in the Dog," *J. Natl. Cancer Inst.* 58: 1311-1314 (1977), incorporated herein by this reference.

Dianhydrogalactitol is a hexitol diepoxide that has been evaluated for use in the treatment of cancers of the central nervous system, among other potential clinical uses. Geran et al. (R. I. Geran et al., "A Mouse Ependymoblastoma as an Experimental Model for Screening Potential Antineoplastic Drugs," *Cancer Chemother. Rep.* 4: 53-87 (1974) demonstrated the activity of dianhydrogalactitol against intracerebral murine ependymoblastomas. These observations have been corroborated by Levin et al. (V. A. Levin et al., "Dianhydrogalactitol (NSC-132313): Pharmacokinetics in Normal and Tumor-Bearing Rat Brain and Antitumor Activity Against Three Intracerebral Rodent Tumors," *J. Natl. Cancer Inst.* 56: 535-539 (1976)) who showed that dianhydrogalactitol rapidly crosses the blood-brain barrier and enters normal brain and intracerebral tumor tissue where it appears to nonspecifically alkylate nucleic acid residues.

Preliminary investigations on the pharmacokinetic disposition of dianhydrogalactitol were performed in the mouse (L. Institóris et al., "Comparative Studies on the in Vivo Distribution Pattern of Dibromodulcitol and Diepoxydulcitol," *Z. Krebsforsch.* 79: 49-59 (1973)) and rat (Levin et al., supra) with the use of radiolabeled drug. Drug disposition was determined by measurement of the total intensity of radioactivity in various body fluids as a function of time. Although such methods provide quantitative indications of drug disposition, they are nonspecific in that they fail to distinguish between parent drug, metabolites, and products formed by reaction of the epoxides with tissue nucleophiles. Quantitative conclusions arrived at from these studies, therefore, can be misleading and may not provide true indications of drug distribution. A gas chromatographic method has been developed for the specific determination and quantitation of submicrogram levels of dianhydrogalactitol in plasma (T. Kimura et al., "Gas Chromatographic Analysis of 1,2:5,6-Dianhydrogalactitol in Blood," *Clin. Chem.* 22: 1639-1643 (1976)). This method has now been applied to a determination of pharmacokinetic parameters associated with dianhydrogalactitol disposition in the dog from time-plasma level decay curves.

Materials and Methods
Pharmacokinetic Methods

Two unanesthetized beagle dogs were used. They were fasted overnight before they were given the drug intravenously in 4-5 ml of isotonic saline solution via the jugular vein over a period of 4-5 minutes. Dog 1, a female weighing 14.0 kg, was given dianhydrogalactitol (3 mg/kg) on day 1. Blood samples (5 ml) were taken from jugular veins prior to drug administration and at 5, 10, 15, 20, 30, 45, 75, 90, and 120 minutes after administration. Coagulation of whole blood samples was impaired by the addition of 0.7 ml of citrate-phosphate-dextrose solution (USP XIX). The blood samples were then centrifuged, and the plasma was removed, placed into test tubes, and kept frozen until analyzed. All analyses were carried out within 24 hours. Dog 2, a male weighing 10.5 kg, was given dianhydrogalactitol (6 mg/kg) on day 3. Blood samples (5 ml) were taken at 0, 3, 7.5, 10, 15, 20, 30, 45, 60, 75, 90, and 120 minutes and treated as described above. On day 8, dog 1 (at that time weighing 13.0 kg) was administered dianhydrogalactitol (6 mg/kg) and 5-ml blood samples were taken at similar time intervals and treated as previously described.

Analysis

To a 1-ml sample of plasma, 10 ml of isopropanol-chloroform (9:1) was added. The mixture was shaken for 15 minutes, after which 1 g of anhydrous potassium carbonate was added. The mixture was again shaken for 15 minutes and centrifuged, revealing a biphasic system. A 9-ml sample of the organic phase was removed and evaporated to dryness on a rotary evaporator. The residue was dissolved in 100 µl of an acetone solution containing 250 µg of n-butaneboronic acid and 0.5-5.0 µg of TMS-erythritol (serving as an internal standard). The mixtures were allowed to stand at room temperature for 5 minutes, after which a 2- to 8-µl sample was applied to a gas chromatograph. Separations were made on an all-glass column of U-type configuration (183 cm×4 mm, inside diameter), packed with 3% on Gas-Chrom Q (80-100 mesh) operating at an injector temperature of 140° C.; flame ionization detector temperature was 140° C.; carrier nitrogen was at 50 ml/min, and the column was maintained (isothermal) at 110° C. The retention time of the n-butaneboronic ester of dianhydrogalactitol was 17.2 minutes, and the retention time of TMS-erythritol was 19.2 minutes.

Binding Studies

To determine the propensity for dianhydrogalactitol binding to blood components, 2 ml of fresh whole dog blood was incubated with [$^{14}$C]dianhydrogalactitol (specific activity 40.2 µCi/mg) at 37° C. After incubation, the mixture was centrifuged, the phases were separated, and 100 µl of the supernatant (plasma) and 100 µl of the semisolid precipitate (erythrocytes) were transferred to clean tubes. To each tube 1 ml of an 0.5 N HCl solution was added, and the mixtures were heated in a boiling water bath for 30 minutes. The mixtures were cooled, 1 ml of 10% metaphosphoric acid was added, and the solutions were allowed to stand at room temperature for 10 minutes. These mixtures were then centrifuged, and 1 ml of the supernatant was added to scintillation vials containing 15 ml of Aquasol™ (New England Nuclear). Water (1.5 ml) was added to each vial to yield clear solutions. Samples were counted to 1% accuracy against an external standard in a Beckman LS-150 scintillation counter.

To determine the reversibility of binding, 10 ml of fresh whole blood was incubated for 2 hours at 37° C. with 46.8 µg of [$^{14}$C]dianhydrogalactitol. The mixture was centrifuged, and the precipitate was washed twice with isotonic phosphate buffer (pH 7.4). The precipitate was resuspended in a volume of buffer so that the concentration of erythrocytes in the suspension was equivalent to that in the original blood sample as determined from the hematocrit (49.6±0.2%). Five milliliters of this suspension was placed in a dialysis sac (Union Carbide Inc.; cylindrical diameter=15 mm; molecular weight cutoff≈5000) and dialyzed against 100 ml of isotonic phosphate buffer (pH 7.4) at 37° C. Buffer was changed 2 and 5 hours after the experiment was initiated. At 2, 5, and 14 hours after dialysis was initiated, 1-ml samples of the dialysis solution (buffer) were removed, added to 15 ml of scintillation cocktail (Aquasol™), and counted as previously described. After 14 hours, the contents of the dialysis sac were centrifuged, and the supernatant and precipitate fraction were analyzed as described above.

Calculations

The plasma decay curve for intact dianhydrogalactitol appeared to show biexponential behavior at both the 3 mg/kg and 6 mg/kg doses in dogs. Levin et al., supra, previously fit the pharmacokinetics of [$^{14}$C]dianhydrogalactitol in rats to the two-compartment model described by Wagner. The two-compartment model predicts that the dianhydrogalactitol plasma level versus time curve in dogs after rapid intravenous injection should show a biexponential decay and be described by the equation:

$$C_p = Ae^{-\alpha t} + Be^{-\beta t} \qquad \text{(Equation (1))}$$

where $C_p$ is the plasma level at time t and A, $\alpha$, B, and $\beta$ are parameters that are complex functions of $k_{12}$ and $k_{21}$ (compartment transfer constants), $k_{el}$ (elimination constant from compartment 1), D (dose), and $V_1$ (volume of compartment 1). Calculation of A, $\alpha$, B, and $\beta$ for a given dose of drug allows the calculation of not only $k_{12}$, $k_{21}$, $k_{el}$, and $V_1$, but also AUC (area under the plasma level time curve) $V_{Dss}$ (volume of distribution of the drug at steady state), and Cl (total body clearance).

The observed plasma level decay curve for each animal and dose was fit to Equation (1) by the use of the simplex method of fitting (S. N. Deming & S. L. Morgan, "Simplex Optimization of Variables in Analytical Chemistry," *Anal. Chem.* 45: 287A-283A (1973), incorporated herein by this reference). Only plasma level data points above 0.4 µg/ml were used in the computer fitting. Approximate values of A, α, B, and β were generated, which, along with the known doses of 3 mg/kg or 6 mg/kg, allowed the calculation of the various other parameters from standard equations.

Results

The gas chromatographic method described (Kimura et al., supra) permitted the monitoring of dianhydrogalactitol levels in plasma for approximately 120 minutes, i.e., until drug concentrations decreased below 100 ng/ml. However, accurate and reproducible results were limited to levels above 400 ng/ml. Derivatization of dianhydrogalactitol with n-butaneboronic acid was performed to increase the volatility of dianhydrogalactitol and enhance its thermal stability, which would thus facilitate its gas-chromatographic analysis (F. Eisenberg, "Cyclic Butaneboronic Acid Esters: Novel Derivatives for the Rapid Separation of Carbohydrates by Gas-Liquid Chromatography," Carbohydr. Res. 19: 135-138 (1971)). The plasma concentration at each point is the mean of duplicate sample analysis. The solid lines were generated by a fit to Equation (1) utilizing the computer-generated values of A, α, B, and β (Deming & Morgan, supra).

Dog 2 died 12 days after administration of the higher dose of drug, whereas dog 1 died 7 days after injection with 6 mg/kg of dianhydrogalactitol. In the final 24-48 hours before death, both animals showed signs of lethargy and bleeding from the mouth. Death was apparently associated with bone marrow hypoplasia, leucopenia, and thrombocytopenia, typical of dianhydrogalactitol intoxication.

Dianhydrogalactitol binds to erythrocytes, 37.7% of the incubated dose being bound within 2 hours. The plasma concentration of radiolabeled material remained essentially constant, dropping only slightly over the 2-hour period, based on radiochemical assay. This method cannot discriminate between parent drug, metabolites, and degradation products. By means of the gas chromatographic method to quantitate dianhydrogalactitol, which quantitates dianhydrogalactitol alone and not metabolites, degradation products, or products of alkylation of nucleic acid molecules, the amount decreased significantly over the time of the study. The nature of binding to erythrocytes was determined by an equilibrium dialysis experiment. Although 50% of the dianhydrogalactitol that was initially bound to erythrocytes was lost to the dialysis medium within 2 hours, 36% of the initially present drug remained with the erythrocytes after dialysis for 14 hours. This suggests that some of the drug does bind irreversibly to blood components, a fact consistent with the known alkylating action of dianhydrogalactitol.

Discussion

Unlike the previously reported results, the study reported in this Example utilizes a specific gas chromatographic procedure to determine the plasma concentration of dianhydrogalactitol. Thus, the pharmacokinetic parameters generated in this Example represent the time plasma level decay curves of unmetabolized dianhydrogalactitol. The rapid elimination of dianhydrogalactitol (mean $t_{1,2,\beta}$, 26.6 min) and large clearance (mean Cl, 23.4 ml min$^{-1}$ kg$^{-1}$) at doses of 3 and 6 mg/kg, demonstrate that the intact drug is rapidly cleared from the animal. The mean value of V (462 ml/kg) suggests that dianhydrogalactitol is widely distributed throughout extracellular and some intracellular fluid. Furthermore, the mean value of $V_{Dss}$ (779 ml/kg) suggests that some tissue binding of dianhydrogalactitol also suggests that some tissue binding of dianhydrogalactitol also occurs. Irreversible and reversible binding of dianhydrogalactitol to erythrocytes was demonstrated.

Although the pharmacokinetics of dianhydrogalactitol at 3 and 6 mg/kg were observed in only one dog, the lack of any apparent significant alteration in the pharmacokinetic parameters with dose indicates that dianhydrogalactitol distribution and elimination are dose-independent over the very limited dose range studied. Because of the toxicity of dianhydrogalactitol at doses greater than 3 mg/kg and the limitations of the assay procedure employed in this Example, it was not possible to study a wider dose range in this Example.

The analytical method used in this Example is highly specific for dianhydrogalactitol and is able to discriminate between dianhydrogalactitol and its degradation products or metabolites. Such products would probably result from either opening of the epoxide ring (by reaction with circulating nucleophiles), oxidation of hydroxyl moieties, or a combination of both pathways. In solution, dianhydrogalactitol may undergo intramolecular rearrangement to generate the thermodynamically more favored secondary epoxide.

However, n-butaneboronic acid reacts only with 1,2-glycols to form volatile esterified derivatives (Eisenberg, supra). Rearrangement of dianhydrogalactitol would yield a product incapable of reaction with the derivatizing reagent n-butaneboronic acid. Therefore, this method is capable of distinguishing between 1,2:5,6-dianhydrogalactitol and 1,2:4,5-dianhydrogalactitol. The detection limits of the gas chromatographic method (100 ng/ml plasma) fall short of radiochemical analysis; however, the chromatographic method has enhanced specificity.

The results of this Example show that dianhydrogalactitol kinetics follow simple two-compartment model behavior at both 3 and 6 mg/kg levels in dogs. In vitro experiments with fresh blood indicated that dianhydrogalactitol binds both reversibly and irreversibly to erythrocytes, consistent with its known alkylating activity (Levin et al., supra; G. P. Wheeler et al., "Interrelationships of Some Chemical, Physicochemical and Biological Activities of Several 1-(2-Haloethyl)-1-nitrosoureas," Cancer Res. 34: 194-200 (1974)). The assay used is specific for intact dianhydrogalactitol and can measure plasma levels of dianhydrogalactitol down to 0.1 μg/ml in plasma.

Advantages of the Invention

The present invention provides more effective and efficient methods for veterinary use of dianhydrogalactitol, diacetyldianhydrogalactitol, and dibromodulcitol, especially in the treatment of malignancies. Such more effective and efficient methods for veterinary use of dianhydrogalactitol, diacetyldianhydrogalactitol, and dibromodulcitol will improve efficacy, prevent or reduce the occurrence of significant side effects, and will identify categories of veterinary subjects and situations in which these drugs can be effectively employed.

Compositions and methods according to the present invention possess industrial applicability for the preparation of a medicament for the treatment of a number of diseases and conditions in veterinary subjects, especially hyperproliferative diseases, and possess industrial applicability as pharmaceutical compositions.

The method claims of the present invention provide specific method steps that are more than general applications of laws of nature and require that those practicing the method steps employ steps other than those conventionally known in the art, in addition to the specific applications of laws of nature recited or implied in the claims, and thus confine the scope of the claims to the specific applications recited therein. In some contexts, these claims are directed to new ways of using an existing drug.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

What is claimed is:

1. A method for treating a malignancy in a companion animal comprising the step of administering a therapeutically effective quantity of a therapeutic agent selected from the group consisting of dianhydrogalactitol, diacetyldianhydrogalactitol, and dibromodulcitol to a companion animal selected from the group consisting of a dog, a cat, and a horse in need thereof to treat the malignancy in the companion animal by the action of the therapeutic agent in the companion animal, wherein the malignancy is selected from the group consisting of a malignancy of the brain; osteosarcoma; non-Hodgkin's lymphoma; Hodgkin's lymphoma; skin cancer; lymphoid malignancies; connective tissue malignancies; mouth malignancies; pharynx malignancies; melanoma; colorectal cancer; non-small cell lung cancer; cervical carcinoma; bladder carcinoma; and metastatic hemangiopericytoma; and wherein the therapeutic agent is administered in a dosage of about 5 to 40 mg/m$^2$, once or twice/week, every 4-6 weeks.

2. The method of claim 1 wherein the therapeutic agent is dianhydrogalactitol.

3. The method of claim 1 wherein the malignancy is selected from the group consisting of a malignancy of the brain and an osteosarcoma.

4. The method of claim 1 wherein the therapeutic agent is administered by a route of administration selected from the group consisting of intravenous, parenteral, intraperitoneal, transcutaneous, subcutaneous, intramuscular, intraurethral, and oral administration.

5. The method of claim 1 wherein the therapeutic agent is administered in a pharmaceutical composition.

\* \* \* \* \*